United States Patent [19]

Filler

[11] Patent Number: 5,948,384
[45] Date of Patent: Sep. 7, 1999

[54] PARTICULATE AGENTS

[75] Inventor: Aaron Gershon Filler, Seattle, Wash.

[73] Assignee: Syngenix Limited, United Kingdom

[21] Appl. No.: 08/473,697

[22] Filed: Jun. 7, 1995

Related U.S. Application Data

[62] Division of application No. 07/988,919, Apr. 5, 1993, abandoned.

[30] Foreign Application Priority Data

| Sep. 14, 1990 | [GB] | United Kingdom | 9020075 |
| Oct. 30, 1990 | [GB] | United Kingdom | 9023580 |
| Dec. 17, 1990 | [GB] | United Kingdom | 9027293 |
| Jan. 7, 1991 | [GB] | United Kingdom | 9100233 |
| Jan. 16, 1991 | [GB] | United Kingdom | 9100981 |
| Jan. 31, 1991 | [GB] | United Kingdom | 9102146 |
| May 20, 1991 | [GB] | United Kingdom | 9110876 |
| Jul. 30, 1991 | [GB] | United Kingdom | 9116373 |
| Aug. 19, 1991 | [GB] | United Kingdom | 9117851 |
| Aug. 30, 1991 | [GB] | United Kingdom | 9118676 |

[51] Int. Cl.$^6$ .......................... A61K 51/00; A61M 36/14
[52] U.S. Cl. .................. 424/1.29; 424/1.11; 424/1.37
[58] Field of Search ................... 424/1.29, 1.33, 424/1.11, 1.37; 600/1, 2, 3

[56] References Cited

U.S. PATENT DOCUMENTS

| 4,430,320 | 2/1984 | Shigematsu et al. . | |
| 4,452,773 | 6/1984 | Molday | 424/1.1 |
| 4,479,940 | 10/1984 | Bizzini | 424/177 |
| 4,552,145 | 11/1985 | Riley et al. | 128/630 |
| 4,594,336 | 6/1986 | Bizzini | 514/2 |
| 4,690,130 | 9/1987 | Mirell | 128/1.3 |
| 4,752,567 | 6/1988 | De Brabander et al. | 435/7 |
| 4,813,399 | 3/1989 | Gordon | 600/12 |
| 4,827,945 | 5/1989 | Groman et al. | 128/653 |
| 4,849,210 | 7/1989 | Widder | 424/9 |
| 4,863,715 | 9/1989 | Jacobsen et al. | 424/9 |
| 5,019,369 | 5/1991 | Presant et al. | 424/1.1 |
| 5,043,101 | 8/1991 | Gordon | 252/408.1 |
| 5,077,035 | 12/1991 | Wieland et al. | 424/1.1 |
| 5,169,933 | 12/1992 | Anderson et al. | 530/391.3 |
| 5,248,772 | 9/1993 | Siiman et al. | 536/112 |
| 5,382,468 | 1/1995 | Chagnon et al. | 428/328 |
| 5,424,288 | 6/1995 | Order | 514/2 |
| 5,492,814 | 2/1996 | Weissleder | 435/725 |
| 5,554,498 | 9/1996 | Filler et al. | 435/5 |

FOREIGN PATENT DOCUMENTS

| 0455093 | 11/1991 | European Pat. Off. . |
| 8601112 | 2/1986 | WIPO . |
| 8800060 | 1/1988 | WIPO . |
| 8909625 | 10/1989 | WIPO . |
| 9001295 | 2/1990 | WIPO . |
| 9101144 | 2/1991 | WIPO . |
| 9104014 | 4/1991 | WIPO . |

OTHER PUBLICATIONS

Gallagher, J.E., G. George, A.R. Brody (1987) "Sialic acid mediates the initial binding of positively charged inorganic particles to alveolar macrophage membranes" Am. Rev. Respir. Dis. 135(6):1345–1352 (abstract only).

Menetrey, D. (1985) "Retrograde tracing of neural pathways with a protein–gold complex" Histochemistry 83(5):391–395 (abstract only).

*Primary Examiner*—José G. Dees
*Assistant Examiner*—Dameron Jones
*Attorney, Agent, or Firm*—Saliwanchik, Lloyd & Saliwanchik

[57] ABSTRACT

A novel means of pharmaceutical delivery for therapy of prophylaxis or to assist surgical or diagnostic operations on the living body is provided by neuronal endocytosis and axonal transport following pharmaceutical administration into vascularized, peripherally innervated tissue, e.g. intramuscular injections of a nerve adhesion molecule in coupled particle comprising a physiologically active substance or a diagnostic marker.

19 Claims, 30 Drawing Sheets

FIG. 2C

| | | |
|---|---|---|
| 43 β+, (1.22/0.82), 3.9h; 22%γ(0.37) 47 β-, (0.439), 3.4d; 68%γ(0.15) 0.301, 48.6 MHz 45 21 Sc 3+, 0.75 -5.10 | 45 β+, (1.04), 3.1h; γ(minimal) 48,46,47 22 Ti 4+, 0.61 -4.06 | 48 β+ (0.70:50%), 16.0d; 100%γ(.98) 0.381, 52.6 MHz 51,50 23 V 2+, 0.79 -3.44 |
| 90 β-, (2.27), 64h 89 39 Y 3+, 0.90 -5.31 | 89 β+, (0.90:22%), 78.4h; 87%γ(0.59), 6%γ(1.51) 90,92,94 40 Zr 4+, 0.72 -3.98 | 90 β+, (1.50), 14.6h, 97%γ(1.14) .482, 48.8 MHz 93 41 Nb 3+, 0.72 -2.93 |
| | | |
| | | |

FIG. 2D

| 24Cr 3+, 0.61 | 25Mn 2+, .83 | 26Fe 3+, 0.65 / 2+, 0.78 | 27Co 2+, 0.75 | 28Ni 2+, 0.69 |
|---|---|---|---|---|
| 52, 53, 50 | 52 β+, (0.58), 5.6d; 100% γ(1.43) 90% γ(0.74) 0.175, 49.4 MHz 55 | 52 β+, (0.804), 83h, 99% γ(0.97) 56, 54, 57 | 55 β+, (1.50), 18.2h; 80% γ(.93) 0.277, 47.2 MHz 59 | 57 β+, (0.712), 36.1h, 80% γ(1.4) 15% γ(1.9) 58, 60, 62 |
| −2.62 | −3.72 | −3.84 | −4.18 | −4.46 |
| | | 44Ru 3+, 0.68 | 45Rh 1+ / 3+, 0.67 | 46Pd 2+, 0.86 |
| | | 105 β−, (1.87), 4.4h; 48% γ(0.73) 105m ⇒ Rh γ, 45s 102, 104, 101, 99 | 99 β+, (1.03), 16d 105 β−, (0.56), 35.9h; 19% (0.31) 103 | 109 β−, (1.03), 13.5hγ 103K 17d 106, 108, 105 |
| | | −1.92 | −3.10 | −5.04 |

FIG. 2E

| 67 β-, (0.40/0.48), 61.9h, 47%γ(0.18) | | 73 β-, (1.19), 4.9h, 47%γ(0.29) | | |
|---|---|---|---|---|
| .064, 53.0 MHz 63,65 $_{29}Cu_{2+,0.57}$ -4.81 | 64,66,68 $_{30}Zn_{2+,0.73}$ -5.24 | 69,71 $_{31}Ga_{3+,0.62}$ | | |
| | | 109 β+, (0.79), 4.3hγ .332, 43.8 MHz 115, 113 $_{49}In_{3+,0.80}$ | | |

FIG. 2H position affinity — oxid. state

| | |
|---|---|
| | |
| | |
| 143 n+, (1.7), 13.6d<br><br>0.26, 54 MHz  141<br><br>₅₉Pr₃₊, 0.99 | |
| 135 n+, (0.81), 17.2h<br><br>140, 142, 138<br><br>₅₈Ce₃₊, 1.01 | |
| | |

FIG. 2L

| | | |
|---|---|---|
| 180 β+, (1.1), 20h<br>186 β-, (1.07),<br>90h; 9%γ(0.137),<br>188 β-, (2.12),<br>16.7h; 10%γ(0.16)<br>189 β-, (1.00),<br>24h; 100%γ(0.22)<br>0.086, 45.6MHz<br>₇₅Re ⁱ⁸⁷,¹⁸⁵<br>₄₊, 0.63<br>-0.97 | 194 β-, (2.24),<br>17.4h; 10%γ(0.33)<br><br>193, 191<br>₇₇Ir ₃₊, 0.68<br>-1.53 | 186α, (4.23),<br>3.0hγ<br><br>195, 194, 196<br>₇₈Pt ₂₊, 60<br>-3.63 |

FIG. 2M

| | |
|---|---|
| | |
| | |
| $^{154}$ β+<br>21h<br><br>159<br>$_{65}$Tb $_{3+,0.92}$ | |
| $^{159}$ β−,(0.95)<br>18.0h; 9%γ(0.363)<br><br>158,160,156,154<br>$_{64}$Gd $_{3+,0.94}$ | |
| | |

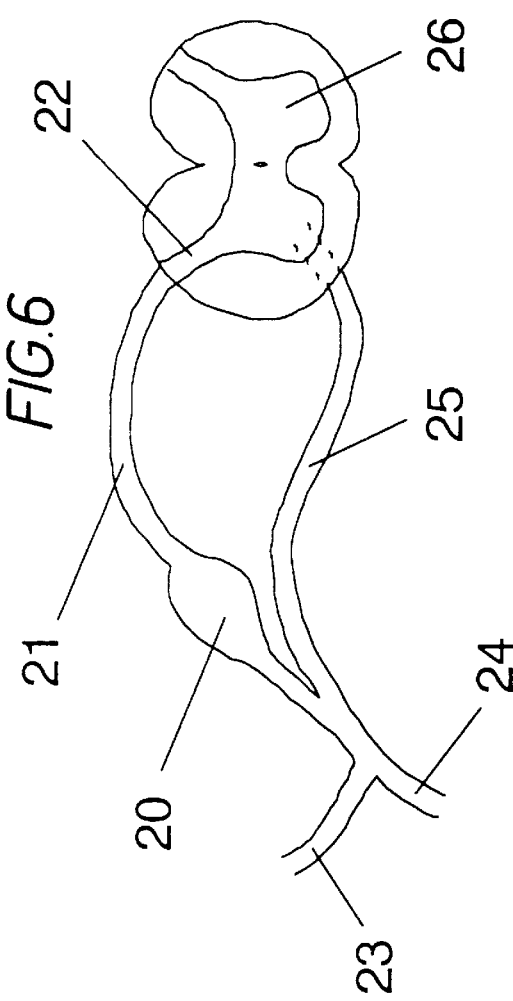
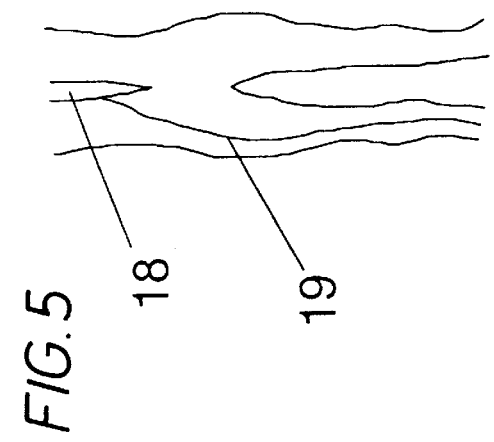
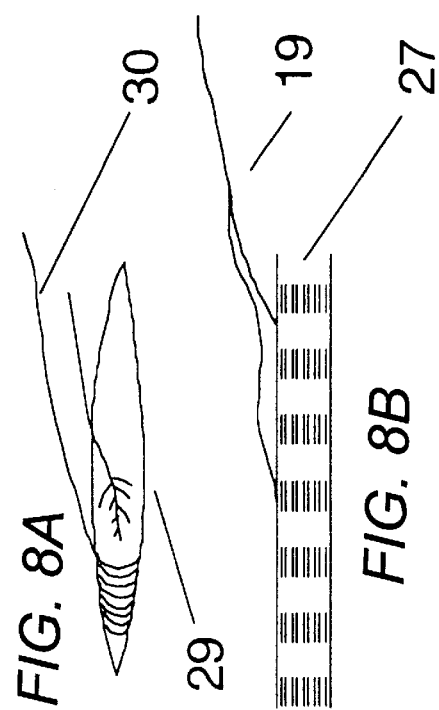
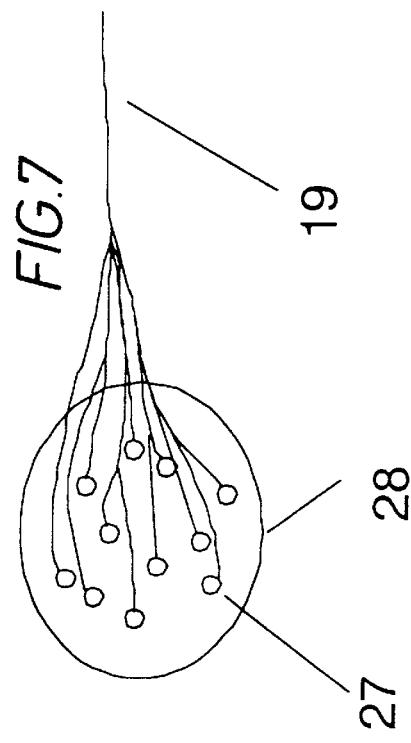

59

60

PARTICULATE AGENTS

This is a division of application Ser. No. 07/988,919, filed Apr. 5, 1993 now abandoned.

This invention relates to novel particulate agents for use in diagnostics and therapy, especially in diagnostic imaging, and more particularly diagnostic imaging or therapeutic treatment via the neural system.

In the living body, pain, paralysis and neural dysfunction can be inferred from electrical studies such as EMG, NCV and SSEP, but these kinds of assessment have continued to prove awkward and imprecise. While CT and MRI have made it possible to diagnose a wide variety of structural problems affecting the brain and spinal chord, and while studies on excised tissue and post mortem studies have enabled neuronal pathways to be traced, there is currently virtually no effective means by which diagnostic functional imaging of the neural system, and especially the peripheral nervous system, can be achieved in vivo.

Diagnostic imaging of nervous system function has a multitude of potential applications which will readily be apparent to the physician or neurosurgeon and many of these are discussed further below. Thus for example the possibilities would exist to visualize the impact of neurofibrillary tangles as they develop, to locate and assess nerve compressions, to verify the effectiveness of surgical vagotomy and to measure the response of the injured spinal cord to attempts at treatment.

It has now been realized that particulate agents suitable for use as contrast agents in diagnostic imaging modalities, especially MRI and PET, may be conjugated to nerve adhesion molecules and that following administration into body tissue, especially muscle, such agents are endocytosed by neurons having axon termini in that tissue and carried along the axons by axoplasmic flow thus allowing imaging of the axons and of the nerves of which they form part.

The endocytosis of nerve adhesion molecule (NAM) labelled agents can also clearly be utilized for the remote delivery of therapeutic agents, i.e. axoplasmic flow can serve to transport a therapeutically active agent comprising a nerve adhesion moiety from its administration site in tissue such as muscle to a remote site where it exerts its pharmacological effect. This is of particular interest where the sensitivity or accessibility of the remote site is such as to prevent direct administration of the pharmaceutical.

Thus viewed from one aspect the invention provides a method of treatment of the living human or non-human (preferably mammalian) body to effect a desired therapeutic or prophylactic treatment or assist diagnostic investigation or surgical treatment thereof, said method comprising administering into a vascularized peripherally innervated tissue site (preferably a muscle although possibly also other tissue sites innervated by cranial, peripheral or autonomic nerves) or into other tissue sites innervated by a spinal root a particulate pharmaceutical agent comprising a nerve adhesion moiety serving to promote neuronal endocytosis of said agent and a physiologically active or diagnostic marker moiety capable of axonal transport from said tissue site, and, where said method is to assist diagnostic investigation or surgical treatment, detecting axonal transport within said living body of a said agent having a diagnostic marker moiety, preferably by generating an image of at least part of said body.

Viewed from another aspect the invention provides the use of a particulate pharmaceutical agent comprising a nerve adhesion moiety serving to promote neuronal endocytosis of said agent and a physiologically active or diagnostic marker moiety capable of axonal transport following neuronal endocytosis of said agent for the preparation of a therapeutic, prophylactic or diagnostic composition for use on administration into vascularized peripherally innervated tissue or into other tissue sites innervated by a spinal root in a method of treatment of the living human or non-human body to effect a desired therapeutic or prophylactic treatment or assist diagnostic investigation or surgical treatment thereof.

Especially in the case of therapeutic or prophylactic treatment, the pharmaceutical agent is preferably administered into a tissue site, such as a muscle, having a volume of at least about ten times that of the group of nerve cells which are to transport the agent.

The term pharmaceutical agent is used herein to designate a substance capable of exerting a desired therapeutic or prophylactic effect and/or acting as a tracer, label, contrast agent or other diagnostic marker detectable in the intact living mammal. This substance may be a single compound but more generally will comprise a NAM coupled directly or indirectly to a physiologically active or diagnostically marked compound. Diagnostic marking may for example be with radiolabels, chromophores, fluorophores, by virtue of magnetic properties, or with atoms or structures capable of higher or lower radiation (eg. X-ray or sound) absorbance or reflectance than surrounding body tissue. Particulate NAM-coupled moieties may be coated or uncoated and if coated the coating may be selected to be broken down within the neuron after endocytosis, either slowly or more rapidly, or to be maintained during axonal transport.

For the purposes of the present invention it should be appreciated that while natural or synthetic, essentially inert, organic polymer particles (such as dextran coated microspheres or latex nanospheres) are capable of being endocytosed, these organic polymers unlike more specific and complicated molecules such as proteins, antibodies and antibody fragments are not considered to be nerve adhesion molecules.

The mean particle size for the particulate pharmaceutical agents used in the invention is conveniently in the range 5 to 100 nm, especially 8–70 nm, more particularly 10 to 50 nm and preferably about 20–30 nm.

Many of the pharmaceutical agents that may be used in the method of invention are themselves novel and viewed from a further aspect the invention provides a pharmaceutical agent comprising a nerve adhesion molecule coupled (directly or indirectly) to an optionally-coated, particulate, physiologically active or diagnostically marked substance, with the proviso that for diagnostically marked substances the substance is a metal oxide, metal sulphide or alloy.

For use to assist diagnosis, the pharmaceutical agent preferably has a diagnostic marker that can be detected non-invasively, eg. by virtue of its radiation emission or absorption characteristics or by virtue of its magnetic characteristics. For use in assisting surgery, for example to enable important nerve pathways passing through or near a wound site or other site undergoing surgical intervention, chromophores and fluorophores can also be used as diagnostic markers and in this instance in particular the use of nonparticulate as well as of particulate pharmaceutical agents might be contemplated.

One especially important group of pharmaceutical agents for use according to the invention is that of NAM-coupled particulate inorganic compounds, for example metal oxides, sulphides or alloys, where the inorganic material is selected for its magnetic properties, in particular ferri- and ferromagnetism and more particularly superparamagnetism, or includes within an otherwise essentially inert matrix atoms or molecules which are released gradually from the matrix to exert a therapeutic or prophylactic effect or which function as diagnostic markers, eg. radioisotopes or nuclides detectable upon MR spectroscopy. Many metal oxide structures may be utilized as the inorganic particles, and spinels and garnets have been found to be particularly useful in this regard. It should however be stressed that other well known inert and preferably essentially water insoluble metal compounds may be used, especially those having or capable of being doped to exhibit cooperative magnetic properties and those having lattices such as permit desired radioisotopes to be included. By alloys, mixed metals are of course included. Organic particulate matrices may also be used to accommodate a therapeutic compound or a diagnostic marker.

As is clear from the above, this invention is especially concerned with improvements in particulate pharmaceuticals which surprisingly result in providing access to new patterns of distribution within the body which were never previously possible. As a result of these new patterns of distribution, a number of previously intractable problems in medical diagnosis and treatment have now been solved.

For the particulate pharmaceutical agents in particular, the improvements include 1) improved control of particle size, 2) development of an effective means of affinity purification of the particles, 3) demonstration of a means of filter sterilization of the concentrated product late in the synthesis, and 4) widening the array of elements and concentration of those elements applied to medical uses in metal oxide or sulphide crystals or in alloys.

One of the most important consequences of these advances is the development of agents which can be delivered by, and make use of an entirely novel intraneural pharmaceutical route (IPR). In addition, these advances greatly simplify and reduce the cost of production of related particulate agents with previously known uses.

In a preferred embodiment, the agent comprises particles with a core metal oxide crystal, eg. of spinel or garnet structure, coated for example by dextran carbohydrate wherein the total size of the coated particle is between 100 and 500 Angstroms (10 to 50 nanometers) and where a targeting moiety (TM) is chemically bound to the coating in low concentration of TM per particle, preferably 1:1. The agent should preferably be virtually free of particles lacking an active TM, and compositions thereof are preferably sterilized by 0.2 or 0.1 micron microfiltration after final synthesis, affinity purification and concentration.

The uses of a given version of the agent depend upon the elements and isotopes (nuclides) used in the initial precipitation step in which the metal oxide crystal core is precipitated and coated and also upon the type of targeting moiety used. For each use, the nuclide and targeting moiety may be selected to benefit both from the general advantages of the simplicities of the preparatory method and to take advantage of the new types of pharmaceutical distribution which can be achieved by materials prepared in this way.

The inorganic particles in the preferred pharmaceutical agents used according to the invention generally fall into one of five categories:

i) particles exhibiting cooperative magnetic properties, in particular superparamagnetism, eg. ferrite particles such as inverse spinel ferrites, and thus detectable by magnetic resonance or magnetometric methods;

ii) particles incorporating a gamma or electron emitter radionuclide, and thus detectable by gamma detectors, scintigraphy or SPECT (single photon emission computed tomography) or thus capable of causing radiation treatment effects;

iii) particles incorporating an element of non-zero nuclear spin, eg. scandium, capable of being detected by magnetic resonance spectrometry;

iv) particles incorporating a positron ($\beta^+$) emitter radionuclide and thus capable of detection by PET (positron emission tomography);

v) particles incorporating a compound or element capable on release, eg. during degradation of the particle, of effecting a desired therapeutic or prophylactic effect.

Metal oxide particles of the first two types are clearly known but scandium containing spinels or garnets and the particles of the latter two types are novel and in themselves form further aspects of the present invention.

Thus viewed from a further aspect the invention provides a physiologically tolerable particulate metal oxide, metal sulphide or alloy with incorporated therein a positron emitter radionuclide and preferably an element having high positron affinity (eg. higher than that of iron, for example lithium or zinc). Such high positron affinity element containing particles are preferably spinels and are referred to herein as "spinel moderated positron emitters" (SMPE) These have several unique and surprising qualities which enhance the image resolution of PET.

Viewed from a further aspect the invention also provides a physiologically tolerable particulate garnet or spinel with incorporated therein atoms of scandium, of a radioactive yttrium isotope, of a sixth period metal (e.g. a lanthanide), of a high MR receptivity nuclide (e.g. at least as high as $_{71}Lu^{175}$), or of an element which on particle degradation has a desired therapeutic or prophylactic activity.

It will be appreciated that although the metals of the metal oxide, sulphide or alloy matrices of the particles of the invention may have naturally occurring positron emitting isotopes the particles according to the invention have significantly higher than natural abundance contents of these, e.g. for positron emitters an average of at least one, perhaps 10 or more atoms per 100 nm crystal. The natural occurrence of many $\beta^+$ emitters is less than 1 in $10^{20}$ and even one emitting atom per particle may suffice.

For other novel "doped" particles according to the invention, the active or marker nuclei may be isotopes which occur naturally, e.g. as impurities in naturally occurring oxides, sulphides or alloys—in this case again the particles according to the invention are distinguished by containing such atoms at higher than natural values, e.g. a hundred or even more per 100 nm particle.

The particles of the invention may be coated or uncoated and may derive their physiological tolerability at least in part from such a coating. They may moreover be coupled to a biotargetting moiety, for example an antibody, an antibody fragment or another NAM.

The particles of types i) and ii) mentioned above are also preferably of a spinel or garnet structure—the manufacture of particles of these types is already well known and need not be described further here. By way of interest however it may be noted that superparamagnetic crystals of this type have been proposed for use as MRI contrast agents in various patent publications of Nycomed AS, Schering AG, Advanced Magnetics Inc, etc (eg. U.S. Pat. No. 4,863,715 (Jacobsen) and U.S. Pat. No. 4,827,945 (Groman)).

There are a wide variety of targeting moieties or NAMs which can be used according to the invention. These include antibodies, monoclonal antibodies, antibody fragments, receptors, peptides such as endorphins, steroid molecules, viral fragments or coat proteins, cell surface antigens including various carbohydrates, lectins, immunoadhesins, neurotransmitter molecules, growth factors, and other proteins which promote endocytosis of the pharmaceutical agent by the axon termini. The use of lectins, such as WGA, is particularly preferred.

The synthesis of metal oxide crystals as particulates in stable aqueous solution has been of interest in crystalography and in the paint pigment industry. However, many of the relevant advances have grown out of studies of magnetism.

Many of the agents described herein involve specially synthesized versions of magnetite ($Fe_3O_4$). The crystal structure of magnetite is based on a mineral called spinel $MgAl_2O_4$. However, when specific proportions of ferric and ferrous ions are used instead of magnesium and aluminum as the metal ions in the lattice: $Fe(II)(Fe(III))_2O_4$, a particular set of electronic alignments and exchanges are produced which result in spontaneous magnetization.

The basic structure of magnetite involves a close-packed, face centred cubic crystal of oxygen atoms with metal ions placed at interstitial spaces in the crystal (see FIG. 1). The interstices are divided into "A" sites and "B" sites which have different interstitial locations relative to the oxygen array and which therefore give rise to two distinct sublattices within the crystal. In the naturally occurring mineral "spinel" ($MgAl_2O_4$) the A-sites are filled by Mg(II) and the B sites by Al(III). The assignment of atoms to sublattices is determined in part by size. The A-sites allow atoms of 0.3 to 0.6 angstrom radius while the B-sites allow atoms of 0.6 to 1.0 angstroms. In a normal spinel crystal, the A-sites are filled by divalent atoms while the B-sites are filled by trivalent atoms.

Magnetite is an "inverse spinel" crystal because it has trivalent iron in its A-sites, and a mix of divalent and trivalent iron in its B-sites. Each crystal subunit has 32 oxygens, 8 A-site Fe(III) atoms, 8 B-site Fe(III) atoms and 8 B-site Fe(II) atoms. The general formula for spinel ferrites is Mt(II): $(Fe(III))_2(O)_4$, where Mt can be any divalent transition metal or a charge balanced mix of monovalent and trivalent metals of appropriate ionic radius.

The Fe(III) atoms in the A sublattice are positioned so as to oppose and cancel the spin magnetization of the Fe(III) in the B sublattice. However, after this cancellation, the 8 Fe(II) remaining in the B sublattice have completely unopposed spin magnetizations. For each $Fe_3O_4$ formula unit, there is a net magnetization of 4 Bohr Magnetons due to the unopposed Fe(II) atoms. Each crystal subunit therefore has a magnetization of 32 Bohr Magnetons packed into a cube with a face that is 837 pm in length.

The magnetization of a ferrite can be altered by substituting different metals into the various interstices. For instance, Mn(II) has a magnetization of 5 Bohr Magnetons, so creation of an inverse spinel with the formula $Mn(II)(Fe(III))_2O_4$ should yield crystals with 5 Bohr Magnetons per unit. The use of Zn(II) has a quite different effect. It has no unfilled d-orbitals and so has zero magnetic moment. However, zinc tends to enter A sites causing a normal spinel organization for the crystal. Therefore, at each formula unit, a zero moment zinc opposes an Fe(III) with a moment of 5 Bohr Magnetons resulting in a net moment of 5 for the pair, the remaining Fe(III) are also unopposed, so the net moment is 10 Bohr Magnetons per formula unit (80 Bohr Magnetons per crystal subunit).

In actuality, this situation can prevail only for a low percentage of the total number of sites in a larger crystal. Zn(II) is actually too large for the A sites (0.77 angstrom radius) so that as the concentration of zinc exceeds 50%, there is a transformation into inverse spinel structure. In this arrangement, Fe(III) opposes Fe(III) cancelling each other out, and the unopposed Zn(II) have no moment, so the ferrite has a net magnetization of zero. This is sometimes useful in applications such as the heteronuclear tracers described below in which magnetization is not necessarily desirable.

In 1955 the term superparamagnetism was proposed to describe the behaviour of extremely small magnetic particles. The fundamental idea is that there is sufficient thermal agitation in a small particle that the tendency for the magnetic dipole axis to flip into various orientations is greater than the tendency to align as a coherent domain with a single fixed axis.

As the particle size increases above a critical size in the range of $10^6$ atoms, it becomes stable and coherently aligned as a spontaneously magnetized single domain. Below this critical size, the magnetic susceptibility is temperature and size dependent. Smaller particles at higher temperatures require stronger external fields to become detectably magnetized. Once magnetization is achieved, however, the total magnetization is related directly to the size of the particle.

The behaviour of a superparamagnetic particle is described by a relaxation rate which reflects the rate at which local magnetic moments within the particle will flip spontaneously. In order to flip, an energy barrier which is proportional to the volume of the particle and to the anisotropy of the material must be overcome. In a domain sized particle, the magnetization settles along one single axis because the energy barrier is too great to permit flipping at the temperature of the experiment. At sub-domain size, the energy barrier is low enough that the flip rate becomes exceedingly rapid. The size at which this transition occurs is temperature dependent and also dependent on the composition of the particle. (For present purposes the relevant temperature for determining whether or not a substance is superparamagnetic is body temperature).

By the substitution of some metals such as cobalt in place of some of the Fe(II) in the lattice, the crystals become more anisotropic and this tends to slow the rate of flipping and so lower the critical size for a stable domain.

When larger ions are included in the crystal matrix, the spinel structure cannot accommodate them. This is particularly important for the use of elements from the lanthanide series. However, lanthanides may be accommodated by the garnet crystal structure. The natural form of this crystal is $Ca_3Al_2(SiO_4)_3$ or $3CaO.Al_2O_3.3SiO_2$. An analogous structure is achieved with the composition $Ln_3Fe_5O_{12}$, wherein Ln is a lanthanide element. (A common example made using Yttrium is called YIG or Yttrium-Iron-Garnet and is used for instance in lasers). Although small amounts of the lanthanides are accommodated within spinel crystals, stoichiometries which favour garnet formation are more important as larger percentages of lanthanides are included.

A novel type of spinel crystal developed and synthesized according to the invention uses scandium in place of aluminum in the preparation of coated, colloidal spinel crystals. The most stable of these are $Mg(II)(Sc(III))_2O_4$ or magnesium scandites. These are helpful vehicles in several of the applications described below. These crystals are not magnetic. Scandium has stable trivalent chemistry but, unlike yttrium and lanthanides, is similar in ionic size to the remaining transition metals.

Methods for precipitating ferrites from metal salts date back into the 1800's and several investigators have modified these methods in attempts to develop improved ferrofluids. Elmore in Phys. Rev. 54: 309–310 (1938) explored ammonia precipitation of ultrafine ferrite particles in aqueous solutions and first demonstrated that their aggregation increased when they approached an applied magnetic field.

A further step towards developing stable colloidal ferrofluids came in 1965 with the development of a method for grinding magnetic materials into fine powders and then suspending them in oleic acid by sonication (see U.S. Pat. No. 3,215,572). Takada and Kiyama in Proc. Int. Conf. (ICF-1), U. Tokyo Press (Ed. Hoshino et al), p.69–71 (1970) reexplored a variety of methods for precipitating ultrafine crystals of magnetite and developed a new oxidation method although this body of work did not address the problem of keeping the particles in suspension.

Reimers and Khalafalla in Bu Mines TPR 59:13 (1972) used an ammonia peptization method to create aqueous suspensions of ground particles. In their initial method, an acid treatment followed by sonication is used to induce interaction with solvent molecules to prevent clumping of the particles and maintain suspension. Subsequently, they developed a modification of Elmore's ammonia precipitation method to create more stable, dilutable suspensions in which molecules of dodecanoic acid are chemically adsorbed onto the surface of the magnetite particle (see Khalafalla and Reimers in IEEE Trans Mag 16: 178–183 (1980)). This yielded dilution-stable solutions of superparamagnetic particles.

Biologists became interested in small magnetic particles as potential means of carrying out biochemical separations and developed various means of incorporating domain sized particles into beads. These did not need to be soluble in the form initially used. However, building on methods used to create dense immunospecific labels for electron microscopy, an aqueous technique developed by Molday (see U.S. Pat. No. 4,452,773 and J. Immunol. Meth 52: 353–367 (1982)) opened the way to a variety of biological applications.

The Molday method involves an ammonia precipitation synthesis in which dextrans are used to coat the magnetite. This results in an aqueous suspension of superparamagnetic particles which can be conjugated to a wide variety of types of molecules including antibodies and so used to carry out various types of separations. The advantage of the superparamagnetism of the Molday particles is that they do not tend to aggregate magnetically unless they are in an applied magnetic field. This simplifies the preparation of more elaborate compounds while permitting recovering of the magnetic properties when they are wanted after the synthesis is completed.

Whitehead et al (U.S. Pat. No. 4,554,088) developed a silane binding technique in which clusters of superparamagnetic magnetite particles each about 30 nm in size are bound in groups into larger particles about 500 nm in diameter (now marketed as "AMI-25"). In the silane matrix, the small particles are held apart from each other and so retain their superparamagnetism. They therefore do not aggregate and remain relatively soluble. However, the total magnetic moment of the entire larger particle is quite large so that biological separations can be carried out.

Sub-micron coated iron oxide particles have been proposed for use as intravascular X-ray contrast agents and a number of other medical uses have been described for other superparamagnetic particles including magnetic confinement for blockage of fistulas and thrombosis of aneurysms, use in producing focal diathermy for treatment of infection, selective removal of tumour cells from bone marrow, and use as MRI contrast agents.

There have now been a variety of clinical studies in which MRI contrast is achieved by intravenous injection of ferrites for evaluation of liver and spleen tumours and also after oral intake as a gastrointestinal contrast agent. In these cases, it is the particulate nature of the material that is used to achieve useful distributions in the body, either by their uptake by reticuloendothelial cells in liver and spleen, or by their confinement to the GI tract because of their indigestible nature.

Paramagnetic contrast agents such as gadolinium-DTPA act primarily by altering $T_1$ relaxation rates. Superparamagnetic agents cause their MRI contrast enhancing effect in a rather different fashion. When the external main MR field is applied, the particles are organized into acting as powerful microscopic magnets scattered through the tissue being imaged. These particles therefore result in large numbers of local inhomogeneities in the larger field to which the protons are exposed. In the vicinity of an activated magnetite particle, therefore, the Larmor frequency of the protons is shifted away from resonance with the RF pulse (away from 200 MHz in a 4.7 Tesla field) and so generate a less intense signal. At larger distances from a magnetite particle, the contrast agent's field will cause smaller changes in Larmor frequency, so that although the RF pulse is still fully absorbed, the slight differences will accelerate dephasing of the protons (i.e. shorten $T_2$). This is similar to the effect caused by the local field inhomogeneities in the main magnet. However, because the magnetite particles are themselves tumbling and moving over relevant time scales in the signal collection sequence, the rephasing pulses are ineffective. Therefore, particularly in $T_2$ weighted images, a single magnetite particle can have tremendous impact.

Indeed, experiments conducted in our laboratory show that a single 40 nm particle of magnetite can drive $T_2$ to less than 10 milliseconds in an area more than 10 microns in diameter. This is why exceedingly low concentrations of magnetite particles in the range of 50 picomoles/liters can be effective. Even greater sensitivity may be achieved by using specially designed pulse sequences based on current gradient echo techniques which are particularly sensitive to local variations in magnet r field homogeneity.

Widder (U.S. Pat. No. 4,849,210) and Jacobsen (U.S. Pat. No. 4,863,715) demonstrated the effectiveness of suspensions of ferromagnetic particles as intravenous MRI contrast agents with various methods of synthesis. Groman (U.S. Pat. No. 4,827,945) provided a number of additional methods of synthesis or superparamagnetic particles and suggested the MR intravascular use of a wide range of labelled particles analogous to those disclosed for in vitro use by Molday. Although the compounds they describe are physically very similar to those disclosed by Molday (U.S. Pat No. 4,452, 773) they discuss sterilization techniques and methods of use involving diagnostic MRI.

However, the particles produced by the methods of Groman vary in size from 100 to 5,000 Angstroms, cannot be filter sterilized in concentrated final form, and cannot be effectively purified by affinity chromatography since, like the compounds of Molday, they contain many constituents which will not pass readily through agarose based affinity media late in the preparation. Because of the need for autoclaving of the Groman products, the use of delicate protein ligands is severely limited because they cannot withstand autoclaving. It is possible to carry out the synthesis of Groman using ultraclean facilities so that final sterilization of the product is less important but this adds considerably to the expense of manufacture.

The products of the Groman synthesis are not useful for radionuclide imaging of axonal transport because most of the particles are too large to be endocytosed by neurons and only a small proportion will carry active targeting moiety thus leading to unnecessarily large doses of radiation to achieve the required intraneural dose and leading to unnecessarily high tissue radiation background levels. Similarly, for MRI applications, the product of the Groman synthesis requires unnecessarily large injections into muscle to achieve the needed dose of small, specifically labelled sterilized particles desired.

The current invention achieves particular improved characteristics through the discovery that the use or repeated purification steps during the synthesis greatly improves the performance of the particles as biochemical reagents. These purifications remove dissolved metal ions as they appear during the synthesis since they can precipitate as hydrous oxides which impair the gel flow characteristics of the preparation during the synthesis. In addition, by using serial filtration steps after the initial precipitation, particles may be selected which are less than 500 angstroms in size (including the dextran coat). This helps assure the flow characteristics of the particles through the remainder of the synthesis and results in the production of only 100–500 angstrom particles which have a number of physiological advantages but are all large enough to retain superparamagnetic function.

Finally, and most importantly, when all these measures are taken, it is possible to take advantage of the versatility and convenience of re-usable agarose based affinity chromatography media to remove all particles which are not bound to a targeting moiety as well as permitting the discard of all particles whose bound targeting moiety has been inactivated or otherwise lost its specificity during the synthetic process. The potential to use these media is quite important since this permits the preparation of affinity media with a wide variety of ligands which can be used to purify a correspondingly wide variety of targeted particles. Although there are many applications of large (10 to 40 micron) magnetic beads as supports for affinity separations of other rinds or (non-magnetic) molecules and cells no previous preparation has achieved the affinity purification of the small superparamagnetic particles themselves upon a standard affinity chromatography matrix.

The final result is an agent with very nearly one active targeting moiety per particle with all particles selectively active and small enough for effective use. This can then be concentrated or formulated as desired and filter sterilization small volume if necessary. The final sterilization can me with conventional 0.2 micron filters for bacteria clearance or with 0.1 micron filters to assure removal or small mycobacterial contaminants.

An alternative method of obtaining high specific activity is to actually coat all of the particles in the preparation with a large number of molecules of the targeting moiety. This has the undesirable effects of greatly increasing the expense of the product when the targeting moiety is expensive to produce, increasing the antigenicity of the particle, and in many cases, altering the distribution of the particle in undesirable ways. It is well known from work in affinity chromatography on solid supports that spacing and density of affinity ligands are crucial determinants of efficacy.

There has been considerable interest in the medical uses of various types of microspheres and nanospheres. The composition of such particles include latex polymers from various methacrylates, polylactic acid, protein/albumin, lipids and various other materials (see for example Proc. Soc. Exp. Biol. Med 58: 141–146 (1978), AJR 149: 839–843 (1987), J. Cell Biol. 64: 75–88 (1975), J. Microencaps 5: 147–157 (1988), and Radiol. 163: 255–258 (1987)). These particles have been used as drug delivery systems, imaging agents, and for histological studies of axonal transport. They offer unique patterns of metabolism and biodistribution and continue to be the subject of intense investigation by many groups. The uses of such particles for in vivo diagnostic imaging of axonal transport or for the delivery of large numbers of atoms for heteronuclear imaging are among the new uses for microspheres described herein. The use of such particles as part of a drug delivery system that employs an intraneural route and axonal transport is also described here for the first time.

As mentioned above, the particles and the particulate agents of the invention preferably comprise therapeutically or prophylactically loaded or diagnostically marked inorganic crystals, e.g. $\beta^+$ emitter marked metal oxides.

Currently, the principal uses of positron emission tomography are in situations in which relatively short half-life emitters such as $_6C^{11}$ ($t^{1/2}$=20.3 minutes, 0.960 MeV), $_7N^{13}$ ($t^{1/2}$=9.96 minutes, 1.190 MeV), $_8O^{15}$ ($t^{1/2}$=2.03 minutes, 1.723 MeV), and $_9F^{18}$ ($t^{1/2}$=109.7 minutes, 0.635 MeV) are effective. However, for diagnostic or treatment situations such as the use of monoclonal anti-tumour antibodies or for imaging of axonal transport, it is sometimes necessary to allow several days for adequate tissue distributions to be achieved. There are a variety of relatively long half-life positron emitting nuclides, however, all of these have previously proven to be difficult to keep firmly bound to proteins over the necessary two to three days.

As demonstrated in FIG. 2, there are a number of nuclides emitting positron and electron $\beta$-particles all of which can be included in metal oxides, eg. spinels such as ferrites, either as substituents in the crystal lattice or as seeds, eg. $ZrO_2$, inside ferrite spinel shells. This provides a new and unique way of delivering these various nuclides to various medically useful locations in the body in a wide variety of new concentrations and half lives. A single ferrite particle can be used to attach hundreds or thousands or $\beta$-emitting atoms to a single antibody, thus far exceeding the intensity of signal per antibody molecule available in current preparations which generally provide one emitting atom per antibody molecule.

The uses for these various beta emitting ferrites are protean and include imaging tasks as well as a number of treatment modalities. From one point of view, this array of possible nuclide preparations presents a wide range of half lives and particle energies which can be used for various tasks. The great simplification provided is that all of these can be manufactured and delivered by means of essentially similar molecules with effectively identical chemistry. Most of these nuclides decay to daughters which are also easily accommodated in the crystal and therefore do not involve loss of integrity of the particle as decay progresses.

In one set of embodiments, the positron emitting isotopes of manganese ($_{25}Mn^{52}$), iron ($_{26}Fe^{52}$), cobalt ($_{27}Co^{55}$), or rhodium ($_{45}Rh^{99}$) are used in the synthesis of spinel particles, eg. sub-domain sized, superparamagnetic ferrite particles. The inclusion of cobalt or manganese in this type of ferrite has previously been difficult to achieve efficiently, but it is possible to reliably introduce cobalt, manganese, or other metals in amounts up to ⅓ of the number of metal atoms per formula unit, e.g. with the remaining ⅔ being Fe(III) if the stoichiometry of the desired crystal structure, e.g. garnet or spinel, is carefully considered and factors such as pH, temperature, and precursor metal salt and coating compound concentrations and the duration of heat incubation after precipitation are carefully controlled, preferably after optimization by routine experimentation. Thus as an example, for dextran coated particles it has generally been found advantageous to precipitate out from a saturated dextran solution. Thus all the divalent metal atoms may be replaced as opposed to the ½ or fewer suggested by Groman in U.S. Pat. No. 4,827,945.

These particles may be synthesized in such a way that they are stably coated with dextran or other hydrophilic molecules and the coating may then be activated and bound covalently to antibodies or any type of nerve adhesion molecule. Particles so fashioned will be detectable upon Positron Emission Tomography (PET) as positron sources, and also upon Magnetic Resonance Imaging (MRI) as superparamagnetic particles. Some of these will also be detectable upon Magnetic Resonance Spectroscopy (MRS) as high receptivity nuclei at selected frequencies or on X-ray CT scanning where the Z-number and particle concentration is sufficient.

In positron ferrites made with $_{25}Mn^{52}$ the emission detection is based on the 0.511 MeV annihilation photons due to positron decay ($\beta$+27.9%, 0.575 MeV, E.C. 72.1%) with a half life of 5.59 days and associated gamma emissions of (100%, 1.434 MeV; 94.5%, 0.935 MeV; 90%, 0.744 MeV; 5%, 1.33 MeV; 4%, 1.25 MeV; 3%, 0.85 MeV) to $_{24}Cr^{52}$ which is stable. This is a decay half life which is quite well suited to long nerve transports and to full monoclonal antibody distribution for tumour studies. Further, with a relatively low positron energy of just 0.575 MeV, the spatial resolution is substantially better than any positron emitter in active clinical use including $_9F^{18}$. The high gamma emission may make $_{25}Mn^{52}$ less attractive for clinical use in some situations, but as indicated by FIG. 2, there are many alternatives.

Positron ferrites can also be made with $_{26}Fe^{52}$ which undergoes positron decay ($\beta$+56%, 0.804 MeV; EC 43.5%) with a half life of 8.275 hours and associated gamma emissions (99.2%, 0.169 MeV) to $_{25}Mn^{52m}$ which is metastable and decays with a half life of 21.1 minutes by positron decay ($\beta$+96.27%, 2.631 MeV; EC 1.53%) and associated gamma emission (97.8%, I.434 MeV) to stable $_{24}Cr^{52}$ as well as by isomeric internal conversion (2.2%, 0.378 MeV) to $_{25}Mn^{52}$.

This type of positron ferrite has the advantage of a strong positron emission signal during the day of injection with a fairly rapid decline towards the continuing positron emission of the $_{25}Mn^{52}$ with a 5.7 day half life. This is particularly useful in neuropathy studies where an initial assessment of rate of transport is desired with a follow-up study done at several days to assess the amount of transport. At the time of the initial study, only a small fraction of the intramuscular dose will have entered the nerve, so a relatively high activity injection is needed. However, after several days, the amount in the nerve will be much larger, and it is then helpful to minimize the continuing absorbed dose to the patient by delivering it as the 2.2% of the $_{25}Mn^{52m}$ converted to $_{25}Mn^{52}$.

An intermediate half life can be provided by positron ferrites made with $_{27}Co^{55}$ which undergoes positron decay ($\beta$+77%, 1.54 MeV; EC 23%) with a half life of 17.5 hours and associated gamma emissions (75%, 0.93 MeV; 16.5%, 1.41 MeV; 20.3%, 0.477 MeV; 7%, 1.32 MeV; 3%, 1.37 MeV) to $_{26}Fe^{55}$. This nuclide of iron then decays slowly by K-shell electron capture (0.006 MeV) with a half life of 2.7 years to $_{25}Mn^{55}$ which is stable.

Although the half life of this cobalt positron emitter may be useful for some studies, its use is inhibited by the decay pattern of $_{26}Fe^{55}$; the energy of the photon is quite low, but the irradiation continues for a long time and virtually all the energy is deposited within tissue as non-penetrating radiation. This type of ferrite, however, does have the advantage of yielding a ferrous ferrite which is a chemically quite stable metal oxide that is cleared from the body differently than ionic iron. Further, unlike positron ferrites decaying towards an increasing composition of chromium or titanium, these compositions result in chemically stable ferrite particles with good magnetic properties and so remain effective superparamagnetic MR contrast agents as decay progresses.

A fourth type of positron ferrite can be synthesized with $_{45}Rh^{99}$ which undergoes positron decay (1.03 MeV) with a half-life of 16.0 days and no associated gamma emission to $_{44}Ru^{99}$ which is stable. This is a longer half life than will generally be needed but may be helpful in transneuronal transport studies intended to cross a synapse for transport in a second nerve in a chain. In particular, this could be helpful in studies of spinal cord injury. Also this sort of positron ferrite could be used in studies intended to assess the acute effect of surgery, where a diagnostic study is done and then a second study is required several days after the surgery to assess whether an accumulation of transported molecules at a compression site had commenced to clear.

The decay for $_{21}Sc^{43}$ ($\beta$+78%, 1.22 MeV; EC 22%) and associated gamma emission (22%, 0.373 MeV) with half life of 3.9 hours to stable $_{20}Ca^{43}$ make this very promising for clinical work. Particularly for rate of transport studies in the lower extremity which are carried out after a few hours, this may be a completely adequate half life to allow observation of the advancing front of the transport pulse. The substantial increase in ionic radius and the tendency to change from trivalence to divalence upon transition from Sc to Ca will be disruptive to the spinel crystal, but this may aid in the more rapid metabolism of the particles.

Except for calcium, all of these nuclides are accommodated in the spinel ferrite crystal, although the chromium decay products from $_{25}Mn^{52}$ and $_{26}Fe^{52}$ will generate some regions of spinel chromite ($FeCr_2O_4$) within the inverse spinel ferrite ($Mt[II]O:Fe[III]_2O_3$) crystal. Similarly, some regions of ilmenite, perovskite, and titanium spinel will form in consequence of eq. $_{23}V^{18}$ decay. In any case, the transitions due to nuclear decay will not affect the biodistribution of the tracers on the time scale of imaging studies. The particles degrade slowly after initial concentration in the reticuloendothelial system of lover, lungs, and spleen.

The optimal method for producing $_{26}Fe^{52}$ with minimal $_{26}Fe^{55}$ contamination is by the irradiation of $_{24}Cr^{50}$ enriched chromium with cyclotron generated 38 MeV $_2He^4$ beams ($_{24}Cr^{50}(\alpha, 2n)_{26}Fe^{52}$) with subsequent acid extraction, oxidation, evaporative drying, ether phase separation, redrying and filtration for sterilization (see Zweit Int. J. Radiat. Appl. Instrum. Part A, Appl. Radiat, Isol 39: 1197–1201 (1988)). Other reactions available for the production of $_{26}Fe^{52}$ include $_{25}Mn^{55}(p, 4n)_{26}Fe^{52}$, $_{24}Cr^{nat}(\alpha, xn)_{26}Fe^{52}$, $_{24}Cr^{nat}(_2He^3,xn)_{26}Fe^{52}$, $_{28}Ni^{nat}(p,spall)_{26}Fe^{52}$ with subsequent acid extraction and purification by anion exchange chromatography, wherein $_{24}Cr^{nat}$ includes $_{24}Cr^{50}$ (4.35%), $_{24}Cr^{52}$ (83.79%), $_{24}Cr^{53}$ (9.50%), and $_{24}Cr^{54}$ (2.36%).

$_{25}Mn^{52}$ may also be synthesized by standard techniques including $_2He^3$ activation of Vanadium $_{23}V^{51}(_2He^3,2n)_{25}Mn^{52}$ (see Sastri Int. J. Appl. Rad. Isol. 32: 246–247 (1981)) or other cylcotron reactions including $_{24}Cr^{52}(p,n)_{25}Mn^{52}$, $_{24}Cr^{52}(d,2n)_{25}Mn^{52}$. Methods for $_{27}Co^{55}$ include $_{26}Fe^{54}(d,n)_{27}Co^{55}$, $_{26}Fe^{56}(p,2n)_{27}Co^{55}$, $_{26}Fe^{nat}(_2He^3, xnp)_{27}Co^{55}$, $_{25}Mn^{55}(_2He^3, 3n)_{27}Co^{55}$, $_{25}Mn^{55}(\alpha,4n)_{27}Co^{55}$, wherein $_{26}Fe^{nat}$ is composed of $_{26}Fe^{54}$(5.82%), $_{26}Fe^{56}$(91.8%), $_{26}Fe^{57}$(2.1%), and $_{26}Fe^{58}$(0.28%).

Generator techniques in which a longer half-life parent nuclide is synthesized and transported to the clinical site with subsequent extraction of the clinical useful daughter nuclide just prior to use can be arranged for several useful metals. These include $_{46}Pd^{100}$ (4.0 d K,$\gamma$)$\rightarrow_{45}Rh^{100}$ (20 h $\beta$+), $_{74}W^{188}$ (69 d $\beta$–: 188 m, 18 m $\gamma$) $\rightarrow_{75}Re^{188}$ (16.7 h $\beta$–), and $_{76}Os^{154}$ (6.0 y $\beta$–)$\rightarrow_{n}Ir^{194}$ (17.4 h $\beta$–).

A proposed cyclotron $_{21}Sc^{43}$ synthesis involves the following scheme which would apply for alpha particle bombardment of $_{20}Ca^{40}$ (thermal neutron cross section =0.43 barns):

$$_{20}Ca^{40}(\alpha, n)_{22}Ti^{43} \Rightarrow \beta + (0.56s) \Rightarrow {}_{21}Sc^{43}$$

$$_{20}Ca^{40}(\alpha, p)_{21}Sc^{43}$$

$$_{20}Ca^{40}(\alpha, d)_{21}Sc^{42} \Rightarrow \beta + (0.68s) \Rightarrow {}_{20}Ca^{42}$$

$$_{20}Ca^{40}(\alpha, 2n)_{22}Ti^{42} \Rightarrow \beta + (0.2s) \Rightarrow {}_{21}Sc^{42} \Rightarrow \beta + (0.68s) \Rightarrow {}_{20}Ca^{42}$$

$$_{20}Ca^{40}(\alpha, xn)_{22}Ti^{x}$$

$$_{20}Ca^{40}(\alpha, 3n)_{22}Ti^{41} \Rightarrow \beta + (0.09s) \Rightarrow {}_{21}Sc^{41} \Rightarrow \beta + (0.60s) \Rightarrow {}_{20}Ca^{41}$$

$$_{20}Ca^{40}(\alpha, 4n)[_{22}Ti^{40}]$$

The calcium and scandium are readily separated either by phase separation (see Hara in Int. J. Appl. Rad. 24: 373–376 (1973)) or by chromatography (see Kuroda in J. Chrom 22: 143–148 (1966)) which also permits separation of any titanium.

These and other transition metal or lanthanide nuclides can be used in the synthesis of radioactive metal compounds (e.g. a metal oxide, metal sulfide or alloy, such as a ferrite) for use in monoclonal antibody based treatment of tumours by irradiation. Here again, the biodistribution and clearance of the delivered radionuclides is quite different from single atoms chelated to the proteins. Intravascular injection of $Fe^{59}$ labelled particles of the type described demonstrated a biphasic plasma half-life with about ¾ of the dose being cleared to spleen, liver, marrow, and slightly to lung over 1–2 hours, but with a substantial fraction of the dose demonstrating a quite prolonged plasma half life of many hours. Each antibody molecule can be used to deliver several hundred or several thousand atoms of the desired nuclide so achieving a high local dose. It should also be noted that binding multiple emitter atoms to a single protein molecule has been known to rapidly destroy the protein—this problem is substantially alleviated by the SMPE particles because the emitting nuclei are up to 100 angstroms distant from the NAM—thus the chance of any electron, positron, or gamma-ray interacting with the targeting NAM is reduced by several orders of magnitude. Methods developed for antibody delivery of $_{39}Y^{90}$ can be applied with a far higher concentration of this nuclide included in a conjugated ferrite. Another treatment problem where these β-emitting ferrites could be useful is in improving the current methods of intra-articular radiotherapy in rheumatoid conditions.

Another means of delivery for β-emitting ferrites is by preparing suspensions of particles in the pre-mix of various tissue glues. After a surgical resection of a tumour, particularly when near an eloquent area of brain, it is often necessary to leave a thin shell of tumour behind on the brain surface. Common practice currently involves the use of various tissue glues to attach a number of radioactive seeds to the residual tumour surface. This method is tedious, leaves no means for removal of the metal without repeat surgery, and causes artifact on future CT and MR scans which makes it difficult to assess the results of therapy. If a colloidal solution of β-emitting ferrite is prepared in a tissue glue component, this can be applied rapidly to the tumour surface, minimizing exposure to the surgeon and operating staff. The particles are biodegradable, so will be resorbed over weeks. This method also permits the use of a variety of different nuclides depending on the energy, penetration, or half-life desired.

Thus viewed from a still further aspect the invention provides a composition comprising a cell adhesion moiety-coupled radionuclide and a tissue glue.

The tissue glue may for example be based on a clottable protein such as fibrinogen; thus for example a glue such as "TISSEEL" (available from Immuno Danmark A/S of Copenhagen) may be used. In two part systems such as this the NAM-conjugated particles are preferably in the protein containing component.

Magnetic properties of the β-emitting vehicle can also be used to help control delivery. This method can be used with or without conjugation with antibodies, and employs the selective catheterization techniques of interventional radiology. An arterial catheter can be introduced near the tumour, or ideally, at a tumour feeding vessel. A magnetic field can be applied by means of multiple external current rings so as to be strongest in the vicinity of the tamour. This can be achieved with the magnetic stereotaxy device described in U.S. Pat. No. 4,869,247. Finally a venous catheter system which is itself strongly magnetized and furnished with a magnetized intravascular filter is introduced downstream of the tumour in one or several draining veins or centrally in the atrium. A highly energetic β-emitting ferrite is slowly injected via the arterial catheter. The progress of the particles through the tumour is slowed by the external field and by any antibodies which have affinity for tumour antigens detectable in the vasculature. After passage through the tumour, the particles are collected on the venous magnetic catheter/filter and so can be removed without exposing the remainder of the body to the radiation. If a positron emitter is used, it is possible to verify the effectiveness of the control of the speed of the ferrite, and if the filtration is effective, then a second stage treatment can be done with ferrite particles including highly toxic alpha emitting nuclides such as $_{78}Pt^{186}$ (K, α4.23 MeV, 3 h). Particles can also be heated with tuned microwave irradiation during their transit for a synergistic diathermy effect.

Turning now to PET image resolution, one of the limitations on scanning resolution is a result of the distance travelled by the positron after the decay event but before electron-positron annihilation. This distance is dependent upon the energy of the characteristic β emission for a given nuclide. The maximum range for an $_9F^{18}$ positron emitted at 0.64 MeV is 2.6 mm while the particles from $_{37}Rb^{82}$ decay emitted at 3.35 MeV travel up to 16.5 mm before annihilation. Along this path (see FIG. 3), the positron loses energy by interacting with the electrons of atoms it passes, causing a variety of ionizations and excitations. Only when most of the kinetic energy is expended does the positron interact with an electron in a matter-antimatter annihilation reaction generating two 0.511 MeV photons travelling approximately 180° away from each other. The residual momentum of the positron at the time of the annihilation imparts some translational momentum to the emitted photons resulting in an angle between the two which differs from 180°. Measurements of this angle reflect the nuclide and the medium in which the energy losses and subsequent annihilation take place.

It has been known for some time that the distance of travel the positron prior to annihilation is proportional to the density of the medium. The density of magnetite is 5,180 kg/m³, just over five times greater than most animal tissues and, according to classical calculations based on electron range measurements, this potentially results in an 80% decrease in the maximum distance travelled by a positron travelling in magnetite as opposed to travelling in tissue. There is an increase in Brehmsstrahlung braking radiation proportional to the effective Z number of magnetite (which= 52), but this only accounts for 1% of energy loss for a population of positrons.

The numbers stated above for travel of the positron before annihilation reflect maxima. In fact during positron emission, the decay energy is divided between the positron and a neutrino and the division is variable, thus resulting in a population of energies. The mean energy of a positron from a given nuclide is about ⅓ of the maximum usually given as the particle energy. The means positron energy from $_{25}Mn^{52}$ is 0.19 MeV and in magnetite this classically would result in a range of about 20 microns if the travel were entirely in magnetite.

However various elements have characteristic positron affinities and these have profound impact on positron lifetimes. Therefore, the classical view of positron range in relation to a general density measurement proves to be a substantial oversimplification.

The positron affinities of a variety of nuclides are included in FIG. 2. It can be seen that by using high affinity nuclides such as lithium in the β-emitter loaded particles, the positron range can be further decreased.

In addition, it has been learned that defects in a crystal can cause trapping of positrons. Defects in $YBaCuO_x$ perovskite crystals are particularly effective at positron trapping even when these materials are not in a superconducting state, however, even mechanical stress defects in metals are fairly effective. There are also effects due to the magnetic field generated by a moving positron and its interaction with the spontaneous field of a material such as magnetite, as well as electron interaction enhancement effects due to the number of unpaired, anti-spin matched electrons from d or f orbitals in the particular spinel used for the particulate shield.

The consequence of these considerations is that it is possible to begin with a crystal seed of a positron emitting nuclide including several thousands atoms of the emitter and then to precipitate a lithium or zinc doped, defected, magnetite shield around the positron emitting core. This shield will cause a very large fraction of the emitted positrons to undergo all of their ionization producing collisional losses within the particle and therefore to annihilate without ever leaving the particle. Those positrons that do emerge from the surface of the particle without being affected by reflection or surface trapping effects will have a greatly reduced energy distribution, travel far shorter distances through tissue, and create far fewer ionizations in tissue per decay event than standard unshielded positron emitters.

The annihilation photons themselves are relatively unaffected by the presence of ferrite as opposed to tissue in their surroundings. Therefore, there will be a very large decrease in tissue ionizations with only a trivial decrease in photon emissions. Further, the photon emissions will all take place far closer to the location of the actual tracer atom, typically within several microns rather than within millimeters and this will result in an improvement in the spatial resolution of the PET scan. Further, the annihilations, as a population, will have lower momentum and this will shift the population annihilation angle closer to 180°, further improving the resolution of the scan.

Where β particles are used for treatment rather than primarily for imaging, this shielding can be used to achieve extremely limited ranges of cytotoxic ionization injury.

The range of the emitted β-particles can be designed to be not much greater than the size of a single target cell, thus limiting effective irradiation to only those cells that actually ingest the particle and taking advantage of the terminal Bragg peak effect which increases the ionization rate for a low energy positron just before annihilation. A short half life emitter could be used to minimize the effect of increasing exposure range with digestion of the coating (which may take days) and multiple treatments could then be carried out. Larger particles can be used without magnetic aggregation by composing the shell of less magnetic nuclides.

A quite different set of particles, e.g. mixed spinels, may be used for spectroscopic tracing and heteronuclear imaging methods. When large percentages of $_3Li$, $_{21}Sc$, $_{27}Co$, $_{25}Mn$, $_{29}Cu$, $_{59}Pr$, $_{71}Lu$, or $_{75}Re$ are introduced into ferrite crystals these become vehicles for delivering large argues of those atoms to a desired site. These elements and their various isotopes have high nuclear resonant receptivity when in the appropriate oxidation state and electron/chemical environment and so the MR machine can be used as a spectrometer to detect the presence of these crystals. Table I lists a series or nuclei with relatively high receptivity. Any high receptivity metal in an oxidation state where electrons do not produce confounding relaxation (e.g. $Mn^{7+}$, $Co^{3+}$) or in which d-electron orbitals are entirely empty ($Sc^{3+}$) or full ($Zn^{2+}$) are particularly amenable. The chemical environment is also important to minimize the effects of quadrupolar relaxation for nuclei with $I>½$.

Nuclei such as $F^{19}$ and $In^{115}$ can be included in compounds which can then be included or embedded in microspheres of latex, protein, polylactic acid or other polymers and these can then be introduced into the axon in sufficient quantity to achieve $F^{19}$ or $In^{115}$ imaging. $F^{19}$ is also quite suitable for labelling a variety of small molecules which are susceptible to effective axonal transport. Compounds incorporating such nuclei may also be included in the coating of metal compound particles with a targeting moiety also present in the coating.

One optimal method in this regard is to use individual chelated scandium atoms where the chelate is conjugated to a small nerve adhesion molecule. By using a very small carrier, it can be assured that the tumbling rate of the scandium atoms is high enough to permit standard MR detection. Where particles are used, the breakdown of the particle inside the neuron will slowly release scandium ions which will become imageable as they are freed from the particle and so begin to tumble rapidly.

Because of the very great abundance of $Na^{23}$, imaging with this nucleus to create a generally useful anatomical image of the patient is readily achieved. Superparamagnetic particles such as ferrous ferrites are effective relaxation agents for sodium and so can be used as axonally transported contrast agent to study nerves upon sodium imaging.

TABLE I

Nuclides with usefully large MR receptivity and their corresponding frequency for 4.7 T MRS. Nuclei in italics (H, F, Na, P) are commonly used in MR spectroscopy but are not readily included in metal oxide particles.

| Nuclide | MR receptivity | Frequency in MHz at 4.7 T |
|---|---|---|
| $_1H^1$ | 1.000 | 200.0 |
| $_3Li^7$ | .270 | 77.6 |
| $_9F^{19}$ | .830 | 188.2 |
| $_{11}Na^{23}$ | .093 | 53.0 |
| $_{15}P^{31}$ | .066 | 81.0 |
| $_{21}Sc^{45}$ | .301 | 48.6 |
| $_{23}V^{51}$ | .381 | 52.6 |
| $_{25}Mn^{55}$ | .175 | 49.4 |
| $_{27}Co^{59}$ | .277 | 47.2 |
| $_{29}Cu^{63}$ | .064 | 53.0 |
| $_{41}Nb^{93}$ | .482 | 48.8 |
| $_{49}In^{115}$ | .332 | 43.8 |
| $_{53}I^{127}$ | .093 | 40.0 |
| $_{59}Pr^{141}$ | .260 | 54.0 |
| $_{71}Lu^{175}$ | .048 | 22.6 |
| $_{75}Re^{187}$ | .086 | 45.6 |
| $_{81}Tl^{205}$ | .140 | 115.4 |
| $_{83}Bi^{209}$ | .137 | 32.2 |

Using a double tuned coil or multiple coil MR system, a high gradient proton image may be made and a selected voxel may then be evaluated at the appropriate MR observation frequency. The presence of the given nucleus with the appropriate spectral appearance confirms the presence of the tracer and also makes quantitation possible.

The sensitivity of these various nuclei for NMR is sufficiently great that actual scandium, or other tracer, imaging can be carried out when delivered quantities are sufficient. This produces a positive image roughly similar in appearance to those resulting from some current nuclear medicine imaging studies. These uses of these nuclides are also applicable to several of their isotopes, both stable and radioactive with some variation in gyromagnetic ratio for the various nuclides. These variations also can provide multiple additional frequency selectable tracers for spectroscopy or heteronuclear imaging.

Using particle types and delivery targeting systems as described above, a different group of metals can be used instead of the β-emitters to achieve the very short range radiotherapy effect. These are a variety of nuclides in which decay is by K-shell capture. Although decay in these nuclides involves collapse of an electron into the nucleus, the resulting vacancy causes effects among the remaining electrons which result in Auger and Coster-Kronig electron emissions. These have extremely low energies and resulting ranges of micron and submicron distances, although several such electrons may be emitted for each single decay event. An optimal nuclide with this behaviour is $_{46}Pd^{103}$ which is a pure K-capture nuclide with a 17 day half life; $_{24}Cr^{51}$ may also advantageously be used.

By analogy with the multiple tracer methods described above for MR spectroscopic nuclides, it is also possible to use various transition or lanthanide metal radionuclides to prepare multiple metal conjugated antibody tracers with the intent of providing them with characteristic gamma emission signatures. Here, the positron emission or MR contrast effect could be used for localization and then the gamma emissions could be evaluated for energy level/frequency. In this fashion, multiple different gamma labels could be distinguished as a means for image based tumour diagnosis by multiple antibody labels.

The particles used generally should be metal compounds capable of precipitation to a stable colloid having a particle size suitable for cell uptake and having a surface capable of being coated with or bound to biochemically useful materials, e.g. carbohydrates or proteins.

As a dense material, ferrite particles are effective X-ray contrast agents. By substituting high Z metals (e.g. elements of atomic number 50 and above, especially sixth period elements) into the lattice, their effectiveness can be further enhanced and the necessary dose thus decreased. This is illustrated by FIG. 4 hereto which shows a CT image of a phantom with wells containing similar concentrations of Mg/Tb and Fe/Fe particles showing the greater X-ray opacity of the former. Wells 11 to 17 contained the following X-ray contrast media:

| Well No. | Material | Concentration (mg/ml) | Field Units |
| --- | --- | --- | --- |
| 11 | Mg/Tb(III) | 30* | 411 |
| 12 | Mg/Tb(III) | 10* | 150 |
| 13 | Fe/Fe(III) | 30* | 101 |
| 14 | Fe/Fe(III) | 10* | 0 |
| 15 | Metrizamide | 33 | 250 |
| 16 | Air | — | −1017 |
| 17 | Metrizamide | 100 | 447 |

*Concentration of the trivalent metal

This sort of technique is particularly useful for axon transport imaging techniques and the evaluation of spinal root compression by herniated disks by CT scanning. Since higher particle concentrations are needed for CT than for MRI, the best uses of this phenomenon include CT scanning of the injection site for confirmation of optimal localization or actual CT guided placement of the injection where necessary with immediate confirmation of location and dose amount delivered. The superior spatial linearity of CT compared to MR, makes CT preferable for stereotactic placement tests. CT is also effective for these agents at the concentrations achieved in lymphatics after subcutaneous or intramuscular injection.

When an alternating magnetic field is applied to a magnet, a number of resonant interactions can come into play which can completely destroy the net magnetization. The main resonance is to do with the precession frequency of the dipoles around the main axis. There are also resonance effects in bulk magnet to do with movements of the Bloch walls between domains as well as with the size of domains. In a sub-domain sized superparamagnetic particle, the principal determinant of resonant behaviour is generally the intrinsic flipping frequency due to the temperature, particle size, and compositional anisotropy. Exploration of the impact of radiofrequency signals on the resonant behaviour of superparamagnetic particles of well defined sizes is suggestive of numerous useful effects.

For more specific separation of the particles according to resonant behaviour, a chromatography column or a very long coil of narrow bore tubing can be placed inside a high field magnet such as a 2.0 Tesla MRI magnet, and the column then surrounded by an elongated solenoid coil with various switchable capacitors, resistors, and inductors attached. This apparatus can be used to subject the chromatography column to a series of selected radiofrequency fields. During the irradiation of the column with a particulate field frequency, those particles that are relatively demagnetized at that selected frequency will commence moving down the column while the remainder of the assortment of particles will remain fixed in the external magnet's field. That fraction of resonant selected particles is collected, and then the frequency of the applied field is changed to permit elution of a second resonant selected fraction, and so on in this fashion until a series of different resonant selected fractions are collected. The demagnetization can be achieved either by pulsed RF irradiation which flips the coherent particle axis into a transverse orientation, or, more efficiently, by introducing sufficient energy to induce non-coherent flipping of sub-unit dipoles.

By the use of these alterations in size, composition and intrinsic resonant magnetic behaviour, a series of particles is produced with differing resonant behaviour which can optimize them for use in an MRI device of a given field strength and proton Larmor frequency. Also, by producing highly purified resonant engineered particles in this fashion, it becomes possible to produce the phenomenon of Selective Radiofrequency Flipping Alteration (SRFA). The resonant engineered, purified particles are subjected to a selected radiofrequency signal (by means of additional coils around the imaging subject) and sufficient energy is introduced to overcome the coherent alignment of the crystalline sub-units with the applied external field. This results in an effective demagnetization of the particles and a sudden reduction of their contrast effect in an MR image.

Two MR images may then be collected a few hundred milliseconds apart, with the first being contrasted and the second being non-contrasted. These two images are then subtracted from one another by the computer and a subtraction image results. This fields a "contrast neurography" by which only the nerves and any other tissues with high concentration of the particles are seen. The process can be repeated at a different appropriate frequency for each type of resonant tuned particle injected. In this fashion, several different nerve roots could be visualized, each in a different image if their respective muscles of innervation had been injected with different resonant tracers. The lymphatics will collect all the tracers and so will be subtracted from all the images.

This SRFA subtraction technique may also be applied to other ferrite MRI contrast methods such as antibody based labelling of tumours or infection sites wherein several different antibodies could each be attached to a different resonant particle group. Then by using an apparatus that can generate multiply tuned frequencies within the MR magnet during imaging to serially change the frequency at which the subtraction image is obtained, the external images can be used to determine which antibody is adhering to the area of interest.

Another distinct use of these resonant modifications is to prepare particles with frequencies in the microwave range. Such particles experience mechanical vibration and hence heating when subjected to resonant tuned microwave energy. In this method, the particles would be transported into areas of spinal cord injury where the development of scar prevents the regeneration of injured spinal cord tissue. In research work, this localized heating phenomenon might be used as a means of inhibiting spinal cord scar formation. This effect may also be applied for selective tumour diathermy. Intramuscular injection at various sites with different resonant particle frequency types at each site will permit rotation of microwave heating frequencies so that only the tumour site will be stimulated by all the signals.

From the above, it will be appreciated that the method of the invention provides an entirely novel means of pharmaceutical distribution which involves the entrainment of a well known physiological phenomenon called axonal transport. A central feature is that the total body distribution after intramuscular injection of the pharmaceutical agent quite unexpectedly yields dramatically high intraneural concentration relative to other tissues. This differential in body/nerve concentration permits the use of this route with relatively small amounts of pharmaceutical agent to achieve nerve based imaging and treatment effects.

Insofar as the method of the invention is concerned, it may be helpful to review the background to the present understanding of axonal transport processes.

A neuron which innervates a muscle in the human foot is an enormous single cell (see FIG. 5) nearly three feet in length whose nucleus in the spinal cord must manage chemical metabolic events taking place far away in the axon terminus. The supply of newly synthesized proteins, membrane vesicles, and organelles such as mitochondria is accomplished by first producing these items in the cell body, then transferring them along the axon at rates of up to a meter per day. This 'anterograde' flow could result in a tremendous accumulation of material in the axon terminus unless compensated by a return or 'retrograde' flow at similar rates and by a similar mechanism.

Although there are various rates and mechanisms of axonal transport, the fast anterograde and retrograde flows (see FIG. 11) are carried out by motile proteins (kinesin and dynein respectively) which drag molecules and vesicles along the microtubules of the axoskeleton. The materials transported include not only structural and metabolic molecules, but also molecules sampled from the external environment of the axon terminus which are passed back up to the neuron cell body to inform it of the environment. Such signals include various trophic or growth factors originating in cells near the axon terminus which are endocytosed by the axon, encapsulated in lipid vesicles, and various trophic or growth factors originating in cells near the axon terminus which are endocytosed by the axon, encapsulated in lipid vesicles, and then passed up to the cell body for processing or analysis via the axonal transport system (see FIG. 12).

The rate of transport of a given substance is independent of electrical activity within a neuron but does vary with the type of molecule being transported. Anterograde axonal transport has a major fast and a slow component. The slow component is divided into "slow component a" and "slow component b" at rates of approximately 1 and 3 mm/day respectively. These slow components apparently reflect gradual structural repair and replacement of the subunits of the cytoskeleton and are not involved in the fast components important for tracer studies.

The fast component of transport demonstrates distinct maximal rates for anterograde (300–400 mm/day) and retrograde (150–300 mm/day) transport and some rates up to a meter/day have been reported. The maximal rates of transport apply to small membrane vesicles. Further, there are a variety of "waves" or distinct sets of slower transport rates exhibited in characteristic fashion by various molecules.

All of this movement is ATP and calcium dependent. The metabolism involved is local, i.e. mitochondria bound to the axolemma as well as mitochondria being transported on the microtubules use glucose and oxygen absorbed through the cell membrane along the axon to generate ATP locally.

The existence of axonal transport (or 'axoplasmic flow') has been known for over 40 years and it has been known for twenty years that certain foreign materials injected into muscle would be endocytosed (swallowed up) by the axon terminus and then subsequently be detectable in the neuron cell body; however, until the developments described herein, all methods of detection have required lethal interventions, generally requiring the killing of the experimental animal with subsequent specialized tissue processing.

A series of relatively non-specific substances for uptake were tried including Evans-Blue stain conjugated to albumin and also horseradish peroxidase (HRP) enzyme, and radiolabelled amino acids for anterograde labelling. The principal of improving specificity and uptake efficiency of a histologically identifiable tracer was taken further by Schwab (Brain Res. 130: 190–196 (1977)) who attached nerve growth factor (NGF) to HRP. It was also Schwab who showed that a plant lectin called wheat germ agglutinin (WGA) was an excellent nerve adhesion molecule and again Schwab who introduced the use of viral fragments and toxins as labels (see Brain Res. 152: 145–150 (1978) and J. Cell Biol. 82: 798–810 (1979)).

WGA conjugated to HRP was later suggested as a tracer and this one agent has been the predominant agent of choice in many hundreds of subsequent studies involving axonal transport. The conjugation to some post-sacrifice visualization moiety such as HRP permitted the use of a chromogen histochemical staining reaction. Other means of visualization of tracers included autoradiographic histology or immunocytochemical techniques.

Once endocytosed, WGA-HRP conjugates are found in Golgi/Endoplasmic Reticulum/and Lysosomes (GERL) and are transported at a slower rate than HRP alone. Many of the agents which employ plant lectins, viral toxins and surface fragments, and some anti-synaptosomal antibodies as targeting moieties are taken into the cell by "adsorptive endocytosis".

There is also a route called "transcytosis" taken by unconjugated lectins. These molecules also bind to receptors before endocytosis but are then transported within the cell without being first introduced into lysosomes. This mechanism has also been shown with a monoclonal antibody ("192-IgG") raised against an NGF receptor on pheochromocytoma cells and has made it possible to show that the NGF molecule binds to the receptor protein and that the entire complex is then transported up the axon to the cell body.

Another interesting ligand/receptor complex involves $[H^3]$-Lofentanil and the opiate receptor which are endocytosed and transported by sensory neurons. PET studies with $[C^{11}]$-carfentanil have been used to assess the general distribution of opiate receptors, but this approach has never been tried as a means of tracing selected tracts via axonal transport in humans. Similar studies with GABA, D-aspartate, dopamine, norepinephrine, and serotonin have shown that uptake and transport of neurotransmitters is a widespread phenomenon in the CNS as is the transport of receptors.

Acetylcholinesterase uptake and transport has been studied for many years because of its ease of use as a histochemical marker. Other studies have demonstrated transport of a wide variety of substances including Vasoactive Intestinal Polypeptide (VIP), cholecystokinin, substance P and somatostatin, neuropeptide-Y, and adriamycin. These types of tracers have sometimes been introduced by intravenous injection with subsequent uptake by neurons as well as by actual tissue injection in or near the neurons of interest.

Yet another set of studies has involved neurotrophic viruses such as Herpes Simplex, poliovirus and bacterial neurotoxins, e.g. tetanus toxin. Of the various tracers, tetanus toxin is the most effective for "transsynaptic" labelling in which the next neuron in a synapsing series is also labelled. It is possible that killed vaccines, or toxoid versions of these could be useful. As with physiologic molecules, they offer high avidity for the neuron and their transport kinetics have been previously studied.

Another important phenomenon is transneuronal transport wherein tracer is apparently extruded back onto the cell surface after transport thus acting to produce a sort of second injection at the next synapse in the chain (see Gerfen in Exp. Brain Res. 48: 443–448 (932)). Tetanus toxin appears to move in a specifically transsynaptic fashion, but WGA and WGA-HRP are found in glia after anterograde transport of WGA-HRP, and synaptic structures need not therefore be involved.

Another area of advance has been in the use of particulate tracers. Olsson in Neurosci Lett., 8: 265 (1978) suggested the use of a non-specific very small particulate iron-dextran complex in which the iron was in gamma iron oxide form and in which post-sacrificial detection involved microscopic study after chemical staining for iron. Other important particulate tracers used for histological light and electron microscopy have included a large protein with a ferritin core, 1–10 nm non bio-degradable colloidal gold particles and colloidal fluorescent particles some 15–20 nanometers in diameter. Latex microspheres with fluorescent labels and ranging from 50 to 200 nanometers in size have also been used. However, there has been a continuing belief that larger particles can only be transported after neuronal injury and most of the particle studies have involved transport between locations in the central nervous system after traumatic needle injection into the brain substance (see Colin, Brain Res. 486: 334–339 (1989))

Detection or transport in living neurons has been accomplished in several ways. Thus for example, the neuron may be rapidly removed intact from the killed animal and placed over a series of Proportional β-particle counters to detect the passage of a radioactive tracer pulse along the axon. It is also possible to directly observe the movement of organelles along such excised neurons via microscopic video interference contrast techniques.

There is however no prior art for in vivo imaging use of nerve adhesion molecules coupled to clinically imageable a tracer molecules which does not involve direct inspection of neural tissue. Further there is no prior art for any entrainment of axonal transport to achieve desired distributions of any actual pharmaceuticals for human or veterinary therapeutic use. Axonal transport has been much studied as a physiological process (analogous to the study of DNA prior to the advent of industrial biotechnology) and it has been used extensively for studies in which the delivered agent is effective only after the death of the organism (as in histology) or achieves its effectiveness only through the killing of nerve cells which transport various toxins. However, there are no prior clinical uses, or uses in which the effect is achieved in a living animal or human with intended diagnostic or therapeutic rather than neurotoxic effects.

Very recently (after the priority date hereof), Brady SMRM 10:2 (1991) verbally reported transport of MR detectable particles after direct injection into the sciatic nerve; however he exhibited only an image of transport after the completely severed sciatic nerve was soaked in a gel with ferrite particles. Ghosh in SMRM 10:1042 (August 1991) similarly reported evidence of transport of ferrite particles after direct pressure injection into the brain of a frog, although no MR detection was achieved. Neither taught how pharmaceutical use of axonal transport could be achieved since these techniques involved irreparable destruction of vital neural tissue. Intraneural injection is destructive of the nerve at the site of needle puncture and causes forced flow of tracer in the nerve sheath which may actually mask evidence of actual axonal transport. Madison in Brain Res. 522: 90–98 (1990) also reported pressure injection of latex nanospheres into the brain wherein the spheres were used to deliver toxic agents for the killing of neurons after subsequent photoactivation. These reports can, indeed, be taken as evidence of the non-obviousness of the non-destructive techniques described herein.

Non-destructive administration of toxic anthracycline antibiotics has been reported, but this was done to study the chemical nature of the neural uptake process and the fluorescent effect of the agents rather than to achieve any therapeutic effect, and the agents concerned were neurotoxic (see England in Brain 111: 915–926 (1988) and Bigotte in Neurology 37: 985–992 (1987)).

Unlike any of these previous reports, the agents described herein may be introduced by techniques which do not involve the destruction of neural tissue and which then achieve a pharmacologic effect which does not require any toxic injury to neural tissues. By delivering particulate carriers it becomes possible to deliver types of pharmaceutical agents which would be irreparably damaged by direct chemical conjugation to a NAM or on break up of its direct NAM-conjugate within the cell. Instead the NAM is coupled to the particle and the drug is included in the particle or in the particle coating. Further, the use of particulate drug carriers permits the introduction of large numbers of molecules of the pharmaceutical agent with each endocytotic event thus yielding a 100 fold or up to one million fold increase of uptake efficiency per NAM. This amplification effect may be crucial to achieving pharmacologically efficacious doses in many situations. The methods of administration for these beneficial diagnostic and therapeutic uses include topical, intravenous, intrathecal/intracisternal (cerebro-spinal fluid), sub-cutaneous, intradermal, intranasal, eyedrop, or bladder irrigation methods, but intramuscular administration is to be preferred.

The agents described herein differ from all previously used axonal tracers in that they include agents capable of controlled administration by safe intramuscular injection with non-toxic substances and of achieving whole body distributions which permit their useful observation by various types of non-invasive imaging modalities. The agents may be biodegradable, safe for clinical use, and act to reveal various human disease conditions which cannot be adequately demonstrated by existing techniques.

Previous uses of axonal tracers have been concerned with optimizing the degree of post-sacrificial staining of the neuron cell body in brain or spinal cord. It has not previously been evident that useful concentrations and distributions of clinically applicable tracer materials could be achieved.

However, this set of agents is based on the discovery that when a nerve adhesion molecule which also has affinity for markers on the muscle cell surface is used, the injected material has very minimal spread from the site of intramuscular injection. In consequence, a relatively large amount of the substance is transported into the nerve while relatively little spreads throughout the body. The initial distribution assay results with animal studies using $^{125}$I labelled WGA are shown in FIG. 13. This showed that the concentration in peripheral nerve was up to ten times higher than in any other tissue excluding the site of injection. The injection site could be masked out of an image so this suggested that the distribution after intramuscular injection might be consistent with imaging.

However, although the concentration in the nerve was 10 to 50 times higher than for example in surrounding muscle, the total volume of the nerve relative to the volume of surrounding tissue was quite small. Thus, only an imaging technique which could collect signals from a very small 'voxel' size could successfully recover the signal. At this relative concentration, simple labelling of a small molecule or protein with a gamma emitter for SPECT detection would be inadequate. Substitution of a relatively long half life positron emitter ($^{124}$Iodine) for the $^{125}$Iodine would provide nearly adequate voxel size but would involve substantial spread of radioactive iodine through the body. Other relatively long half life positron emitters presented similar problems.

The use of a magnetic resonance small molecule contrast agent such as gadolinium-DTPA (diethylenetriaminepentaacetic acid) required the introduction of a very high concentration into the nerve and this amount was beyond what could be achieved. However, by synthesizing a particulate magnetic resonance contrast agent based on a ferrous ferrite core, coated with dextran and conjugated to WGA, a series of useful solutions to the problem were revealed.

Very surprisingly, the distribution results with even a crude preparation of this type of agent which was not affinity purified were up to an order of magnitude better then the previous results with iodinated WGA ($I^{125}$-WGA). The concentrations in nerve were 50 to 100 times higher than in any other tissue excluding the injection site and local lymph nodes (see FIG. 14). However, unlike the $I^{125}$-WGA result, the concentration in the nerve was actually considerably higher than in the neuronal cell bodies of the spinal cord. This distribution will often be advantageous since most of the metabolism of the particle carrier will take place in the nerve and surrounding Schwann cells while passing mostly only smaller molecules on to the cell body in the central nervous system. Using highly purified, affinity specific product, exceedingly desirable distributions result, with effectively nil detectable agent in any tissue, but for traces in liver despite very good intraneural concentrations. Non-specific particles eluted from the affinity column without using the affinity eluant, but injected in identical concentration and amount yielded no evidence of axonal transport. Only particulate tracer conjugated to affinity purified NAM entered the nerve in high concentration.

Using ferrite doped polyacrylamide gel phantoms, it was observed that this preparation could reduce the $T_2$ relaxation time of nerve below 30 milliseconds if the intraneural concentration of iron were greater than 5 micrograms/ml. The injections with the crude preparations actually achieved concentrations in nerve of over 50 micrograms/ml (see FIG. 15). An experimental imaging magnet was modified to carry out confirmatory tests which permitted an image resolution with voxel size of only 1/10 of a millimeter and using this system it was possible to measure and callibrate nerve contrast distinguishing the tibial nerve of the injected from the uninjected leg (see FIGS. 16 to 20).

Nerves which were subsequently excised and measured for exact $T_2$ in the magnet conformed the desired 50% reduction of $T_2$. Electron microscopy confirmed uptake and transport of the intact particles (see FIGS. 21 and 22) and the $T_2$ results showed that their rate of metabolism in the nerve was slow enough for their superparamagnetic properties to be maintained until the time of imaging. The electron microscopy also revealed that most of the particles were being passed out of the neuron into the endoneurial fluid surrounding the nerve. This export of the tracer was accomplished by the paranodal complex at the nodes of Ranvier (see FIG. 10). From the endoneurial fluid, the particles were being attached to the outer surfaces of the Schwann cells which surround the axon due to affinity of the WGA label for the Schwann cell surface.

In parallel with these studies, a positron emitter, $^{52}$Manganese, was used to make spinel moderated positron emitters and these were prepared in gels to duplicate the concentrations achieved with ferrous ferrites. This study confirmed the physical prediction that with as low as 25:1 contrast ratio, a 1 mm object could be readily detected and distinguished from a larger object simulating a lymph node one centimeter away (see FIG. 23). Thus, the SMPE version of the agent was shown to be adequate for PET observation of the transported agent. These distributions also permit the use of SPECT labelled crystals for nerve imaging studies in humans.

The delivery of particulate pharmaceuticals by the intraneural route is an entirely novel means of drug administration. The largest number of drugs in current use depend in some way upon the bloodstream to achieve their distribution. This vascular dependence includes not only drugs given by intravenous or intra-arterial routes, but also most orally administered drugs which must be absorbed into the bloodstream to reach target tissues, most intramuscularly administered drugs which are absorbed by the muscles blood vessels, many inhaled agents, most intranasally applied drugs, some rectally administered drugs such as paraldehyde, and many topically administered agents such as transdermal nitroglycerine. There are, however some drugs which are delivered into and distributed by the cerebrospinal fluid (intrathecal route), some oral drugs which are not absorbed (kaolin, oral vancomycin), a variety of topical and intravaginal agents, and some administered percutaneously for local effect or intraarticular effect such as local anaesthetics, and locally administered steroids.

Various new drug forms and methods of use described below involve delivery via an intraneural route. Access to this route may be obtained by oral ingestion, topical, intra-articular, intrathecal, intravenous and, preferably, intramuscular administration. However, common to all these new methods, is that the dosing and active site of the agent is determined by a route which involves endocytosis by nerve endings with subsequent transport to a different and distant part of the neuron.

In some experimental studies, various agents for transport have been introduced by intraneural injection or by application to the cut end of a severed nerve. In these methods, the 'blood brain barrier' due to the perineurium is traversed by mechanical injury, and much of the uptake of tracer is due to direct presentation at cut nerve endings where specific nerve adhesion molecules may be irrelevant. The intramuscular technique (and also the intravenous application) depend upon the natural defect in the perineurium which occurs at axon terminus. Thus the blood brain barrier is naturally incomplete at this site so that tracers reversibly adherent to muscle or emerging from small blood vessels passing near neuromuscular synapses can present a variety of molecules and particles directly to the neuronal cell surface for uptake after specific adhesion to the neuronal cell surface at the axon or dendrite terminus.

The site of injection or administration will preferably be determined only by knowledge of the nerves which project to that site. For example, a pain in the large toe will be known to the neurologist to involve the dorsal root ganglion of the fifth lumbar nerve root. He will then choose an injection site somewhere in the dermatome or myotome served by that nerve root in order to label the part of the nerve he believes to be impaired or to deliver, for instance, a pain medication to the ganglion or spinal cord dorsal root entry zone connected to the fifth lumbar spinal nerve root. For radionuclide imaging as well as for drugs where systemic spread is to be minimised, it is particularly important to be able to achieve high uptake by neurons per unit amount injected and to minimise spread away from the injection site.

When imaging is done, the image will preferably be collected at high resolution of a site which is different from the site of injection, but which is connected to the injection site by a nerve. The imaging will also be done at a time which allows the agent to be transported the necessary distance from the injection site to the active or imaging site at a natural rate related to the size and type of the injected intraneural drug.

Where the intraneurally administered agent is a negative ($T_2$-reducing) MRI contrast agent, contrast may be further enhanced by administration of a positive MRI contrast agent (e.g. Salutar's SO41, Squibb's Pro-Hance or of course Schering's Magnevist) so as to distribute into the tissues surrounding the neuronal pathway under investigation. It has been shown that STIR and CSI (Chemical Shift Imaging) sequences help sharply distinguish nerves from any surrounding fat and so emphasise the impact of the contrast agent. For example a STIR (Short Tau Inversion Recovery) with tau =160 ms, $t_e/2$=30 ms and a long $d_1$=2 seconds to decrease saturation will accomplish this desirable effect to best demonstrate the axonal imaging effect of ferrite tracers.

The nerve adhesion molecules used to initiate the uptake and transport of the pharmaceutical agents used according to the invention all have in common with each other some tendency to promote uptake by neurons. Some molecules with no particular affinity may be taken up and transported inefficiently by neurons. However, molecules which interact with and bind to specific cell surface markers or receptors on the nerve ending of the selected nerve type are far more efficient and are preferred. An additional degree of efficiency can be obtained when the compound also has some affinity for the cell surface of muscle cells, since this will promote the depot effect at the injection site and decrease the tendency for the agent to diffuse away or be carried away by the bloodstream prior to uptake by the neuron. However, in some applications, such as SPECT and PET imaging, it may, in fact, be desirable to encourage such washout by the bloodstream to minimise radiation dose to the muscle after a brief period of uptake by the nerves innervating that muscle.

For investigative work involving animals, wheat germ agglutinin (WGA) can be used to provide specificity for active uptake and transport. However, there are a wide range of nerve adhesion molecules which can be used to cause selective and active adsorptive endocytosis into nerves. This class of nerve adhesion molecules includes:

1) Anti-synaptosomal monoclonal (and non-monoclonal) antibodies which are purified or generated based upon their affinity for nerve membranes. These can be made by using crude nerve homogenates and then testing for endocytotic efficacy in cultured neuroblasoma cells or by direct measurement of uptake of radiolabeled forms after intramuscular injection in laboratory animals. These agents may involve entire antibodies of, preferably, the fragment of the antibody responsible for recognition without the $F_c$ region. Similar considerations apply for antibodies to dopamine-beta-hydroxylase.

2) Various growth factors such as nerve growth factors, epidermal growth factors, insulin-related growth factors and other proteins and peptides in this functional category which are known to have or discovered to have efficacy at causing the neuronal uptake of themselves and of other agents with which they are conjugated.

3) Lectins of various sorts which are proteins having a high degree of affinity for particular carbohydrate and other types of cell surface markers. This is meant to include both plant lectins as well as various endogenous vertebrate, mammal, or human lectins as are known or may be discovered.

4) Fragments of neurotrophic viruses such as Herpes simplex, pseudorabies virus or poliovirus or proteins or other markers from the viral coat responsible for their highly efficacious uptake and transport. These fragments or inactivated whole viral particles, or cloned and produced copies of the crucial proteins are of particular interest for trans-neuronal transport.

5) Fragments of bacterial toxins such as the B-chain of cholera toxin and non-toxic fragments of tetanus toxin such as the C fragment as well as modified versions or cloned portions of other safely administered proteins with high neural affinity.

6) A wide variety of peptides and small proteins such as endorphins, vasoactive intestinal polypeptide, calcitonin gene-related peptide, cholecystokinin, substance P, somatostatin, and neuropeptide Y or the relevant portions of such peptides for the encouragement of neuronal uptake and transport.

7) Enzymes which are selectively endocytosed for synaptic recycling purposes such as acetylcholinesterase and dopamine beta hydroxylase or portions of these enzymes which are effective at inducing neuronal uptake.

8) various cell adhesion molecules including peptides, proteins and various simple and complex carbohydrates which are effective at promoting neuronal uptake and transport of conjugated pharmaceutical agents.

9) Neurotransmitters and neurotransmitter analogs such as GABA, D-aspartate, dopamine, norepinephrine, serotonin, and benzodiazepine drugs which can be so constructed as to maintain their efficacy in promoting transport after the conjugation to pharmaceutically useful agents.

Two optimal nerve adhesion molecules for most applications are transferrin and β-nerve growth factor depending on whether primarily mixed or primarily sensory nerves are to be imaged; however, various other molecules may be optimal for particular sorts of pharmaceutical tasks.

These proteins and other nerve adhesion molecules can be attached to the therapeutic, prophylactic or diagnostic moiety or to the coating (e.g. dextran coating) thereof by various methods including a periodate oxidation reaction carried out under mild conditions which does not affect the oxidation state of ferrite crystals or the binding affinity of the targeting molecule. Other binding reactions include carbodiimide binding, glutaraldehyde binding, biotin/avidin linking, or noncovalent coating with the molecule of interest. Metal oxide particles provide a core of useful size which can be securely coated by a variety of types of agents under mild, non-denaturing conditions—they are therefore useful as a particle seed even when their special metallic or magnetic properties are not relevant to the task at hand.

All of the above conditions may be optimized so as to use this new drug administration method to efficiently deliver a specially designed pharmaceutical to a specific and preselected location within the nervous system. The sites will include peripheral nerves along their continuous lengths, sensory ganglia, autonomic ganglia, spinal cord, and brainstem or the olefactory tract system upon intranasal administration. When the route of administration is intrathecal, or topically upon the brain during surgery or in the brain during open surgery or during stereotactic surgical procedures, then a wide range of sites within the central nervous system can be reached. In these cases of direct application in the brain, it may be the purpose of the agent to be transported to a surgically inaccessible site by axonal transport from a surgically accessible site, or in any case to a site different from the site of application. This may also be used to demonstrate a successful incorporation of grafted neural tissue which will become capable of transporting included agents from the graft to distant sites. It will occasionally be helpful to achieve transport with a small molecule such as an amino acid or protein labelled with e.g. a positron emitting nuclide; however, in many of the applications, the preferred type of agent will include a particle which is up to 50 nanometers in diameter and may contain many atoms, crystal subunits, or molecules of the active ingredient for diagnosis or therapy.

The exact relation between particle core size and resulting $T_2$ relaxivity per microgram or iron is dependent on a variety of factors in the particle synthesis and upon the biochemical environment in which the particle must exist prior to imaging. Shen in SMRM 10: 871 (1991) reports a relation between relaxivity and crystal size which greatly favours the use of the largest possible particle. Relaxivity data on particles produced by the inventor showed values of up to $4.0\times10^5$ $sec^{-1}M^{-1}$ which are greater than those reported by Shen and are consistent with this trend. Thus, an optimal relaxation effect per amount of iron to be cleared by the nerve may be achieved with the largest particles endocytosed and transported efficiently.

When more diffuse effects are desired, an injection into the bloodstream or into the cerebro-spinal fluid can be used to cause uptake by a specific type of neuron wherever it contacts the fluid. However, for specific delivery to an individual peripheral nerve, the intramuscular technique will be preferred.

The usefulness of the intramuscular administration derives from the fact that individual axons which enter a muscle divide multiply and fan out to innervate numerous individual muscle cells making up a 'motor unit'. Such a motor unit is a group of muscle cells which fire simultaneously whenever their shared axon delivers a depolarization signal. Due to the dictates of muscle energetics and control mechanisms, the cells of a unit are generally scattered through a muscle rather than concentrated in a single area. Thus an injection at any one site will usually be near the axon termini of a large number of different motor units (see FIG. 7). This presents the injectate with a relatively large axon terminal surface area and provides access to a mix of axons distributed evenly through the incoming nerve. Additionally, because all muscles have a rich sensory supply to muscle spindle tension, length, and rate receptors, distributed through the muscle, there is simultaneous access to sensory and to motor fibers (see FIG. 8).

When $I^{125}$-NGF was injected in muscle, high intraneural concentrations were achieved because of uptake by the various types of sensory endings in the spindle organs of the muscle.

Intramuscular injections with intraneuronal pharmaceuticals present no greater risk of nerve injury than any other sort of routine intramuscular injection. However, it is well documented that any fine axonal branch which is injured causes no lasting muscle impairment. This is because of the short distance of regrowth and the tendency for axon terminal branches to recolonize any denervated muscle cell. It should be noted that although injury to some axonal branches may occur, the distribution of tracer in nerve and in cell bodies upon histologic inspection of the spinal cord is consistent with uptake by intact cells rather than by any important contribution from uptake by injured cells.

There are a wide variety of clinical uses for an imaging method that labels nerves, traces connections and assesses pathologic changes in neurons. Axonal transport continues in crushed or compressed nerves with accumulation of transported substances both proximal and distal to the site of injury and so could be used to mark the location of the pathology—inside or outside the spinal cord. Experiments conducted by the inventor confirm the accumulation of $^{125}$I-labelled WGA distal to compression and ligation sites at concentrations just moderately greater than in distal nerve but much greater than in proximal nerve, with relative concentration ratios compatible with image based location of injury sites.

Imaging of axon transport may be achieved using agents in which various nerve adhesion molecules including proteins capable of inducing active endocytosis by axon termini are bound to coated mixed metal spinel particles or other particles or diagnostic markers optimised for the various techniques discussed herein or to such small molecules or detectable nuclides as are suitable to the imaging method of choice. After administration by an appropriate route, such as intramuscular injection, the compounds are caused to enter and to travel along within the nerve axons. The alteration in imaging contrast progresses along the nerve from the axon terminus towards the cell body (or vice versa) unless it is impeded by a nerve compression or crush. In an incomplete injury, the tracer molecule will accumulate at the blockage point. The rate of accumulation will be affected by such phenomena as turnaround transport at the compression site and by depression of rates of transport in more severe compressions. In general, the administration of the agent is intended to produce a change in relative concentration of the agent which will distinguish axon contrast proximal and distal to the site.

The rate of progression of the contrast particles is determined in part by their size and by the particular protein used to provide their specificity. Attachment to nerve growth factor as opposed to other cell adhesion molecules will take advantage of specialized transport pathways. Various specific neural pathways can be studied by using e.g. antibodies to the opiate receptor or to other receptor/neurotransmitter systems or even to non-receptor synaptosomal antigens as the protein portion. However, for a given adhesion protein, the rate of progression of the particles along the axons will be altered in various neuropathies and other diseases affecting nerves.

Intramuscular injection of 10 to 100 microliters of concentrated particles (5–20 mg Fe/ml is achieved by use of Amicon Centriprep-30 concentrators or by reconstitution after freeze drying) is adequate to cause transport which can then be imaged. Much smaller injections can be made into central nervous system tissues under stereotactic or image based guidance in order to observe transport between central structures or even for drug delivery. Also, using proteins which encourage transneuronal transport, a peripheral muscle injection can be used to cause transport along the spinal cord and so help to diagnose the severity of spinal cord injuries.

The various types of inorganic particles described herein can all be attached to nerve adhesion molecules for the study and evaluation of the nervous system by means of axon transport. These materials include 10 to 50 nm ferrous ferrite dextran coated particles, resonant tuned superparamagnetic particles, enhancement agents for Overhauser MRI (see for example WO-A-91/12024), multiple nuclide particles for MR spectroscopic and multiple nuclide MR imaging, positron emitting particles, gamma emitting particles for SPECT, proteins or small molecules labelled with positron or gamma emitting nuclides, shielded positron emitting particles, high Z substituted particles for CT X-ray contrast with poly-energetic or selective mono-energetic imaging.

Additional types of agents for imaging include paramagnetic metal chelates of polychelants (e.g. poly-lysine gadolinium-DTPA 40 which uses the macromolecular/particulate aspects of uptake to introduce groups of paramagnetic nuclei (40 Gd atoms per molecule) (see EP-A-305320, EP-A-357622, EP-A-355097, EP-A-331616, WO-A-90/12050 and WO-A-90/13256)), liposomes containing superparamagnetic or paramagnetic MR contrast compounds, and air-containing albumin spheres typically used for ultrasound contrast which can introduce susceptibility based MR contrast effects into nerve with a minimum of foreign material to digest. Also, fluorescein or other biocompatible fluorescent molecules conjugated to a nerve adhesion molecule or conjugated to dextran coated ferrites can be injected to permit confirmation of nerve location by a neurosurgeon during an operation. Spinal Root Compression from Herniated Lumbar Disk: The axon transport of ferrites or other particulate agents according to the invention can be used instead of myelographic X-ray, unenhanced X-ray CT (computed tomography), electromyography (EMG), nerve conduction velocity (NCV) studies and somatosensory evoked potential (SSEP) to evaluate back and leg pain to check for sciatica. The patient receives a very small intramuscular injection of the agent at their doctor's office one to three days prior to the imaging session. The agent then travels up the nerve, and a moderate contrast change develops in the nerve along the path of transport. However, if there is any compression of the nerve, the contrast agent piles up "upstream" of the obstruction. An imaging study is then obtained.

The resulting scan would show the precise location of the nerve root compression, and, by the amount of contrast agent piled up at the nerve compression site compared to the amount that passes, the severity of the compression could be assessed.

Unlike myelography, there is no lumbar puncture, no need for hospitalization, and if the MR version of the imaging agent is used, no need for any X-ray exposure. A single study shows the surrounding anatomy, confirms the actual nerve compression rather than related nearby problems that might or might not cause actual compression, and demonstrates the physiologic effect of the compression through demonstration of interference with axonal transport. This is particularly helpful in MR imaging since the nerve is often compressed against bone and the bone itself does not show well on MR. The use of MRI in the diagnosis hindered hereas been greatly hindered heretofore because this imaging technique reveals herniated disks in up to 60% of normal asymptomatic individuals. What is needed is a means of showing both that there is a herniated disk and that it is actually causing a nerve compression since surgical decision making requires knowledge of both of these findings. There is no special risk of failing to diagnose far lateral disc herniations, and there is no need for uncomfortable and unreliable EMG, NCV, or SSEP studies.

Cervical Radiculopathy: Nearly identical arguments apply to the condition call "cervical radiculopathy" in which an intervertebral disk or bony spur in the neck pinches a spinal nerve causing hand, arm, shoulder and neck pain. Myelography in this condition is even more dangerous since it involves placing a needle in the high cervical spinal canal. A nerve injury from a needle in the lumbar region will only exacerbate sciatica, but a spinal cord injury from a cervical puncture can cause death or quadruplegia.

By making myelography unnecessary in the assessment of sciatica and cervical radiculopathy there would result a very large overall reduction in procedure costs and radiologist's time, and a saving of tens of thousands of hospital admission days.

Nerve Entrapment Syndromes: There are a wide variety of nerve compression syndromes of which the most well known is carpal tunnel syndrome. In that particular condition, a gradual thickening of ligaments in the wrist causes pain, muscle wasting, numbness and weakness in the hands affecting hundreds of thousands of patients each year. There are some eight or ten other similar conditions affecting various nerves in various locations about the body (thoracic outlet, supracondylar/Struthers ligament, anterior interosseous and posterior interosseous/arcade of Frohnse, cubital tunnel/ulner palsy, ulnar compression in the wrist/Guyon's canal, suprascapular, meralgia paraesthetica/lateral femoral cutaneous, saphenous, peroneal, and tarsal nerve compression syndromes).

These conditions are exceedingly difficult to confirm. The only reliable method for carpal tunnel is EMG and many of the other conditions must be inferred from the clinical examination of the patient with subsequent "blind" surgical exploration. In fact many depressed patients filling up the waiting lists at pain clinics and consuming a variety of non-efficacious medications actually have easily correctable nerve compressions. These compressions cannot be treated, however, because they can not be reliably diagnosed or located.

The axonal tracer method is exceedingly well suited to the diagnosis of all manner of nerve compression syndromes. These patients rarely have complete denervation, so axonal transport still functions distal to the compressional point. This is a realm where the competing method is EMG (a three month waiting list for this painful test is common in the UK) or, in many cases where there is no existing method at all for confirming a clinical suspicion without surgical exploration.

A related area of use concerns cranial nerve compressing responsible for trigeminal neuralgia, Glossopharyngeal neuralgia Torticollis, hemi-facial spasm, Vertigo/Meniere's Disease, and even essential hypertension due to Vagal compression.

Incontinence and Impotence: Another extremely common problem which is exceedingly difficult for the physician to evaluate is urinary incontinence and bladder dysfunction. It is en important to determine whether there is any failure of the nerves involved in distinction from a mechanical failure. This is currently an extremely difficult problem. However, a few carefully placed injections would permit imaging studies capable of identifying a variety of treatable causes. A similar set of problems also arises occasionally in the evaluation of male impotence.

Localization of Nerve Bruises and Lacerations: The muscles of the face are operated by a single nerve which is unfortunately subject to severe bruising or even laceration at several points during traumatic facial injury. A clinician is often presented with a patient who, after a blow to the face, has a risk of irreparable corneal abrasion because he cannot close his eye, a distorted and grotesque fixed facial droop, and an ongoing drool from the corner of a mouth he cannot elevate. The problem is that there is no way to locate the exact site of injury along the complex course of the nerve as it travels among bones, muscles, glands, arteries, and other structures. If there is only a bruise to the nerve, then it will recover on its own over months with no intervention required, but if the nerve is actually lacerated, it must be reconnected surgically on an urgent basis to minimise the risk of retraction requiring subsequent nerve grafting.

Unfortunately, until now there has been no way to learn how severe the injury is. Because of the impact on the patient's life if the need to repair is not appreciated, one might advocate surgical exploration and direct inspection in all cases. However, because the exact location of injury could not be ascertained, this would require unacceptable incisions at multiple locations on the face and throat with danger to a variety of uninjured structures along the course of the nerve.

This is a frustrating clinical problem, and there is no current method to locate or assess such an injury. Because axonal transport continues for several days even after the nerve is actually cut, the agents described herein would dramatically alter the situation. An injection of tracer into facial muscle could be undertaken immediately in the emergency department and imaging would be possible within hours because of the small nerve transport distances involved.

Such an investigation could show that contrast agent still passed the compression point—so that only a bruise was responsible—or, even if it could not prove the severity, it would show the surgeon precisely where to look via a tiny incision. Similar considerations apply for traumatic nerve injuries at various locations around the body as well as to the problem of distinguishing between spinal nerve root avulsion and brachial plexus injury.

Assessment of Spinal Cord Injury: In spinal cord injury, it is often difficult to distinguish deficits due to direct damage to the cord from effects of nearby root compressions. Studies of cord injury per se could be approached in several different ways. An injection into muscle would label the motorneuron cell body, and transneuronal transport would then introduce tracer into descending corticospinal neurons. By injecting in transversospinalis back muscles, the initial transport distance could be reduced to no more than two centimeters. A second approach relies on the multisegmental distribution of motorneurons projecting to back muscles. An injection would cause labeling of cell bodies in intact cord with a cutoff in areas where neuron cell bodies were crushed or injured. A third method would be to rely on proprioceptive sensory neurons many of which do not synapse at the level of entry into cord, but project up to the medulla before reaching the first synapse. For this approach, injection of an intervertebral joint capsule might be effective.

Experiments done by the inventor have demonstrated transport of radiolabelled tracer up the spinal cord after intramuscular injection. This has been most successful with small molecule imaging agents such as transneuronally transported WGA and potentially with tetanus toxin fragments, either of which can be labelled with Iodine$^{124}$.

Myelography is considered dangerous immediately after spinal cord injury since the changes in spinal fluid pressure that result from the lumbar puncture can make the spinal cord injury worse. Further, it often fails to reveal details of the site of injury since swelling will tend to exclude dye from the area of injury. MRI is sometimes used, but the results are difficult to interpret since the extra tissue water due to swelling often overwhelms other imaging information.

A variety of other more rare spinal cord conditions might also be better studied by application of this technique. These include congenital anomalies of the spinal cord which lead to tethering and stretching of the spinal nerves, and also a variety of inflammatory or neuritic conditions such as transverse myelitis which may affect axonal transport in the spinal cord.

Evaluation of Neuropathies: Another clinically important aspect of axonal transport concerns peripheral neuropathies such as occur in diabetes. These are conditions which involve dysfunction of nerve metabolism rather than actual mechanical impingement. Diabetic neuropathy afflicts hundreds of thousands of diabetic patients. A common outcome is loss of sensation resulting in sores and ulcers of the feet and legs (occasionally becoming so severe as to set the stage for gangrene or to require amputation), difficulty with balance and loss of the ability to walk. It is difficult to learn how to treat this condition because there is no way to accurately follow its course and no early warning of its onset. A diagnostic agent according to the present invention could be injected into muscle and its rate of progress evaluated with MRI or other imaging techniques. In this fashion, a diagnosis could be made, and the severity assessed. Such a technique would be a tremendous boon to research in diabetes and might help set the stage for progress towards some medical treatment in the future.

This problem as well as a variety of other clinical entities such as amyotrophic lateral sclerosis—which causes profound, even lethal muscle weakness, Alzheimer's disease—which condition is exceedingly difficult to diagnose, and neurologic deficits after shearing type head injuries are all thought to involve disorders of axonal transport or related aspects of axon cytoskeletal function. An imaging study that assesses quantity and rate of transport can permit diagnosis as well as follow the progress of remissions and would also be quite helpful in research.

Oncology

Neuropathy is a complicating concern in the management and treatment of cancer. This is because neuropathies that are due to the cancer itself may be confused with neuropathies caused by chemotherapy. Tumours or metastases of tumours can cause neuropathy by direct mechanical nerve compression, however a number of cancers seem to cause neuropathy by paraneoplastic phenomena which are not entirely understood. A wide variety of chemotherapeutic agents also cause neuropathies and this sometimes is the key limiting factor on maximal permissible dose.

The oncologist is therefore often faced with a dilemma when a patient develops pain, weakness and paresthesias during the course of treatment. If the neuropathy is due to tumour progression, then increased therapy is indicated. However, if the neuropathy is due to the treatment itself, then those drugs must be abandoned or replaced. An axon tracer imaging technique would be helpful in identifying nerve and spinal cord compression, in studying the puzzling paraneoplastic effects, and in the development, dosing and monitoring of chemotherapeutic agents.

Epilepsy

Another interesting possibility is a link between axonal transport and epilepsy. Kainic acid is used to induce a murine model of epileptic kindling in the hippocampus. It is well known that this involves increased excitability of the involved cells. It has been observed that kainic acid also serves to block retrograde transport of horseradish peroxidase. If there is any association between epileptic foci and altered axonal transport, this could lead to a means of imaging epileptic foci as part of, for example an operation for microelectrode array placement done several days prior to the definitive epilepsy surgery. Intra-operative application of the tracer at the first operation would provide useful information for the second procedure.

Verification of Denervation

It is sometimes desirable to denervate a structure. The most common such situation is surgical vagotomy to treat ulcer disease. In these cases it is essential to achieve total vagal denervation in order to assure there is no further gastric acid production. However, because of the complexity of the vagal innervation it is often difficult to be certain if an adequate result has been obtained. This may require the continued use of various kinds of testing for acidity and the continued use of medications at considerable expense and difficulty for the patient. A misjudgment may lead to death by internal bleeding or gastric perforation. Oral administrations of axonal transport imaging agents will permit repeated assessments of vagal innervation of the stomach and upper GI tract as these can be absorbed from the gastric wall if vagal innervation is intact.

Intraoperative Nerve Identification

There are a number of situations in which the neurosurgeon is faced with extreme difficulty in distinguishing nerves from pathological tissues of roughly similar colour and texture such as tumours or fibrotic fat pads. This includes surgery for untethering of lipomyelomeningoceles and surgery for removing acoustic neuromas where the facial nerve passes through the tumour. In this latter situation for instance, a fluorescein conjugated or chromophore conjugated, dextran coated ferrite with a nerve adhesion molecule conjugated as well may be used according to the invention. An injection into the facial musculature is done preoperatively and an MR image is obtained to demonstrate the course of the facial nerve through or around the tumour. An appropriate ultraviolet or other light source can be directed towards various areas of the tumour mass to permit direct visual confirmation of nerve location by the surgeon intraoperatively.

Clinical Research Uses

Outside of purely clinical issues, there are a variety of compelling areas of neurobiology research where the diagnostic agents of the invention can be used, e.g. intraoperative research on the neurophysiology and distribution of speech areas in awake humans. Although neuroanatomical tract tracing studies have been carried out in monkeys to identify connections among areas thought to be homologous to human speech areas, human studies are needed. An axonal tracer with an MRI detectable label might permit tract tracing studies in humans in conjunction with the intraoperative recordings.

Therapeutic Uses

It is often necessary to administer drugs whose intended site of action is in the spinal cord or dorsal root ganglia (DRG). However, in the past there has been no easy way of safely administering such drugs near their site of action. While injections are commonly used to achieve local drug effects in muscle or in joints, it is exceedingly hazardous to introduce a needle percutaneously and blindly into the vicinity of the spinal cord or sensory ganglia. Therefore, in order to achieve pharmacologically efficacious doses of various drugs at these locations it has been necessary to give very high systemic doses by intravenous and oral routes, or by intramuscular routes wherein the actual delivery of the drug depended upon vascular uptake from the injection site in order to achieve the best available distribution. Alternatively, cumbersome procedures in which special catheters are threaded into place near the spinal cord have been undertaken with attendant dangers of spinal cord injury. There has never been any route except by whole body vascular distribution to deliver any drugs to ganglia.

However, by taking advantage of the drug distributions achievable by axonal transport where particulates are used, a dramatic change in pharmaceutical practice can be achieved. When the desired drug is trapped in a polymer, liposome, or protein nanosphere with an attached nerve adhesion molecule, it becomes possible to carry out an intramuscular injection of an extremely small amount at a location to which the desired part of the nervous system is connected by a peripheral nerve. Most of the injectate will stay in the muscle at the site of injection while the drug particles are ingested by nerve endings and transported to the ganglionic or spinal cord sites toward which treatment is to be directed.

Liposomes with phosphatidlycholine and phosphatidylethanolamine (e.g. as described by Grant in Mag. Res. Med. 11: 236–243 (1989)), derivatized for attachment of a nerve adhesion molecule can be prepared in the necessary size range for efficient uptake and neuronal transport. In this fashion, a wide variety of hydrophilic and hydrophobic drugs can be packaged for delivery direct to their intended neural sites of action while minimizing systemic dose.

The particles yield a large amplification of the uptake process since many drug molecules are ingested by the cell with each event and helps minimize spread of the drug away from the injection site.

While there are a number of well known methods for producing particulate drug carriers, many of these are not suitable for intraneural drug delivery. Many of the known techniques are not applicable because they result in the production of particles which are far too large to permit access to the axon terminus in general and synaptic cleft in particular as needed to promote neural uptake. For instance, many polylactic acid particles can only be produced in sizes near 100 microns which is three orders of magnitude too large. Liposomes similarly tend to be too large unless they are produced as small unilamellar vesicles (SUV) which require harsh physical and chemical conditions for synthesis.

Polycyanoacrylate/vinyl particulates (many of which are termed "latex" microspheres or nanoparticles) can be readily produced in the appropriate size range, but require the use of organic solvents and other treatments which are destructive to many biological molecules of therapeutic interest. Albumin or other protein microspheres of useful size can be produced from sonicated emulsions, but these require denaturing by heating over 100° C. or chemical crosslinking to achieve stability and this similarly limits the range of potential pharmaceuticals.

Metal oxide particles are particularly convenient as drug carriers. They readily form stable colloids of appropriate size and can be coated by a wide variety of molecules. When the particles are prepared by adding a strong base to the metal chlorides in saturated dextran, a strong bond between the particle and the dextran is formed. Subsequently, some proteins can be covalently bound to the dextran molecules. However, this type of synthesis precludes the use of any drugs which cannot tolerate the strong acidity of the metal salts or the rapid shift to a strong alkali typically used in the precipitation reaction.

The predominant solution to this problem has been to precipitate the particles with no coating, and then apply the coating at a later step under more mild conditions. However, whether NaOH or $NH_4OH$ is used, and whether the metal salts are added to the alkali or vice versa, uncoated particles always aggregate and despite high power sonication of the resuspended pellets, it is difficult to produce a stable colloid.

Precipitation by addition to ammonia is more effective than using NaOH because of a clear peptizing effect reconfirmed in experiments conducted by the inventor. Such uncoated ammonia precipitates become stable for centrifugal ultrafiltration even without sonification. This preparation is sufficiently reactive as to permit reliably stable but non-covalent binding of a wide range of molecules. In one series of preparations made by the inventor, coatings were made with alpha-cyclodextrin which is capable of binding relatively non-polar drugs and is well known as a drug vehicle. Further, particles were prepared which were first used to adsorb tritiated dexamethasone and then to adsorb WGA. These particles were finally coated with dextran or bovine serum albumin to cover unused reactive sites on the particle surface. Preparations of this sort were subjected to repeated washing, ultrafiltration, and N-acetylglucosamine affinity purification. These steps demonstrated a very slow release of the labelled dexamethasone, but also showed that the affinity purified particles carried with them a high concentration of bound dexamethasone.

Particles of this sort can be used to introduce this helpful steroid drug into neurons for delivery to areas of spinal cord injury. As has also been shown by the inventor, such particles are extruded from the neuron into the endoneurial space and so are then placed in a position to properly interact with and activate cell surface glucocorticoid receptors at otherwise inaccessible locations inside the blood brain barrier.

An entirely novel means of producing metal oxide particles under mild conditions suitable for delicate proteins and peptides has also been developed by the inventor. This method is based on the tendency of mixed iron salts to commence precipitation when the pH is raised above 4.0. Thus, rather than raising the pH of the solution to pH 9, 10 or 11 as is done in all previously known methods, the new method involves precipitating the crystals at physiological pH in biochemically tolerable buffer solutions.

Thus viewed from a further aspect the invention provides a method of producing a physiologically tolerable particulate metal oxide, said method comprising precipitating said oxide from a biologically tolerable, physiological pH buffered solution, optionally containing a coating agent whereby coated particles are formed.

For instance, a strong buffer such as 1 molar HEPES pH 7.4 is prepared with the desired coating molecules in the buffer solution. The mixed metal salt solution, either with or without dextran, is then added to the buffer solution in dropwise fashion. This method has resulted in the production of stable coated colloids produced at physiological pH. This new method of production of these crystals greatly broadens the range of pharmaceuticals which can be included in the particle coat of these 10–100 nm particles for delivery by intraneural or other routes.

Treatment of HTLV-I Associated Myelopathy

A focal infection of the spinal cord associated with HTLV-1 (Human T-Cell Leukaemia Virus, type 1) in which there is involvement of the phagocytic microglia and oligo-dendrocytes as well as of neurons has presented a very forbidding picture for any possible treatment options. What few anti-viral agents have been available have poor penetration of the blood brain barrier and so must be administered intravenously in very high concentration to achieve potentially therapeutic dose levels in the spinal cord. Similarly, intrathecal administration into the CSF allows uncontrolled spread of the anti-viral agent throughout the CNS, affecting various sites of reduced blood brain barrier (e.g. median eminence of the hypothalamus, pineal gland, and area prostrema) more than the infected site. Further, intrathecally administered drugs tend to be swept out of the CSF into the blood stream over a relatively rapid time course compared to what is required for anti-viral therapy.

However, because of the focal nature of the lesion, it is quite easy to identify the dermatome supplied by the involved location of the spinal cord. Therefore, by undertaking intramuscular injections in neck/back muscles as well as in muscles placed at greater distances from the spinal cord, it is possible to set up a continuous inflow of specific medication into the CNS neurons, and by transcellular transport, into the surrounding oligodendrocytes and microglia. The active agents used can include small molecules conjugated to a nerve adhesion molecule, small liposomes or other types of nanoparticles carrying antiviral drugs. The administration of steroids by the same route can also help to reduce injury due to inflammatory components of the disease.

Where transport in the affected dermatome is severely impaired by extensive cell death, injections on the contralateral side of the body and at dermatomes below and above those affected will still bring the drugs into a relatively high concentration at close proximity to the lesion and usefully across the blood brain barrier.

Pain

Among the most common of all tasks faced by the physician or surgeon is the treatment of a severe localized pain whose duration will probably be only a few days but which will cause considerable distress and discomfort to the patient. This might be from a bone fracture, ankle sprain, a surgical incision, abscess, severe back muscle spasm, exacerbation of arthritis, dental extraction, burn, or tumour among other problems. The available pharmaceutical options at present fall into four main categories, an oral drug such as aspirin or acetaminophen which acts at the site of injury by altering the effects of prostacyclin related pain mediators, a range of oral or locally injected anti-inflammatory drugs of both steroidal and non-steroidal composition, locally injected anaesthetics such as marcaine or lignocaine which reduce neural activity, and the systemic administration of opiates or opiate analogs by oral, intramuscular or intravenous routes. There are a few extraordinary treatments most commonly undertaken in cancer patients such as the placement of continuous infusion morphine cannulas near the spinal cord but these are little used because of difficulty in preventing infection and the complexity of placing them. Further, such treatments cannot be used for pain in the arm or neck because free opiates in spinal fluid of the upper spinal cord may reach the medulla and cause respiratory arrest.

If opiate or anti-inflammatory drugs are included in particles, bound to nerve adhesion molecules, and then injected in the dermatome/myotome which is involved in the pain, then an extremely efficient distribution can be achieved. This permits the extended administration of an opiate at an extremely high concentration in the dorsal root ganglion and dorsal root entry zone of the spinal cord at the involved level, while resulting in negligible systemic levels of the drug. For opiates, this avoids tolerance, sedation, respiratory depression and addiction and provides for steady long term administration over days after a single injection. For steroids and non-steroidal anti-inflammatory drugs, this will help reduce the risk of gastric irritation and internal bleeding as well as the other side effects of steroids.

Some types of chronic pain syndromes are remarkably resistant to all standard pain medications including the various opiates and opiate derivatives. The prototype for this sort of pain is trigeminal neuralgia and indeed the sine qua non of this syndrome is that the pain can be relieved only by anticonvulsant medications such as carbamazepine. This sort of chronic pain is often viewed as a kind of focal sensory epilepsy. The problem in treating such pain is that there is often great difficulty in achieving adequate doses at the dorsal root entry zone of the spinal cord or the trigeminal nuclei in the brainstem without causing unacceptable systemic side effects. By use of pharmaceutical agents according to the invention, agents such as carbamazepine can be delivered via an intraneural route after intramuscular injection or intradermal injection.

Spinal Cord Injury

Although acute spinal cord injury has long proven very difficult to treat, it has recently been appreciated that extremely high doses of methylprednisolone given intravenously over the first 24 to 48 hours post-injury can be significantly beneficial to eventual neurological outcome. Of course, the actual site of action is at the injury location in the spinal cord, but the dose is limited by the extremely large amounts of steroid which must be distributed to the rest of the body for no useful purpose.

These steroids can be incorporated into liposomes or other particles of appropriate size, conjugated to a nerve adhesion molecule and injected intramuscularly in back or neck muscles at the level of sensory or motor loss. When this is done, they are transported directly into the nervous system at a continuing flow and arrive precisely at the site of injury. Wherever actual nerve compression or injury has occurred, the transported agent will accumulate and automatically achieve particularly high concentrations. Drug leaking out of torn or inflamed cells, and extruded into the nervous tissue around the affected neurons will act on other injured tissues in the vicinity. This will also assure good delivery into the spinal cord grey matter even when the fracture has caused venous congestion which is slowing vascular delivery to the most affected areas.

Certain pharmaceutical agents useful in the method according to the invention are already known—others may be produced by methods analogous to those used for producing the known agents, e.g. for particulate agents: obtaining particles of a matrix material comprising a physiologically active agent or diagnostic marker; optionally coating said particles with a physiologically tolerable optionally biodegradable coating material, e.g. a natural or synthetic polymer or derivative thereof such as latex, polylactic acid, proteins, albumin, polysaccharides, starches, dextrans, polymerized sugar alcohols, etc (see for example EP-A-184899 (Jacobsen)); and conjugating said particle (optionally via coupling to a said coating, optionally after appropriate derivatization thereof e.g. to provide a binding site or to block excess binding sites) to a nerve adhesion molecule, preferably with a NAM: particle ratio of up to 10, especially up to 5 more especially up to 2 and most preferably about 1; optionally separating NAM-conjugated particles so formed from unconjugated particles, preferably by size separation, especially preferably by repeated size separation followed by at least one affinity separation; optionally sterilising the NAM-conjugated particles, if desired after formulation thereof with a pharmaceutical carrier and optionally with further conventional pharmaceutical excipients, e.g. viscosity enhancing agents, pH regulators, osmolality adjusting agents, etc.

The matrix material used may be an inorganic matrix, e.g. a metal oxide, or an organic matrix, e.g. a polymer such as a cross-linked starch or dextran, and it may serve as a carrier for the physiologically active agent or diagnostic marker or it may itself serve as the active agent or marker, as would for example be the case with superparamagnetic ferrite crystals.

Incorporation of the agent or marker within a carrier matrix can be achieved by conventional techniques, for example by co-precipitation, by steeping a porous matrix material to impregnate it with the desired agent or marker, by exposing the agent to ultrasonically suspended, uncoated metal oxide particles, or by means of the buffered precipitation technique described herein.

The matrix particles should desirably be relatively uniformly dimensioned, e.g. within the ranges discussed above, and this may be achieved for example by conventional screening or particle precipitation techniques. Monodisperse particles will be preferred.

Where the agent used according to the invention is non-particulate it may again be produced by conventional techniques, e.g. by binding a desired nuclide directly or via a chelant molecule to a NAM or by binding a chromophore or fluorophore or a physiologically active molecule to a NAM, optionally and indeed preferably so as to provide a biodegradable bonding which will permit liberation of the physiologically active agent after endocytosis.

For axonal delivery of therapeutic or prophylactic substances, in certain cases it may be desirable in the method of the invention to select physiologically active substances which occur naturally in neurons or which are analogues of such naturally occurring substances.

Viewed from a further aspect the invention provides a process for the preparation of a particulate pharmaceutical agent according to the invention which process comprises conjugating a NAM to an optionally coated particulate physiologically active or diagnostically marked substance.

Viewed from a yet still further aspect the invention provides a process for the preparation of the physiologically tolerable marked metal oxides, metal sulphides or alloys of the invention which comprises precipitating a said metal oxide or sulphide from a solution containing a positron emitter nuclide and preferably also containing an element having high positron affinity, and if desired reducing said precipitate.

Viewed from a yet still further aspect the invention also provides a process for the preparation of the modified spinel and garnet particles according to the invention which process comprises precipitating di and trivalent metal ions of ionic radii such as to permit crystals of spinel or garnet structure to form, said precipitation being from a solution containing scandium, a radioactive yttrium isotope, a sixth period metal, a high MR receptivity nuclide or an element having a desired therapeutic or prophylactic activity.

In these particle precipitation processes according to the invention the physiologically active, marker, or high positron affinity elements to be incorporated into the particles may be in solution or alternatively they may be in fine "seed" crystals which become included in the precipitating particles.

For administration in vivo, the dosages used will clearly depend upon a wide range of factors such as the patient's weight, the specificity of the NAM (for NAM-conjugated agents), the nature of the imaging or visualization modality (e.g. ultrasound, MRI, CT, PET, scintigraphy, etc) where the agent is to be used to assist surgery or diagnostic investigations, the nature of the physiologically active or diagnostic marker component of the pharmaceutical agent, the extent or severity of the injury or ailment that is being investigated or treated, the distance over which axonal transport is required, etc. The appropriate dosage however can readily be determined taking these factors into account.

However the intramuscular administration according to the invention of NAM-targetted agents offers the possibility of very efficient and very specific delivery. Thus taking the example of a PET contrast agent, to fill the volume of a peripheral nerve one might require 0.1 microCurie, i.e. 0.01 $\mu$Ci/ml. The injection site might commence with 50 $\mu$Ci in a 10 ml volume of muscle (5 $\mu$Ci/ml), but Within 24 hours the injectate of a small molecule tracer with minimal affinity for muscle would distribute in about 50 liters of blood and extracellular fluid space yielding a concentration of 0.001 $\mu$Ci/ml and thus even reconcentration in for example liver or kidney would not overwhelm the signal from the nerve.

For MRI, NAM-targetted 10K dextran-coated superparamagnetic ferrous ferrites, e.g. incorporating Zn(II) and Mn(II) in normal spinel inclusions to enhance magnetization and optionally Co or Mn but much more preferably Sc doped to permit detection/verification by MRS, may conveniently be administered intramuscular as 10–100 $\mu$l doses containing 5–20 mg Fe/ml, e.g. produced by a Centriprep-30 concentrator. 10000 MW dextran may be replaced by 1500 MW or more preferably 6000 MW dextran.

The invention is illustrated in more detail by the following Example of diagnostically marked ferrites.

EXAMPLE

Ferrite particle synthesis can be efficiently carried out in less than 24 hours. The chloride salts of the metals with the positron nuclide (if desired) at specific activities of 1 $\mu$Ci-1 mCi/mM Fe (370 MBq-3.7 GBq/$\mu$M) of 2+ and 3+ oxidation state metal (both metal salt s may be stable $Fe^{56}$) are dissolved in a saturated or supersaturated solution of 1,500 to 10,000 MW dextran preferably 10,000 MW in a ratio near Mt(II)1.0:Fe(III) 2.0 at a concentration of 0.2 to 1.0 molar and at a temperature of 0–60° C. depending upon the final particle size distribution desired but preferably at 50° C. and where Mt is the divalent cation of a transition metal or of a mix of transition metals. Typical starting amounts are 540 mg $FeCl_3$, 230 mg $FeCl_2$, 3 gm Dextran 10K, in 4.5 ml of $dH_2O$. The dextran solution should be heated only briefly to avoid recrystalization or sludging.

Trivalent cations (such as Sc(III)) may be used in low ratios if they are stoichiometrically balanced with monovalent metal salts, preferably LiCl. The ferrites are precipitated by addition of 5 to 10%, preferably 7.5% aqueous solution of $NH_3$ to reach a pH of 9 to 12 and preferably pH 11 (about 15 ml added to 7.5 ml of dextran/metal salt solution). This solution can be heated to 60° C. prior to adding it to the metal/dextran solution.

By omitting LiCl in the precipitation reactions with $_{25}Mn^{52}$, and $_{26}Fe^{52}$, any chromium decay product is unlikely to remain at a II oxidation state and so will tend to be excluded from the crystal, resulting in a sort of final purification at time of synthesis which effectively increases the specific activity of the nuclide and helps preserve maximal possible magnetic saturation of the ferrites.

A variety of sizes of dextrans can be used, for example ranging from 1.5K to 40K MW although the 10K dextrans have proven most reliable in these syntheses. Changes in outer coating also effect the tumbling behaviour of the particles and this can have an effect on some resonant behaviour of the particles and on their interactions with water molecules. It is also possible to coat the particles with non-metabolizing latex from for example cyanoacrylate monomers to alter their rate of processing through the cells. Other biodegradable coatings such as polylactic acid or even protein/albumin coats can be applied. A shift in average crystal core size towards smaller size can be produced by lowering the temperature of the synthetic reaction or elevating the pH. However, a variety of separation techniques may then be required to trim the size distribution to select the desired size range.

Additionally, the spinel crystal can be constituted of mixed metals in various amounts in order to achieve various specific optimizations. Mixed spinels including various useful transition series metals, and even some lanthanide metals can be made by adding the metal chloride powders directly to the saturated dextran solution prior to alkali precipitation.

The product of the reaction is centrifuged 2 times at 1,000 g×10 minutes and one time at 1,500 g×10 minutes to remove particulates which are discarded in the precipitate. The resulting suspension is passed through a 2.5 cm×40 cm column of Sephadex G-25M/150® (Pharmacia) equilibrated in 0.1M NaAcetate buffer pH6.5 in order to remove free metal ions, particulates, ferrous hydrous oxides, chloride and ammonia.

The Sephadex eluant is then passed through successively finer microfilters. Two passes through a 0.22 micron nylon filter are followed by two passes through a 0.1 micron nylon filter. The third filtration is slow but can be accomplished with 100 mm or 47 mm diameter filters on a suction funnel using a 50 nm filter such as Millipore® VMWP-04700 Cellulose MF filters although nylon filters are preferable. The speed and general success of this step are highly dependent on the initial precipitation conditions—being most efficacious with smaller particle size distribution. These filtrations may also be accomplished with centrifugal filters.

This is cleared, desalted, and size trimmed product is then concentrated with a Centriprep-30® (Amicon) ultrafilter, at 1,500 g for 45 minutes, to achieve a final volume of five to seven ml. The sample is then applied to a 2.5 cm×25 cm column of Sephacryl-200 R (Pharmacia) equilibrated with 0.1M NaAcetate buffer pH6.5 with elution by the same buffer. This traps dextran and small ferrous hydrous oxides while letting the particles pass in the excluded, unfractionated volume. The late tail of this fraction should be discarded as it contains much of the hydrous oxide. The resulting eluant is concentrated to 4 ml with a Centriprep-30 concentrator (1,500 g for 15 minutes) for conjugation.

The particle sample in a volume of 4 ml is oxidized adding slowly 1 ml of 20 mM $NaIO_4$ at 23° C. This mixture is reacted while stirring (non-magnetic stirring only) for 60 minutes in the dark.

The periodation reaction is halted by passing the sample through two PD-10 Sephadex G-25M/150 columns equilibrated with 20 mM NaBorate buffer pH8.5, concentrating with a Centriprep-30 ultrafilter to 1–2 ml then passing the sample through a third PD-10 column of Sephadex G-25M/150 to completely remove any unreacted periodate. The final volume is brought up to 4 ml with borate buffer.

A protein solution is prepared having 2–10 mg of antibody, lectin, growth factor, or other selective adhesion molecule dissolved in 1 ml of 20 mM NaBorate buffer, pH8.5. Where possible, blocking molecules to protect the active/recognition site should be added at this point if the blocker will not be bound by the periodate activated dextran. For example, adding 1 mM $CaCl_2/MnCl_2$ helps protect the binding site on some lectins. This solution is then added to the particle solution, mixed, and allowed to incubate for 4 to 12 hours depending upon the molecule involved and the number of adhesion molecules desired per particle. The reaction is quenched by the addition of 200 microliters of 0.5M glycine with an additional two hours of incubation.

The covalent bonds are then reduced by the addition of 0.5 ml of 0.25M $NaBH_4$ with allowance for the generation of $H_2$ gas. After one hour of reaction, the mixture is passed through three PD-10 columns of Sephadex G-25M/150 equilibrated with 20 mM HEPES buffer at a pH of 7.4 to remove glycine, $NaBH_4$ and $H_2$, then concentrated to a 1–2 ml volume with a Centriprep-100 concentrator (500 g for 60 minutes) to clear unbound adhesion molecule and smaller, unconjugated particles. This product is then applied to a 1.6×35 cm column of Sephacryl 200 and eluted with 20 mM HEPES buffer at pH 7.4. This column run further removes unbound targeting molecules and traps any newly formed hydrous oxides. The eluant is collected and concentrated with a Centriprep-100 concentrator at 500 g×30 minutes to achieve a final volume of 4 ml.

The four ml of reaction product are then applied to a 4 ml column of affinity ligand Sepharose 6B with divinyl sulfone links (such as Sigma A2278 for some lectins) equilibrated with 20 mM HEPES buffer pH 7.4. It is preferable to avoid conditions normally intended to maximize binding as this may make it impossible to elute the specific fraction. The column is then washed extensively with four to five volumes of buffer and then a 2 ml volume of 1 molar affinity eluant in the same buffer is applied. This elutes the active fraction in a fairly sharp band.

The specific fraction is collected and passes through a PD-10 Sephadex G-25M/150 column to help clear affinity eluant and then concentrated to 1 mL with a small volume Centricon-30 centrifugal concentrator (1,500 g×20 minutes). This product is passed through a second PD-10 column and the final output then concentrated to a volume of 300 to 500 microliters with a Centricon-30 concentrator (1,500 g×60 minutes). The final product is then sterilized by 0.22 or 0.1 micron filtration using a Costar 1 ml centrifugal microfilter and stored for use.

For axon transport studies, small injections of 100–200 microliters with 0.5 to 1 mg of particles (at 0.5 to 10 mCi (18.5 to 370 MBq) for PET) are made into muscle with subsequent study with positron emission tomography, X-ray CT, magnetic resonance imaging, or magnetic resonance heteronuclear spectroscopy one to five days after administration as indicated. For tumour evaluation, unlabelled and cold ferrite conjugated irrelevant antibody is administered intravenously followed by intravenous administration of 0.5 to 10 mCi (18.5 to 370 MBq) of positron ferrite/antibody complex. Studies can then be undertaken for tumour evaluation two to five days after intravenous administration with any or all of PET, CT, MRI or MRS.

FIG. 23 shows MR images obtained with $^{52}Mn$ doped ferrite particles obtained in a similar manner. A phantom was prepared using a 2 cm polyacrylamide gel containing the particles with a 1 mm channel of polyacrylamide gel containing the particles at about 25 times higher concentration. This phantom thus mimics the occurrence of a nerve in surrounding tissue (e.g. a leg). The concentrations were selected to simulate the results of the $Fe^{59}$-WGA-ferrite study of FIG. 14. Additionally a syringe with a 3 mm diameter was taped to the outside of the gel-containing 2 cm diameter universal tube. As shown in FIG. 23, using a low resolution multiwire proportional position emission tomography (MUPPET), camera it was possible to distinguish the "nerve" from both the "leg" and the syringe about 1 cm away.

The ferrite particles can be obtained by similar procedures, e.g.:

a) Following a method analogous to that of Molday (J. Immunol. Meth. 52: 353–367 (1982)) metal chloride powder is added directly to a supersaturated 10K dextran solution prior to precipitation with $NH_4OH$. Particle size separation is effected on Sephacryl 1000 with subsequent density gradient centrifuging.

b) The ferrite particles are synthesized by a modification of the method of Molday (supra) which can be efficiently carried out in less than 24 hours. The chloride salts of the metals with the positron nuclide at specific activities of 10–100 mCi/$\mu$M (370 MBq3.7GBq/$\mu$M) of 2+ oxidation state metal are dissolved in a supersaturated solution of 10,000 MW dextran in a ratio near Mt(II)1.0:Fe(III) 2.0 at a concentration of 0.5:1.0 molar and at a temperature of 20–60° C. depending upon the final particle size distribution desired and where Mt is the divalent cation of a transition metal or of a mix of transition metals. The ferrites are precipitated by addition of 8% aqueous solution of $NH_3$ to reach a pH of 11 (about 4 ml added to 2 ml of dextran/metal salt solution), centrifuged at 1,000 g to remove particulates, separated and concentrated with a Centriprep-30 (Amicon) concentrator at 2,000 g for collection of small particles in the filtrate when desired.

The products of this concentration/separation step, either filtrate (reconcentrated with Centriprep-10 concentrator) or retentate, are passed through a preparative column of Sephadex G-25M (150) equilibrated in 0.1M NaAcetate buffer pH6.5 at least four times the volume of the applied sample in order to remove free metal ions, chloride and ammonia.

This desalted sample is again concentrated with a Centriprep-30 concentrator (2,500 g for one hour) to a 3–4 ml volume then passed through a 2.5 cm×25 cm column of Sephacryl-300 (Pharmacia) equilibrated with 0.1M NaAcetate buffer pH6.5 with elution by 0.1M NaAcetate/0.15M NaCl buffer pH6.5 and 0.15M NaCl to separate unbound dextran, and the resulting fraction concentrated to 4 ml with a Centriprep-30 concentrator (2,500 g for 15 minutes) and activated by reacting with 1 ml of 20 mM $NaIO_4$ at 23° C. while stirring (non-magnetic stirring only) for 60 minutes in the dark The periodation reaction is halted by passing the ferrite sample through a Sephadex G-25M (150) column equilibrated with 20 mM NaBorate buffer pH8.5, concentrating with Centriprep-30 to 1–2 ml then passing the sample through a second column of Sephadex G25M(150) to completely remove any unreacted periodate. The protein solution of 2–10 mg of antibody, lectin, growth factor, or other selective adhesion molecule dissolved in 1 ml of 20 mM NaBorate buffer pH8.5 is then added to the ferrite solution, mixed, and allowed to incubate for 4 to 12 hours depending upon the molecule involved and the number of adhesion molecules desired per ferrite particle. The reaction is quenched by the addition of 200 microliters of 0.5M glycine with additional two hours of incubation.

The covalent bonds are then reduced by the addition of 0.5 ml of 0.25M $NaBH_4$ with allowance for the generation of $H_2$ gas. After one hour of reaction, the mixture is passed through a column of Sephadex G-25M(150) equilibrated with 20 mM HEPES buffer at a pH of 7.4 to remove $NaBH_4$ and $H_2$, concentrated to a 1–2 ml volume with a Centriprep-30 concentrator (2,500 g for 30 minutes) and applied to a 1.5 cm×40 cm column of Sephacryl-300 equilibrated with 20 mM HEPES buffer pH7.4 for subsequent elution with 20 mM HEPES/0.15M NaCl buffer pH7.4 in order to remove unbound adhesion molecules and passaged into 0.1M phosphate buffer pH7.4 via Sephadex G-25M for administration.

The resulting fraction can then be concentrated to a 1 ml volume with a Centriprep-30 concentrator for use or further purified with affinity chromatography and subsequent concentration when necessary. Reconstitution after freeze drying can also be used if desired.

c) The ferrite particles are synthesized by a modification of the method of Molday (supra) which can be efficiently carried out in less than 24 hours. The chloride salts of the metals with the positron nuclide (if desired) at specific activities of 10–100 mCi/$\mu$M (370 MBq-3.7 GBq/$\mu$M) of 2+ and 3+ oxidation state metal (both metal salts may be stable $Fe^{56}$) are dissolved in a supersaturated solution of 1,500 to 10,000 MW dextran preferably 6,000 MW in a ratio near Mt(II)1.0:Fe(III) 2.0 at a concentration of 0.2 to 1.0 molar and at a temperature of 20–60° C. depending upon the final particle size distribution desired but preferably at 50° C. and where Mt is the divalent cation of a transition metal or of a mix of transition metals. Typical starting amounts are 540 mg $FeCl_3$, 230 mg $FeCl_2$, 3 gm Dextran 10K, in 4.5 ml of $dH_2O$. The dextran solution should preferably be heated only briefly to avoid recrystallization or sludging. Trivalent cations (such as V[III]) may be used in low ratios if they are stoichiometrically balanced with monovalent metal salts, preferably LiCl. The ferrites are precipitated by addition of 5 to 10%, preferably 7.5% aqueous solution of $NH_3$ to reach a pH of 9 to 12 and preferably pH11 (about 4 ml added to 2 ml of dextran/metal salt solution).

A variety of sizes of dextrans can alternatively be used, ranging from 1.5K to 40K MW although the 10K dextrans have proven most reliable in these syntheses.

Additionally, the spinel crystal can be constituted of mixed metals in various amounts in order to achieve various specific optimizations. Mixed spinels including various useful transition series metals, and even some lanthanide metals can be made by adding the metal chloride powders directly to the saturated dextran solution prior to alkali precipitation.

The product of the precipitation reaction is centrifuged 3 times at 1,000 g to remove particulates which are discarded in the precipitate. The resulting suspension is passed through a preparative column of Sephadex G-25M/150® (Pharmacia) equilibrated in 0.1M NaAcetate buffer pH6.5 at least five times the volume of the applied sample in order to remove free metal ions, chloride and ammonia.

This cleared and desalted product is then concentrated with a Centriprep-100® (Amicaon) ultrafilter, at 1,500 g for two hours, resuspended and again concentrated to a 4 ml volume. This yields good clearance of particles below 5 nm and of unbound dextran into the filtrate for discard and this is the preferred method for the superparamagnetic agent.

When a range of particle sizes including smaller particles are to be processed, this concentration step is done with a Centriprep-30 concentrator. In this case, the unbound dextran will have to be removed by applying the sample as a 3–4 ml volume to a 2.5 cm×25 cm column of Sephacryl-200 (Pharmacia) equilibrated with 0.1M NaAcetate buffer pH6.5 with elution by 0.1M NaAcetate/0.15M NaCl buffer pH6.5 and 0.15M NaCl. The resulting fraction concentrated to 4 ml with a Centriprep-30 concentrator (2,500 g for 15 minutes) for conjugation.

When only very small particles are desired, the initial concentration is done with a Centriprep-100 ultrafilter, but it is the filtrate which is then processed further. This filtrate is reconcentrated three times with a Centriprep-30 ultrafilter to clear the dextran.

When primarily larger particles (in the 50 to 300 nm range) are desired, the desalted, ultrafiltered sample is concentrated with a Centriprep-100 concentrator (2,500 g for one hour) to a 4 ml volume and then applied to a 2.5 cm×25 cm column of Sephacryl-400 R (Pharmacia) equilibrated with 0.1M NaAcetate buffer pH6.5 with elution by 0.1M NaAcetate/0.15M NaCl buffer pH6.5 and 0.15M NaCl. The resulting fraction concentrated to 4 ml with a Centriprep-30 concentrator (2,500 g for 15 minutes) for conjugation.

Particularly for the intraneural agents, it is preferable for the particles to be less than 50 nm in diameter. Therefore, the Centriprep 100 or other product from step 3 is passed through first 0.2 micron and then 0.1 micron Nalgene® nylon microfilters. The resulting product is then concentrated to a 2 ml volume and applied to a 2.5 cm×50 cm column of Sephacryl-1000® (Pharmacia) for size fractionation. Particles in the later fractions are collected for further processing.

The particle sample in a volume of 4 ml is oxidized adding slowly 1 ml of 20 mM $NaIO_4$ at 23° C. This mixture is reacted while stirring (non-magnetic stirring only) for 60 minutes in the dark.

The periodation reaction is halted by passing the sample through a Sephadex G-25M (150) column equilibrated with 20 mM NaBorate buffer pH8.5, concentrating with a Centriprep-30 ultrafilter to 1–2 ml then passing the sample through a second column of Sephadex G-25M(150) to completely remove any unreacted periodate. The protein solution of 2–10 mg of antibody, lectin, growth factor, or other selective adhesion molecule dissolved in 1 ml of 20 mM NaBorate buffer pH8.5 is then added to the particle solution, mixed, and allowed to incubate for 4 to 12 hours depending upon the molecule involved and the number of adhesion molecules desired per particle. The reaction is quenched by the addition of 200 microliters of 0.5M glycine with an additional two hours of incubation.

The covalent bonds are then reduced by the addition of 0.5 ml of 0.25M $NaBH_4$ with allowance for the generation of $H_2$ gas. After one hour of reaction, the mixture is passed through a column of Sephadex G-25M(150) equilibrated with 20 mM HEPES buffer at a pH of 7.4 to remove $NaBH_4$ and $H_2$, concentrated to a 1–2 ml volume with a Centriprep-100 concentrator (1,500 g for 60 minutes) to clear unbound adhesion molecule and smaller, unconjugated particles. This product can then be passaged into 0.1M phosphate buffer pH7.4 via Sephadex G-25M for administration, or further purified by affinity chromatography on non-porous beads or Nalgene® affinity membranes.

The resulting fraction can then be diluted to 20 ml in sterile buffer and passed through a 0.2 micron or preferably 0.1 micron microfilter to assure sterilization. The final product is concentrated to a 1 ml volume with a Centriprep-100 concentrator for use. Reconstitution after freeze drying can also be used to achieve desired concentrations for some preparations.

Alternatively the product of the precipitation reaction is centrifuged 2 times at 1,000 g×10 minutes and one time at 1,500 g×10 minutes to remove particulates which are discarded in the precipitate. The resulting suspension is passed through a 2.5 cm×40 cm of Sephadex G-25M/150® (Pharmacia) equilibrated in 0.1M NaAcetate buffer pH6.5 in order to remove free metal ions, particulates, ferrous hydrous oxides, chloride and ammonia. The Sephadex eluant is then passed through successively finer microfilters. Two passes through a 0.22 micron nylon filter are followed by two passes through a 0.2 micron nylon filter. The third filtration is slow but can be accomplished with 100 mm or 47 mm diameter filters on a suction funnel using a 50 nm filter such as Millipore® VMWP-04700 Cellulose MF filters.

This cleared, desalted, and size trimmed product is then concentrated with a Centriprep-30® (Amicon) ultrafilter, at 1,500 g for 45 minutes, to achieve a final volume of five to seven ml. The sample is then applied to a 2.5 cm×25 cm column of Sephacryl-200® (Pharmacia) equilibrated with 0.1M NaAcetate buffer pH6.5 with elution by the same buffer. This traps dextran and small ferrous hydrous oxides while letting the particles pass in the excluded, unfractionated volume. The late tail of this fraction should be discarded as it contains much of the hydrous oxide. The resulting eluant is concentrated to 4 ml with a Centriprep-30 concentrator (1,500 g for 15 minutes) for conjugation.

The particle sample in a volume of 4 ml is oxidized adding slowly 1 ml of 20 mM $NaIO_4$ at 23° C. This mixture is reacted while stirring (non-magnetic stirring only) for 60 minutes in the dark.

The periodation reaction is halted by passing the sample through two PD-10 Sephadex G-25M/150 columns equilibrated with 20 mM NaBorate buffer pH8.5, concentrating with a Centriprep-30 ultrafilter to 1–2 ml then passing the sample through a third PD-10 column of Sephadex G-25M/150 to completely remove any unreacted periodate. The final volume is brought up to 4 ml with borate buffer.

The protein solution of 2–10 mg of antibody, lectin, growth factor, or other selective adhesion molecule dissolved in 1 ml of 20 mM NaBorate buffer pH8.5. Where possible, blocking molecules to protect the active/recognition site should be added at this point if the blocker will not be bound by the periodate activated dextran. For example, adding 1 mM $CaCl_2/MnCl_2$ helps protect the binding site on some lectins. This solution is then added to the particle solution, mixed, and allowed to incubate for 4 to 12 hours depending upon the molecule involved and the number of adhesion molecules desired per particle. The reaction is quenched by the addition of 200 microliters of 0.5M glycine with an additional two hours of incubation.

The covalent bonds are then reduced by the addition of 0.5 ml of 0.25M $NaBH_4$ with allowance for the generation of $H_2$ gas. After one hour of reaction, the mixture is passed through three PD-10 columns of Sephadex G-125M/150 equilibrated with 20 mM HEPES buffer at a pH of 7.4 to remove glycine, NaBH, and $H_2$, then concentrated to a 1–2 ml volume with a Centriprep-100 concentrator (500 g for 60 minutes) to clear unbound adhesion molecule and smaller, unconjugated particles. This product is then applied to a 1.6×35 cm column of Sephacryl 200 and eluted with 20 mM HEPES buffer at pH 7.4. This column run further removes unbound targeting molecules and traps any newly formed hydrous oxides. The eluant is collected and concentrated with a Centriprep-100 concentrator at 500 g×30 minutes to achieve a final volume of 4 ml.

The four ml of reaction product are then applied to a 4 ml column of affinity ligand Sepharose 6B with divinyl sulfone links (such as Sigma A2278 for some lectins) equilibrated with 20 mM HEPES buffer pH7.4. It is preferable to avoid conditions normally intended to maximize binding as this may make it impossible to elute the specific fraction. The column is then washed extensively with four to five volumes of buffer and then a 2 ml volume of 1 molar affinity eluant in the same buffer is applied. This elutes the active fraction in a fairly sharp band.

The specific fraction is collected and passes through a PD-10 Sephadex G-25M/150 column to help clear affinity eluant and then concentrated to 1 ml with a small volume Centricon-30 centrifugal concentrator (1,500 g×20 minutes). This product is passed through a second PD-10 column and the final output then concentrated to a volume of 300 to 500 microliters with a Centricon-30 concentrator (1,500 g×60 minutes). The final product is then sterilized by 0.22 or 0.1 micron filtration using a Costar 1 ml centrifugal microfilter and stored for use.

BRIEF DESCRIPTION OF DRAWINGS

The invention is also further illustrated by the accompanying drawings already mentioned above in which:

FIG. 5 is a schematic diagram of a portion of a human torso depicting 18) the conus medullaris at the lower termination of the spinal cord and 19) a motor axon which is part of a single cell nearly three feet in length.

FIG. 6 shows the anatomy of the spinal roots with 20) a dorsal root ganglion containing sensory neurons, 21) the dorsal containing sensory axons, 22) the dorsal root entry zone, 23) the dorsal ramus carrying motor and sensory fibers to the back muscles, 24) the ventral ramus carrying motor and sensory fibers to the limbs and anterior portion of the body, 25) the ventral root carrying motor axons, and 26) the ventral grey matter of the spinal cord containing motor neuron cell bodies.

FIG. 7 depicts a motor unit comprising 27) one of several-muscle cells which fire in unison, 28) a muscle made up of many motor units such as the one shown, and 19) a motor axon supplying the motor unit.

FIG. 8 demonstrates 27) a myocyte or muscle cell upon which 19) a motor axon terminates and 29) a muscle spindle with 30) sensory endings as well as intrafusal motor innervation not shown.

Figure 1:
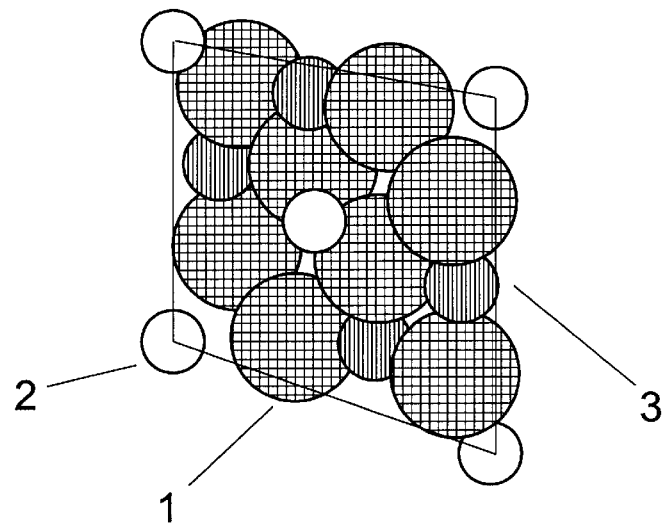
FIG. 1 is a diagram of one face of a spinel crystal demonstrating the position of 1) oxygen atoms, 2) "A" sites for metal ions and 3) "B" sites f or metal ions.
Figure 3:
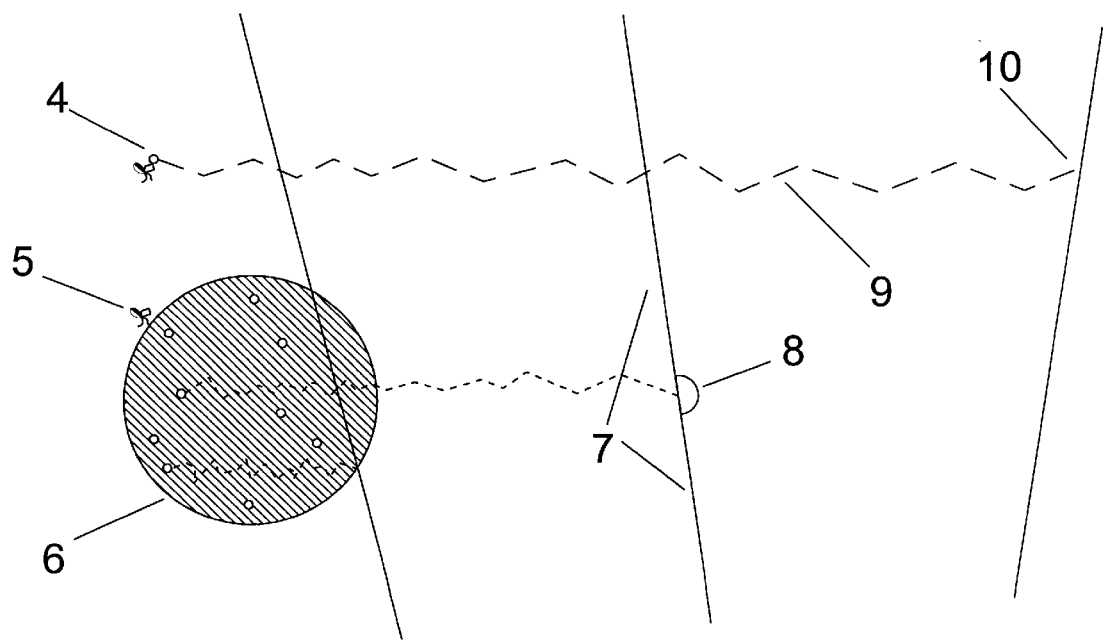
FIG. 3 is a schematic demonstration of the benefits of spinel moderated emitters (SMPE) showing 4) a targeting protein in free solution with a chelated positron emitting atom undergoing radioactive disintegration, 5) a targeting protein bound to the surface of an SMPE particle, 6) a coated SMPE particle with positron ionization tracks marked including one positron proceeding to annihilation before exiting the particle, 7) the paths followed by the two annihilation photons, 8) the correlation angle (nearly 180°) between the two photon paths, 9) the ionization track of a positron travelling in water, and 10) the site of a matter/anti-matter annihilation reaction between an electron and the exhausted positron occurring at some distance from where the initial disintegration took place.
Figure 2A:
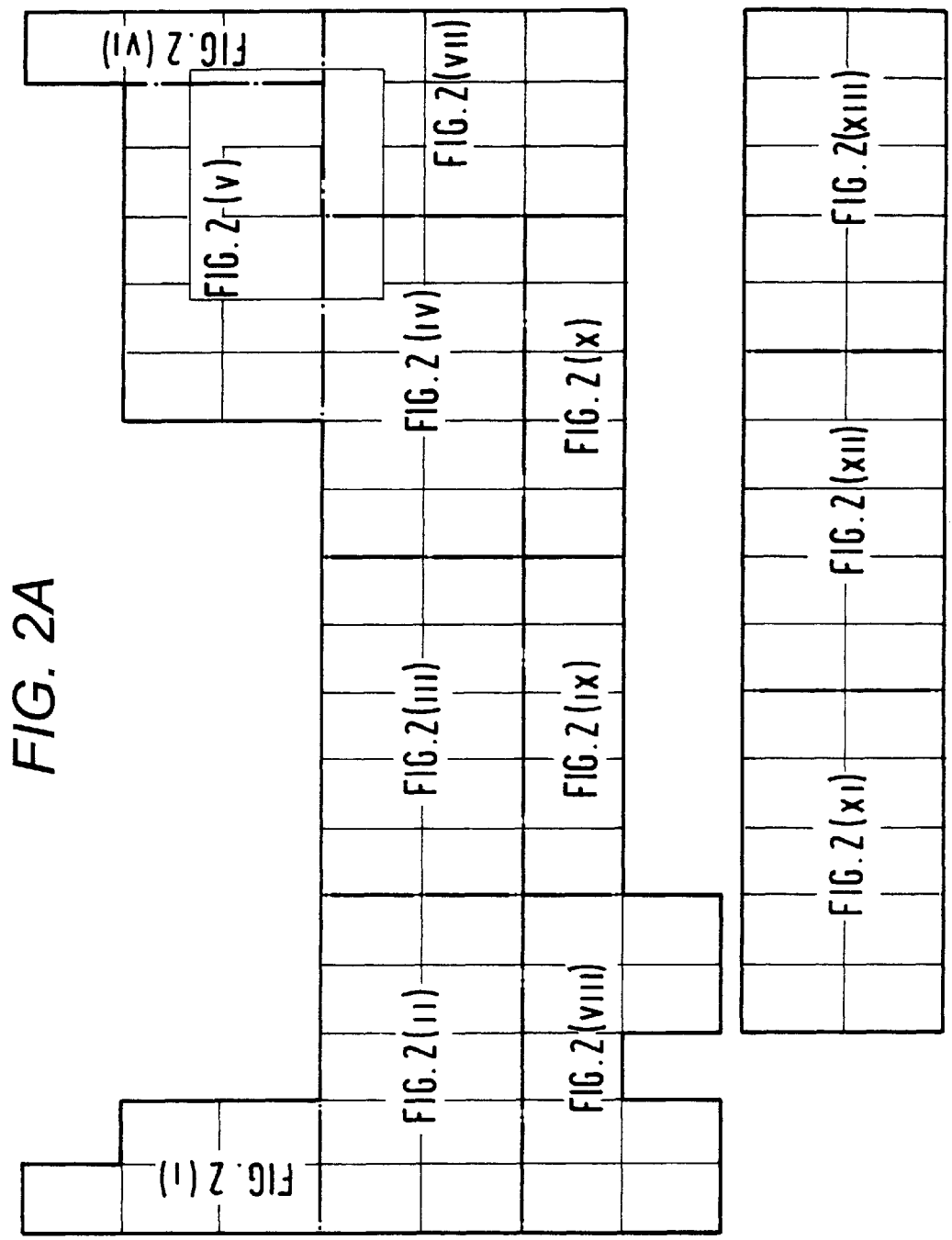
FIG. 2 [2(I)–2(XIII)] is a table of data on various elements discussed herein arranged in the form of the periodic table. Data shown for various elements include radioisotope disintegration pattern, half life and energy profile; magnetic resonance receptivity relative to hydrogen, Larmor frequency at 4.7 Tesla, typical oxidation state and ionic radios, and characteristic positron affinity.
Figure 2B:
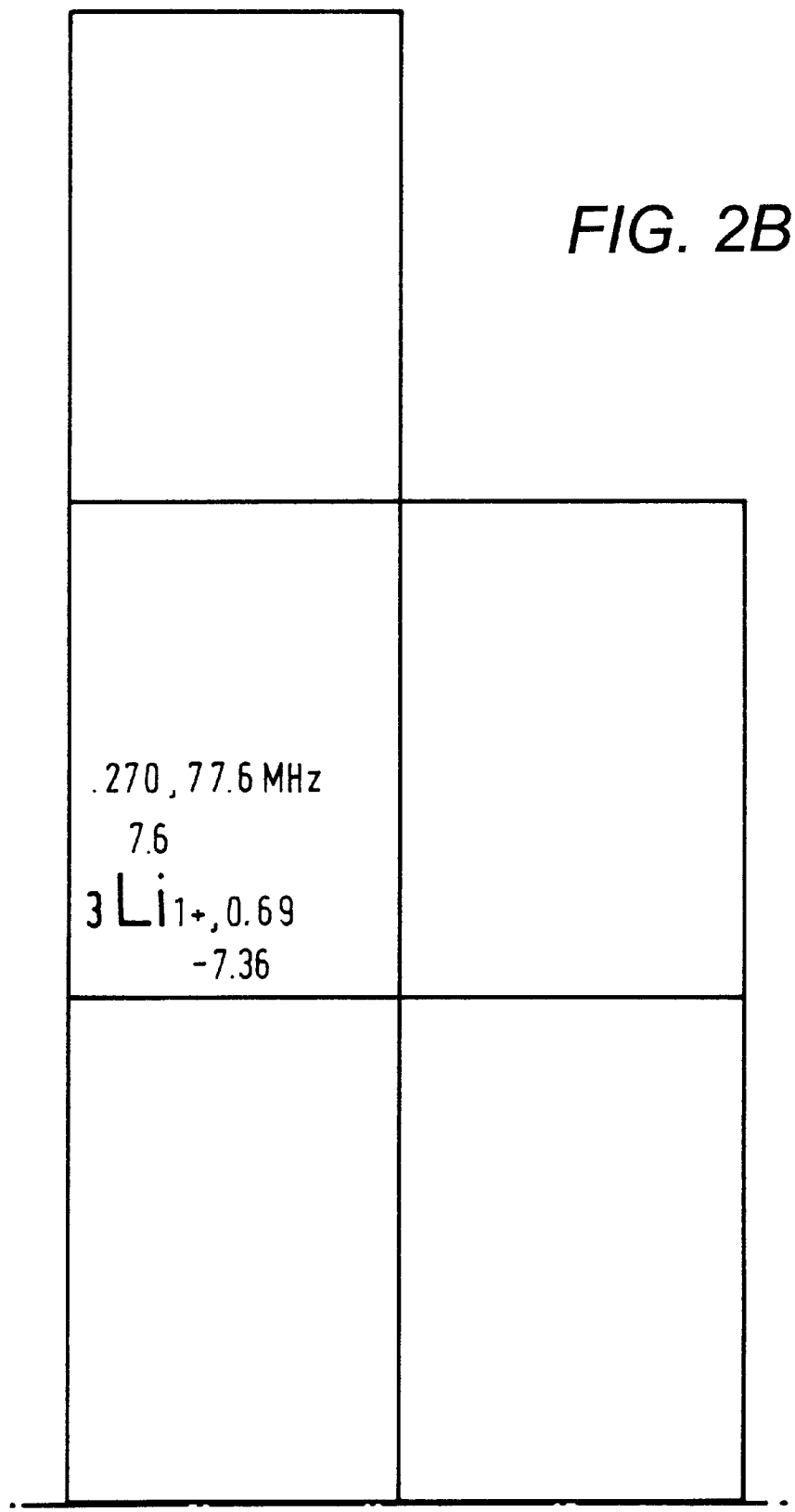
Figure 2F:
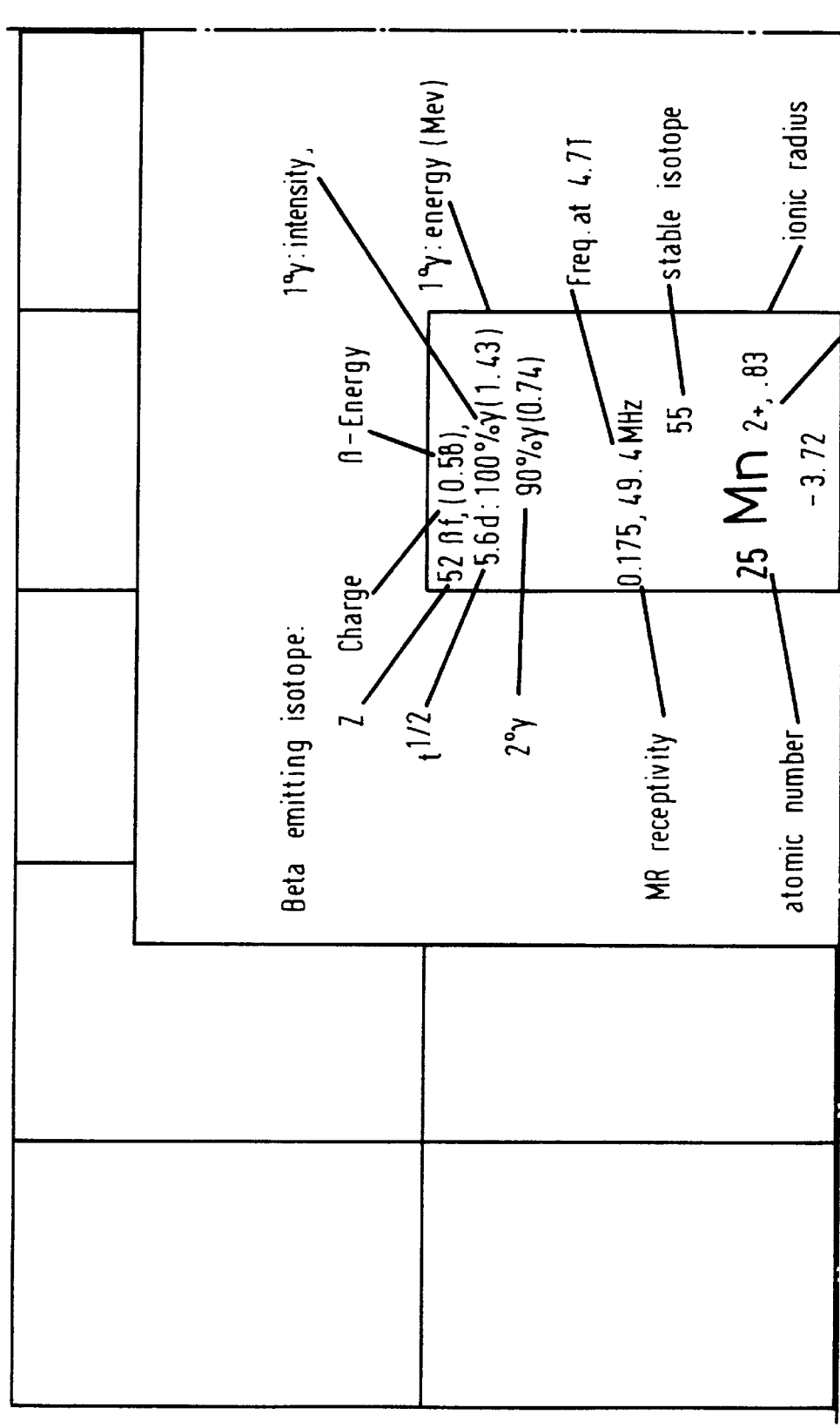
Figure 2G:
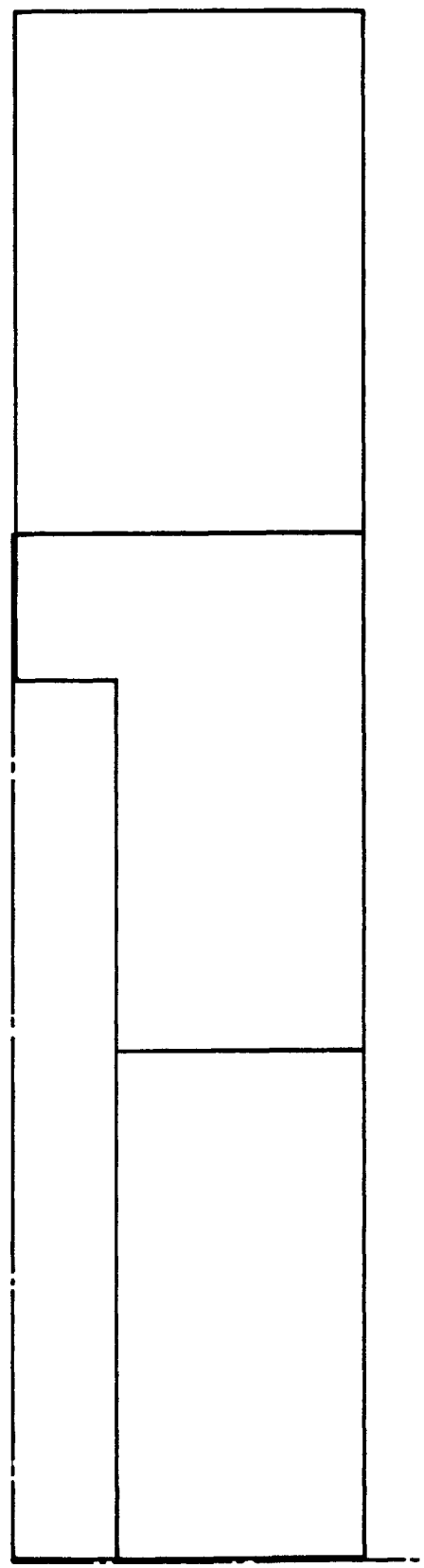
Figure 21:
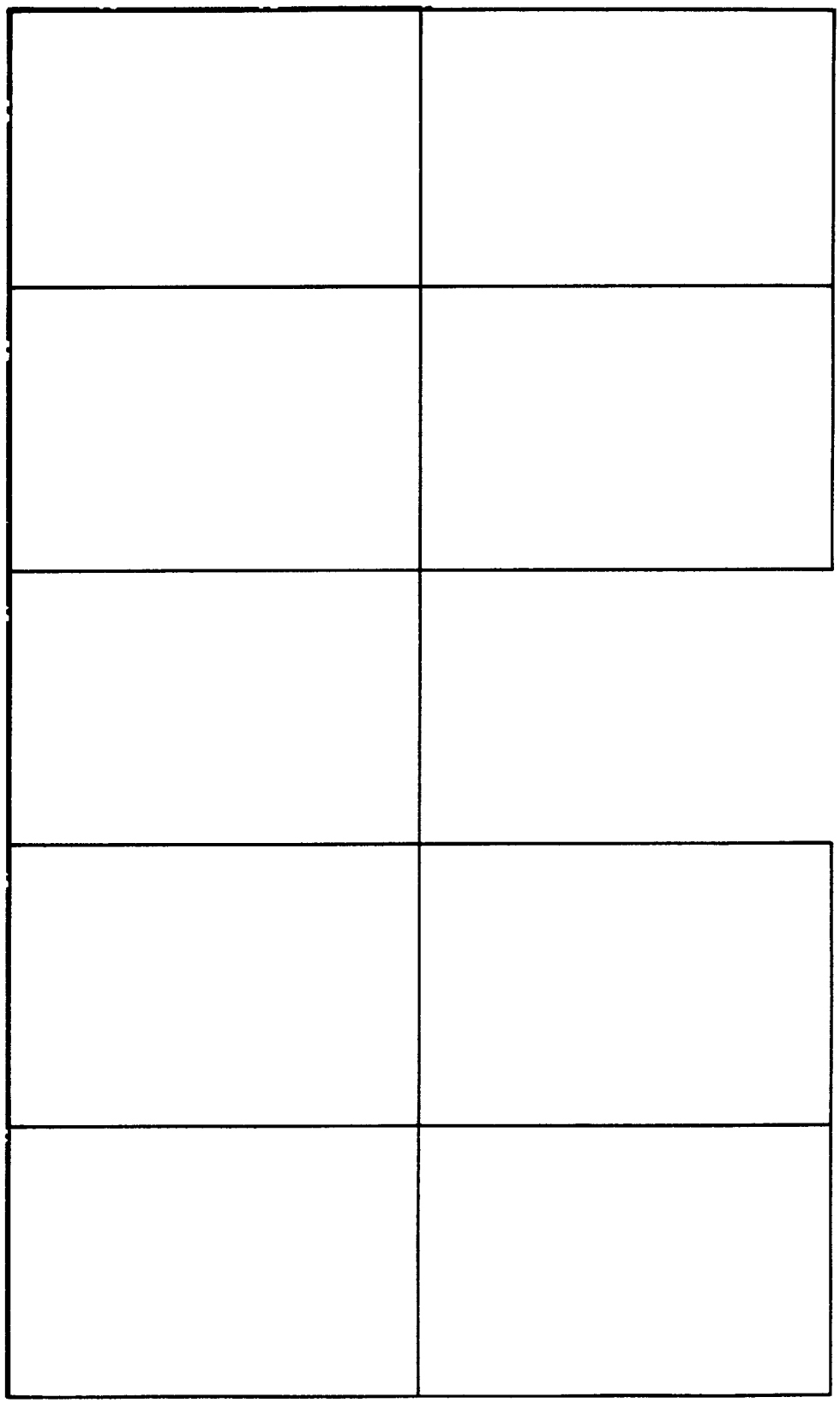
FIG. 21 is an electron micrograph of the tibial nerve of a rabbit collected three days after intramuscular injection with WGA-dextran magnetite. The photograph shows the thick myelin sheath and, within the axon, small particles and large vesicles associated with the particles.
Figure 2K:
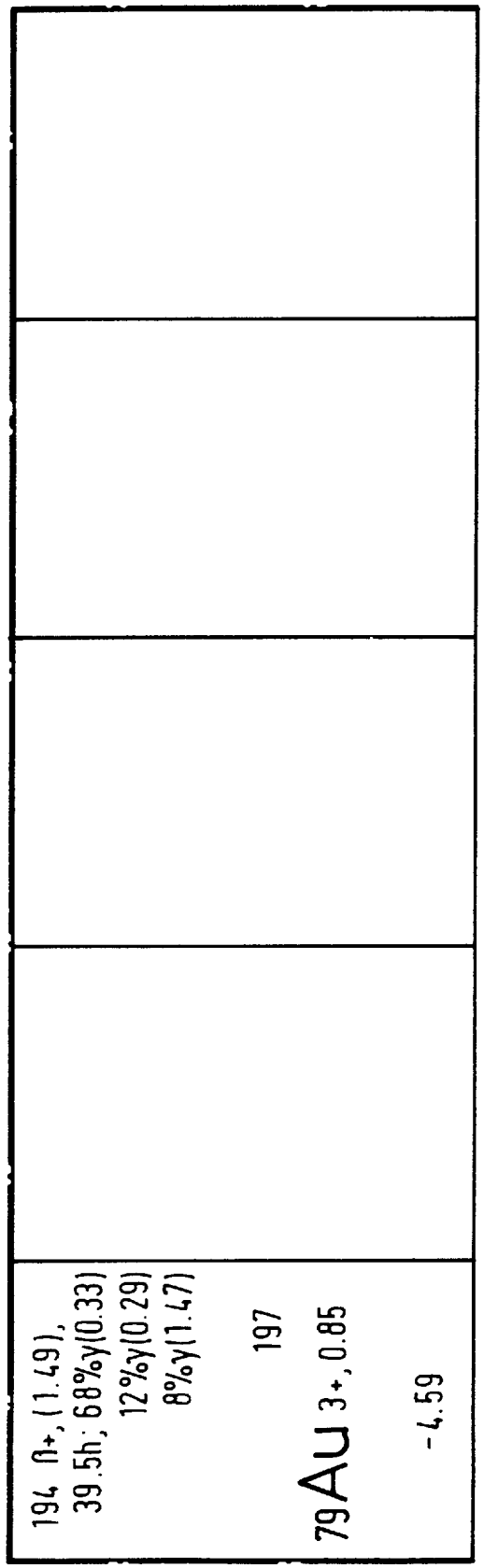
Figure 2N:
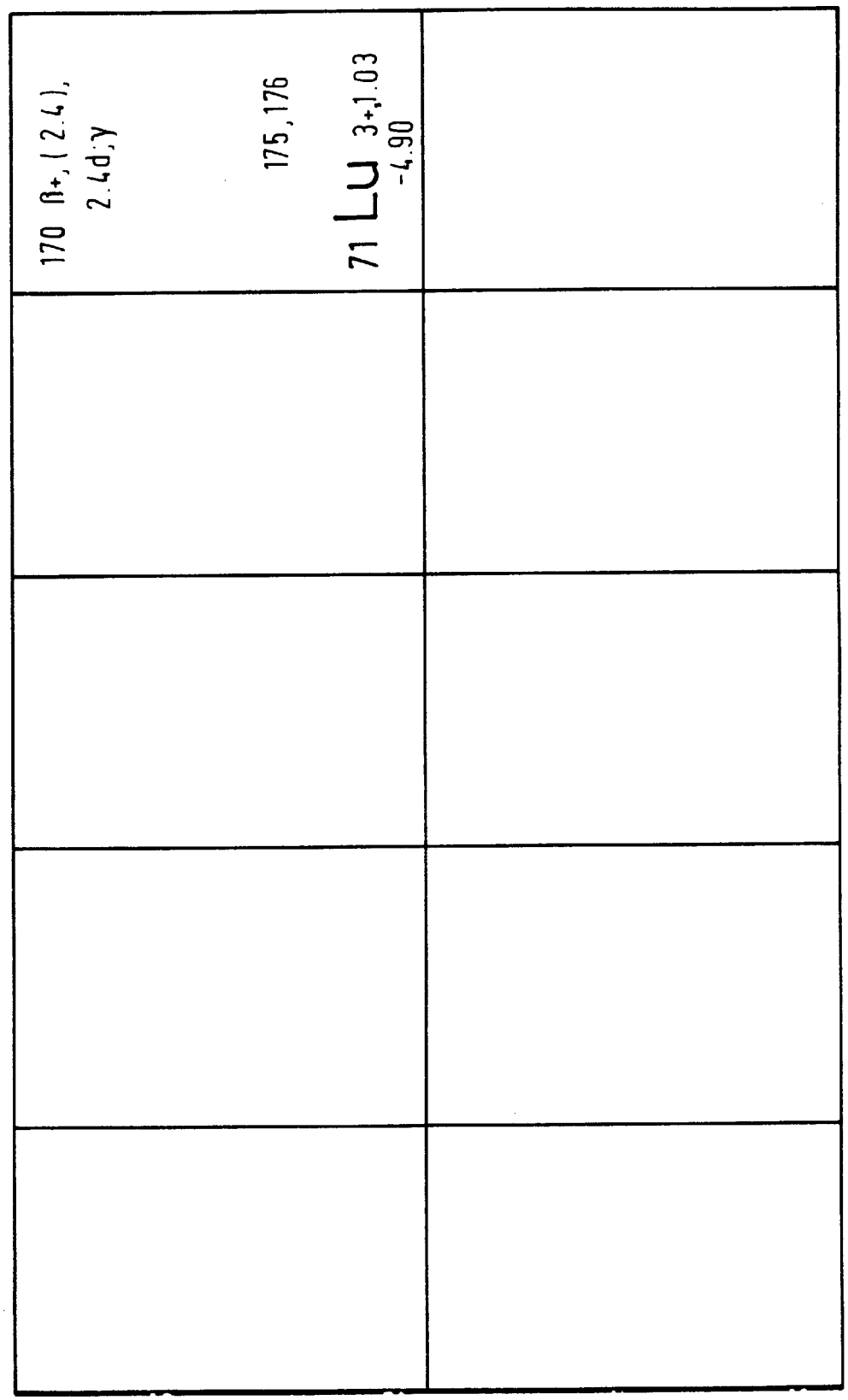
Figure 4A:
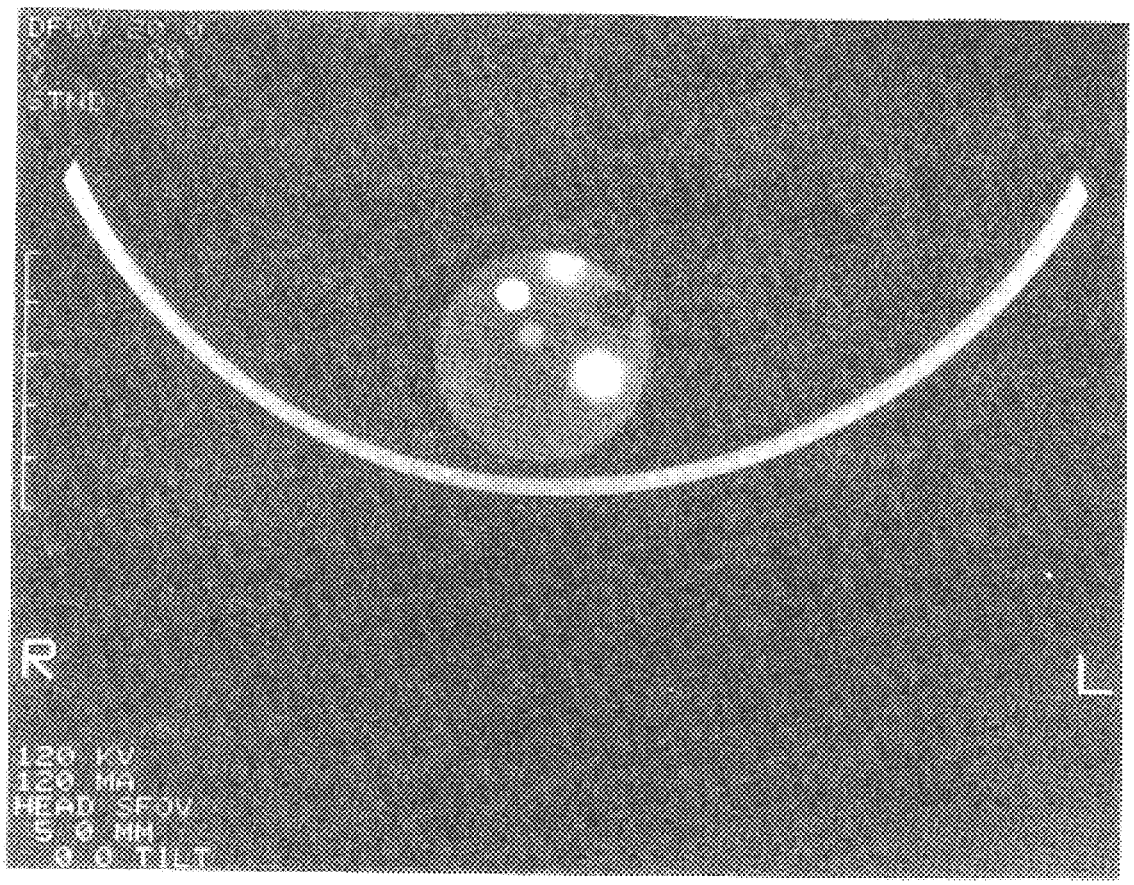
FIG. 4 is a CT X-ray showing a polyacrylamide gel phantom within which several gel channels are doped with different contrast agents.
Figure 4B:
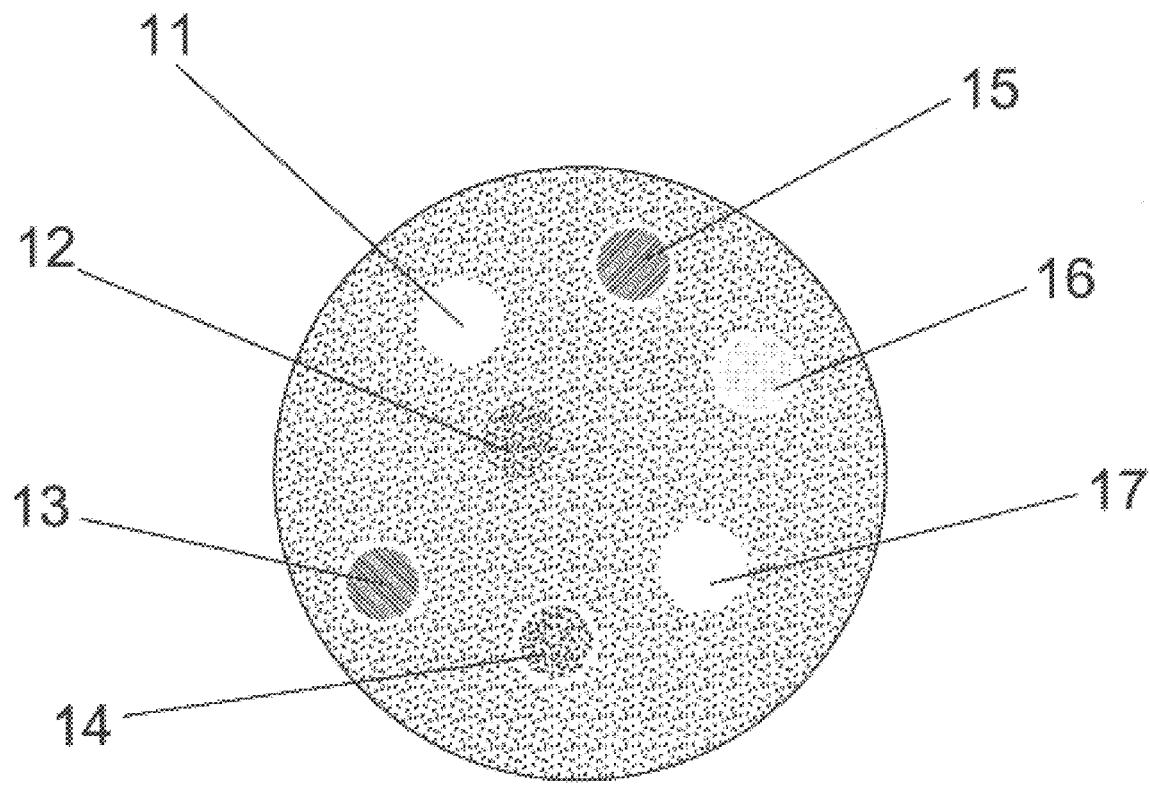
Figure 9A:
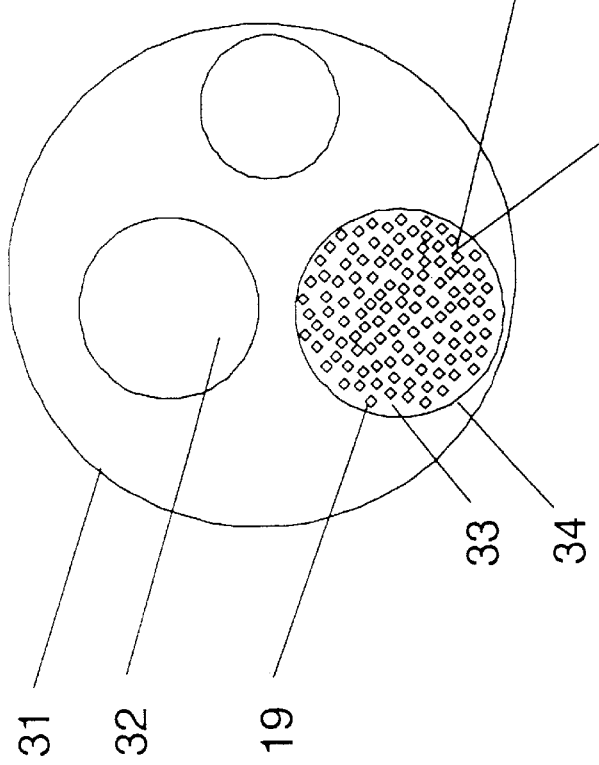
FIG. 9 is a two part schematic of a peripheral nerve including 31) the epineurium sheath, 32) a fascicle, 33) the endoneurial space of a fascicle, 34) the perineurium surrounding the endoneurial space and which is the site of the blood/nerve barrier to small molecule diffusion, 19) a motor axon seen in cross section, 35) a schwann cell surrounding an enlarged single axon, 36) a mitochondrion within the axon seen in cross section, 37) the axolemma or membrane of the axon, 38) a microtubule within the axon and dimension marks indication the 20 micron diameter of the motor axon.
Figure 9B:
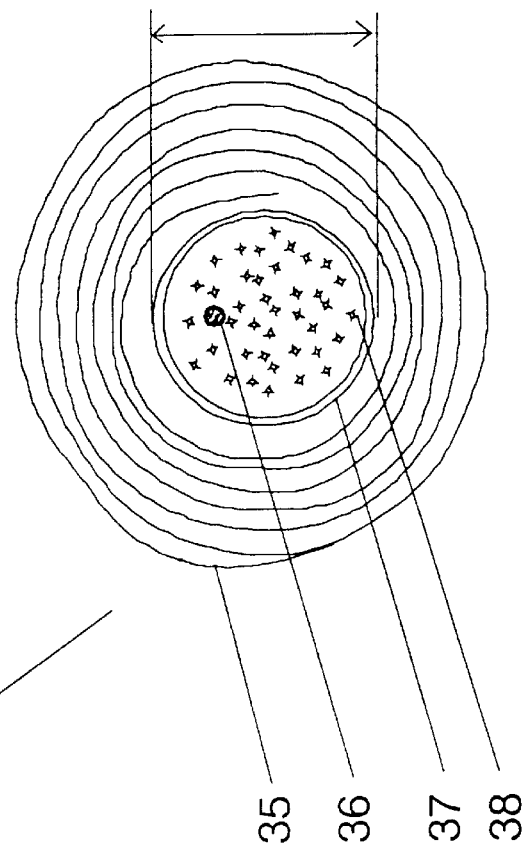
Figure 10:
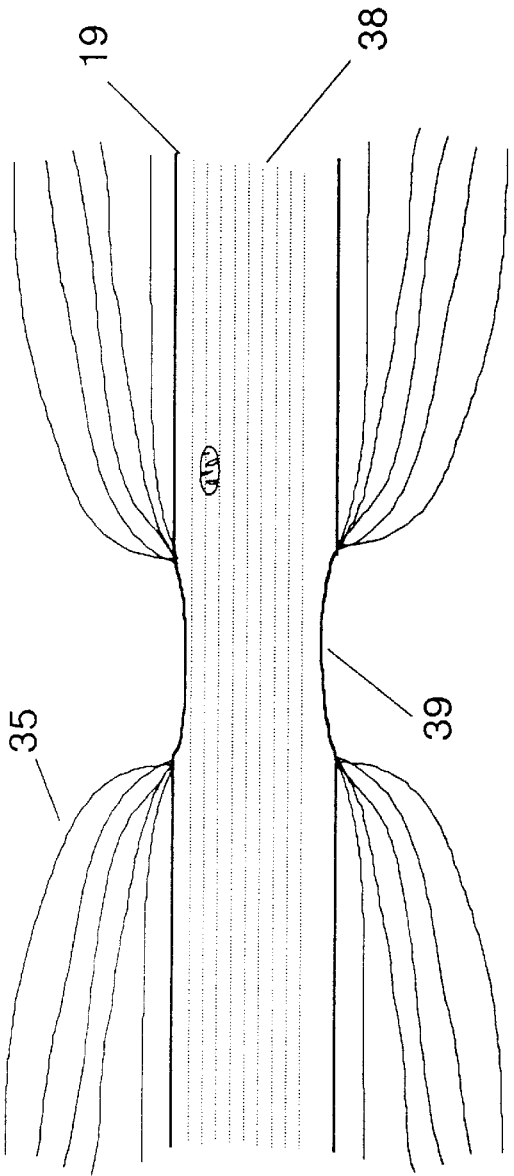
FIG. 10 shows an axon in longitudinal section with 35) a schwann cell sheath, 39) a Node of Ranvier between two schwann cells, and 38) microtubules within the axon (19).
Figure 11:
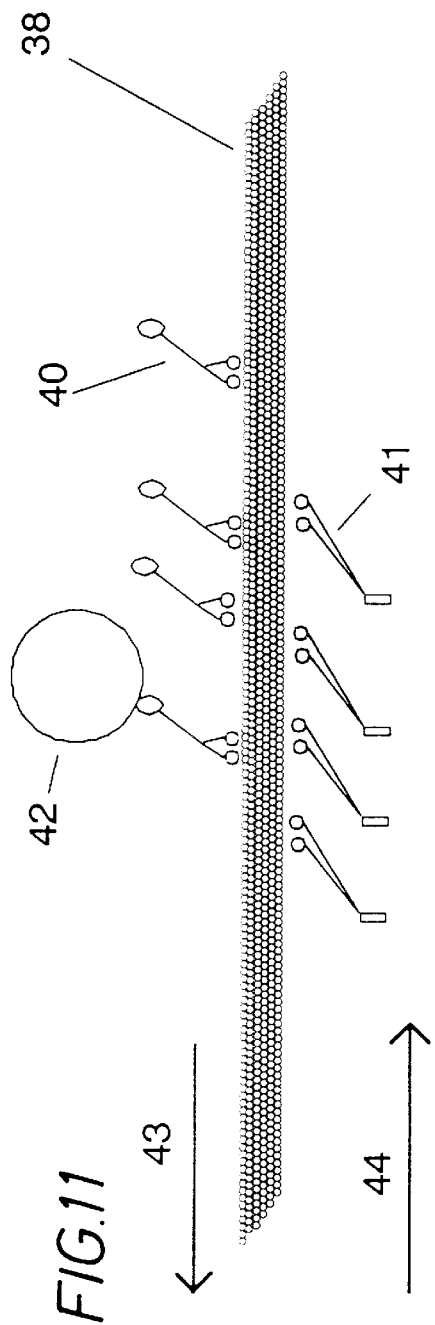
FIG. 11 depicts the mechanics underlying axonal transport based on a relatively stationary microtubule (38) with 40) one of a series of molecules of dynein and 41) one of a series of molecules of kinesin, in which 42) a lipid vesicle is being transported in 43) a retrograde direction toward the cell body and 44) the anterograde direction.
Figure 12:
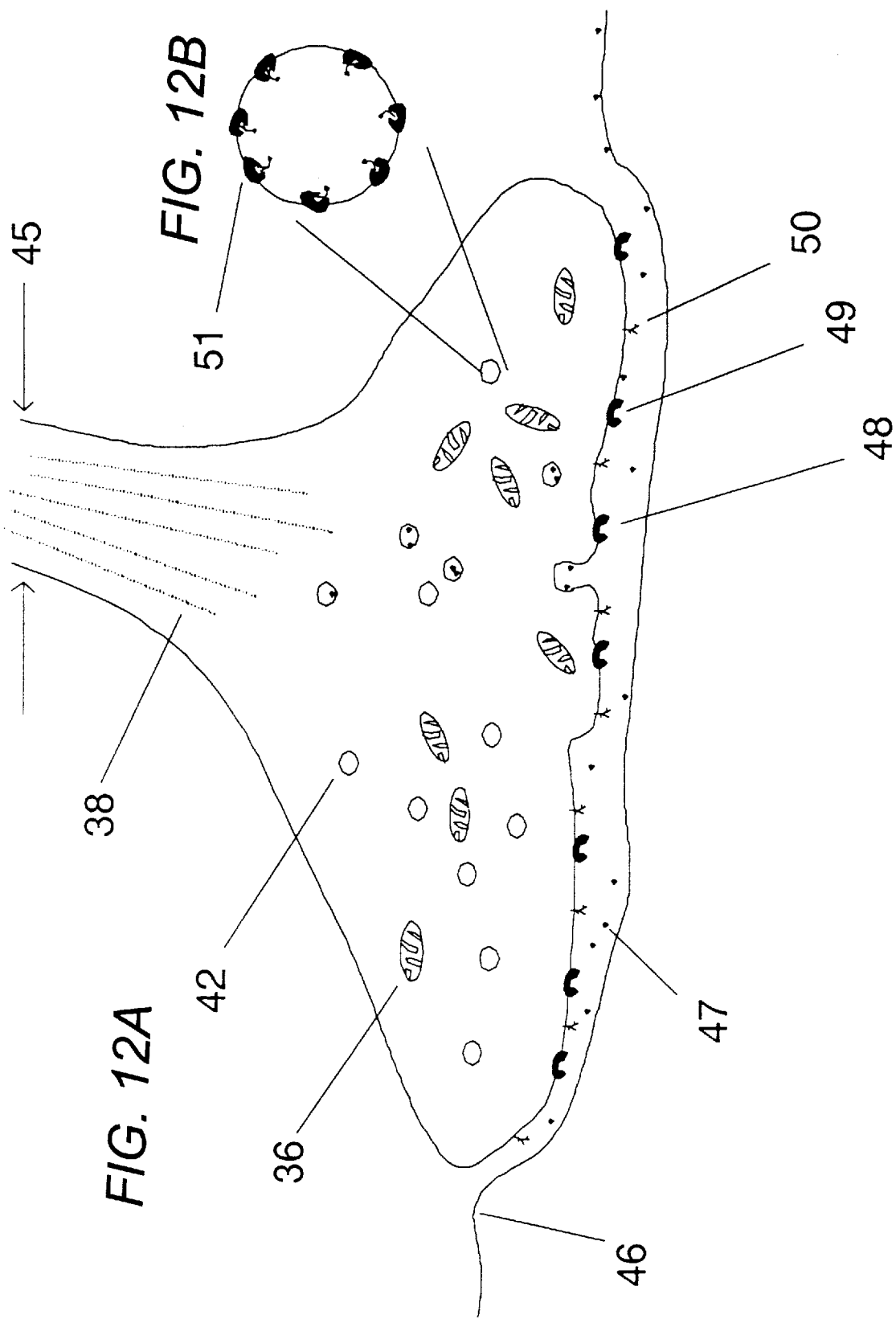
FIG. 12 demonstrates some of the parts of an axon terminus with 38) a microtubule, 42) a vesicle, 36) a mitochondrion, 46) the muscle cell membrane, 47) a 20 to 50 nm dextran coated ferrite particle, 48) the synaptic cleft, 49) a cell surface receptor, 50) a cell surface marker or antigen, 51) a vesicle containing an internalized group of receptor ligand complexes, and 45) the diameter of the axon which is 2 to 10 microns.
Figure 13:
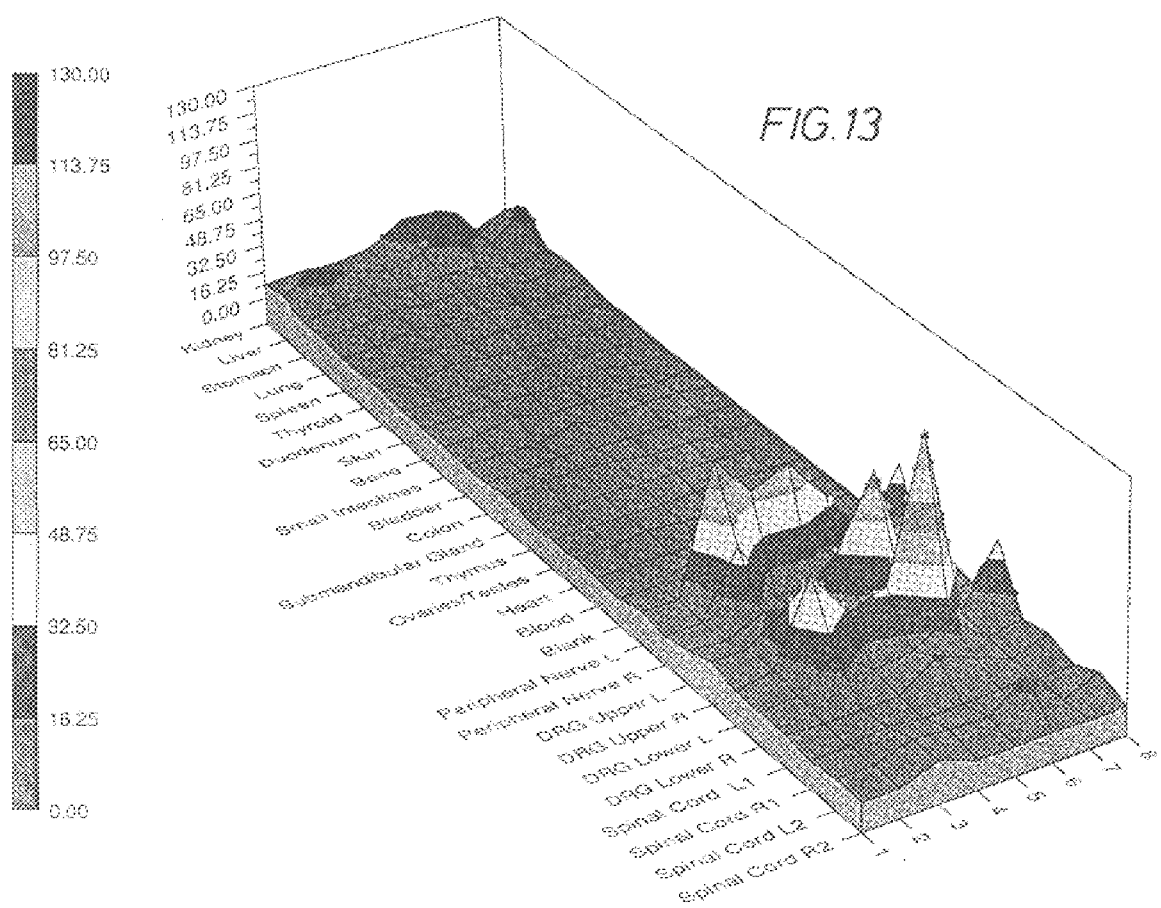
FIG. 13 is a graph depicting the results of the $^{125}$I-WGA distribution study in which the vertical axis gives counts per minute per gm of tissue normalized by dividing by the cpm/gm of blood for the individual animal in the series, various tissues are displayed along the long Y axis and lines 1 through 8 reflect the results from the different animals with varying treatment/survival times and doses. DRG signifies spin al roots and dorsal root ganglia and demonstrates concentrations 5–10 times higher than any other tissue except the muscle and lymph nodes near the injection site which are not shown.
Figure 14:
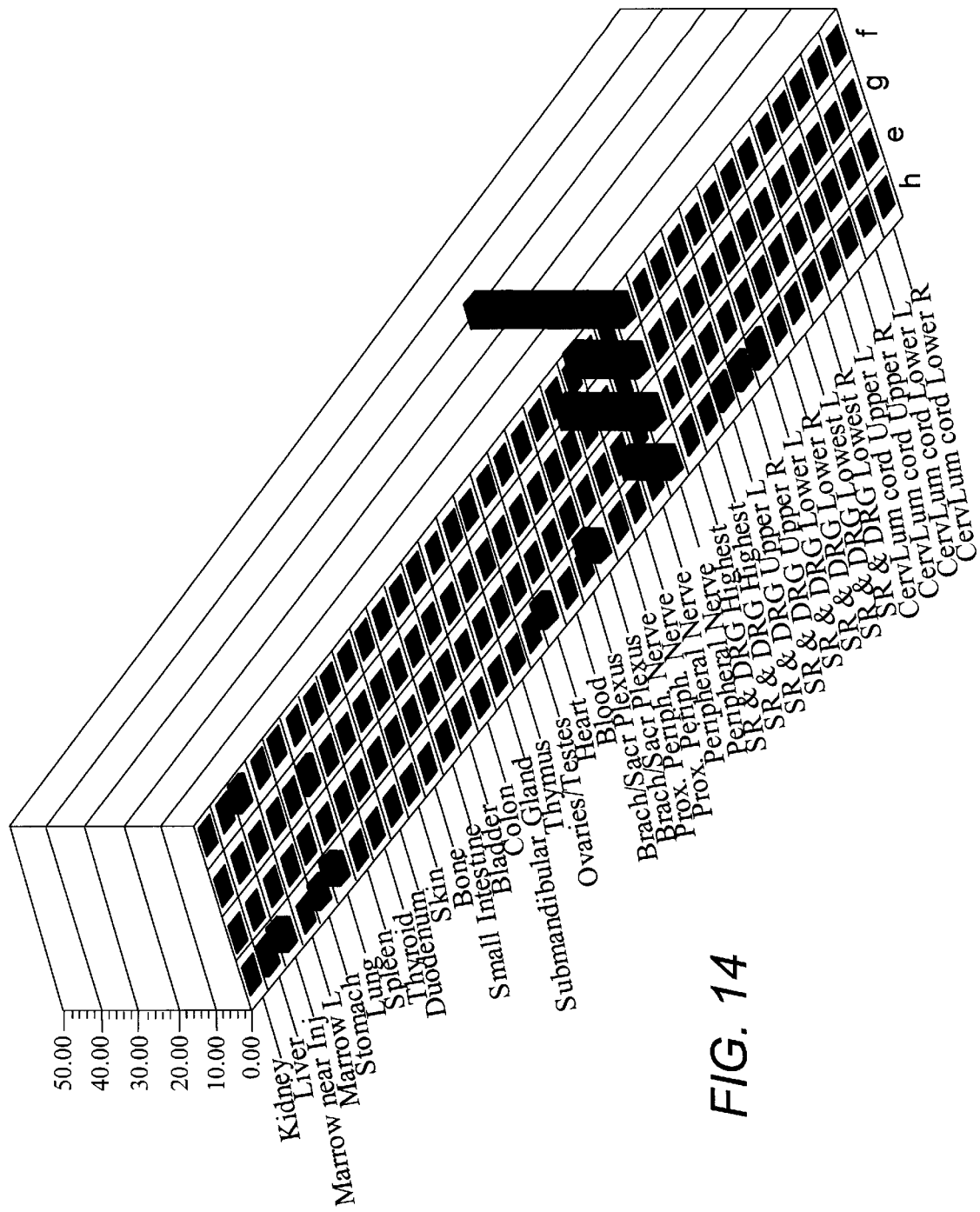
FIG. 14 is a graph depicting the results of a $^{59}$Fe WGA-dextran magnetite distribution study after intramuscular injection. Counts per minute/gm tissue show concentration in distal and proximal ipsilateral peripheral nerve which are 50 to 100 times higher than in any other tissue excluding the muscle and lymph nodes at the injection site which are not shown.
Figure 15:
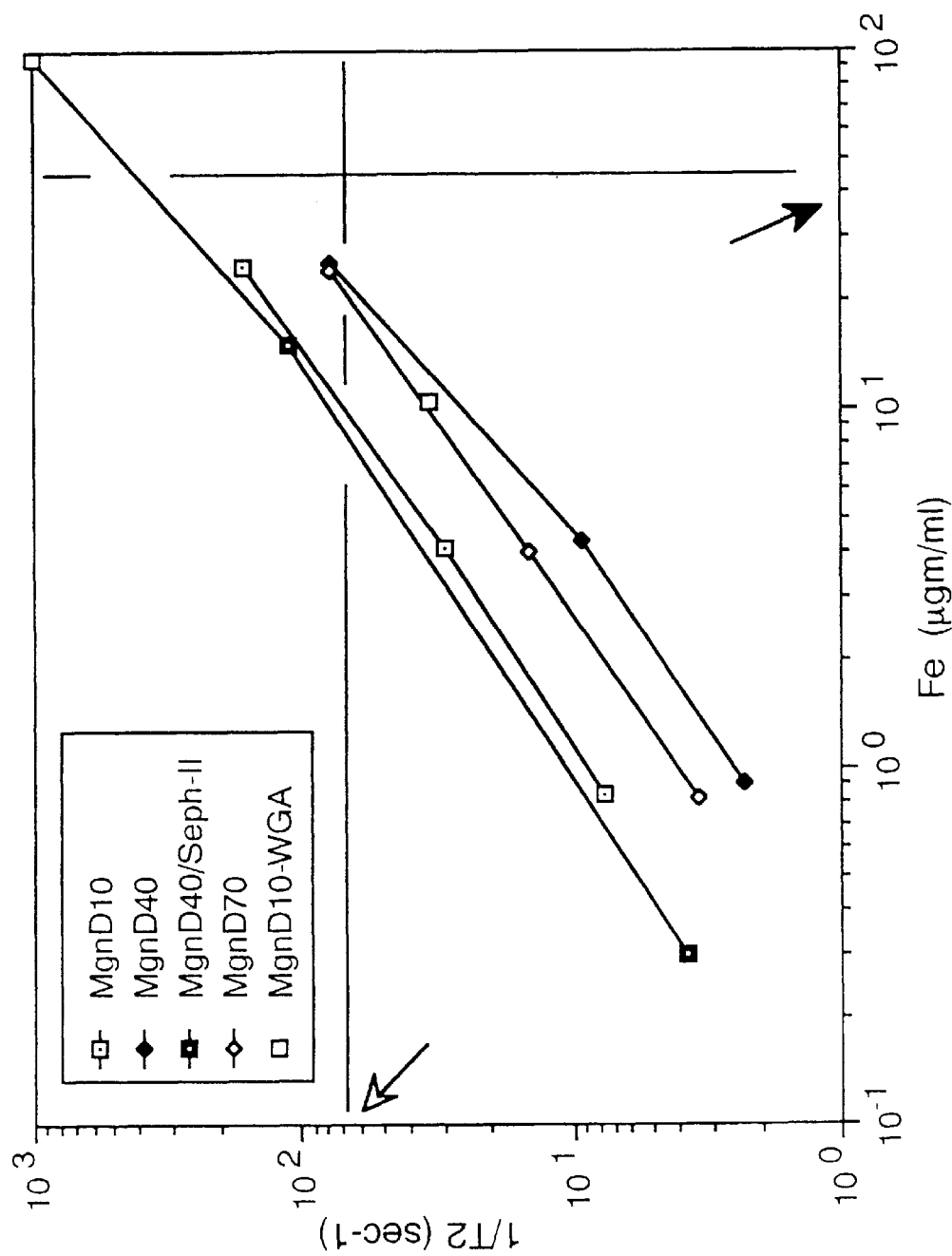
FIG. 15 is a graph showing results of $T_2$ measurements upon polyacrylamide gels doped with varying concentration of various preparations of dextran coated magnetite. The white arrow indicates a $T_2$ of 30 msec which would be a 40% reduction from normal $T_2$ of nerve and the black arrow indicates concentrations of ferrite particles achieved in nerve equivalent and greater than 40 micrograms/ml. The concentrations in nerve are up to ten times higher than the amounts required to reduce $T_2$ in gel below 30 msec.
Figure 18:
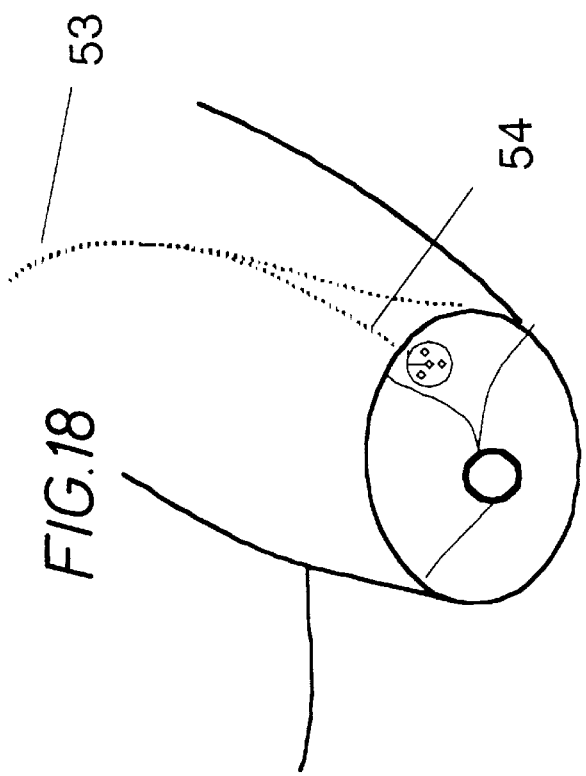
FIG. 18 shows a cross section through the thigh with 53) the sciatic nerve and 54) the tibial nerve approaching an implanted cuff.
Figure 19:
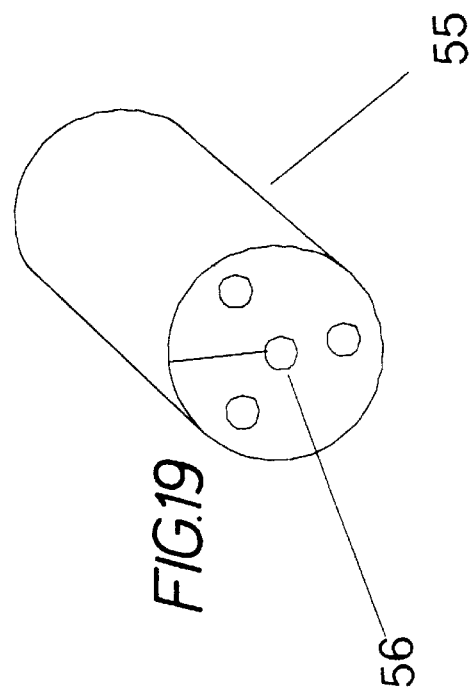
FIG. 19 demonstrates the silastic cuff (55) with a central channel (56) for the tibial nerve and three surrounding channels for various doped polyacrylamide gels used to standardize image contrast. The central channel is about 1 mm in diameter.
Figure 16:
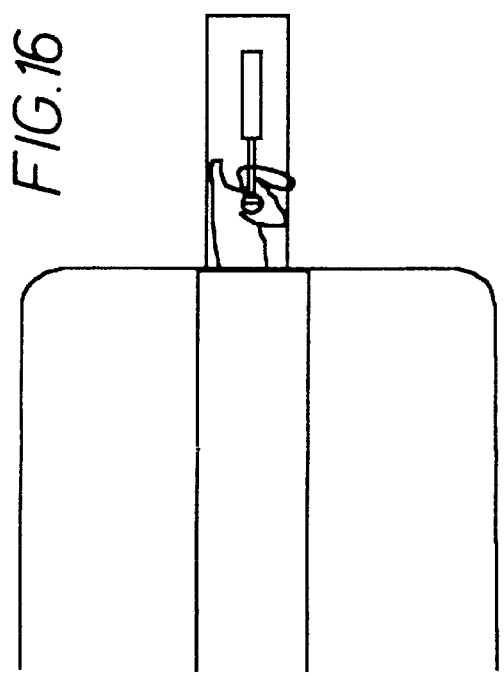
FIG. 16 demonstrates the general arrangements for in vivo MR microscopy of an intact nerve in the leg of experimental animal showing the position before being moved into the MR magnet. Note that the leg is perpendicular to the long axis of the magnet.
Figure 17:
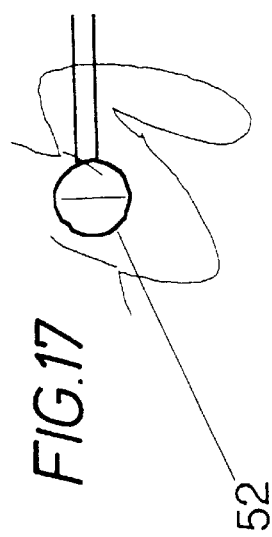
FIG. 17 enlarges the view of FIG. 16 to show a surface coil (52) placed around an incision line on the skin of the thigh.
Figure 20A:
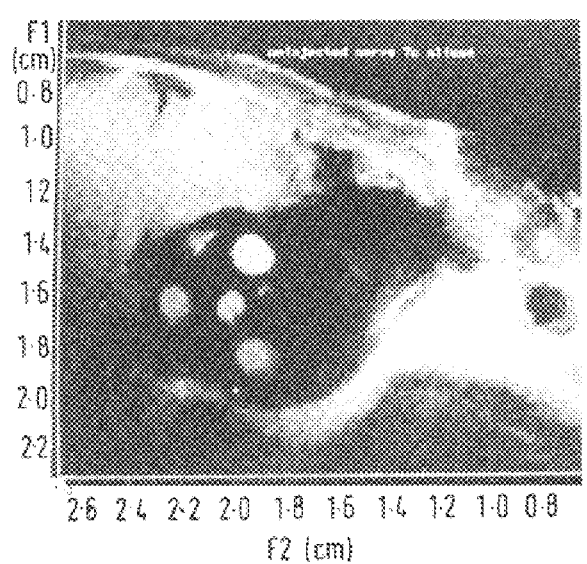
FIG. 20 includes photographs of the tibial nerve in the silastic cuff from 57) the uninjected leg and 58) the injected side. The nerve is in the central channel and is darker than the lower gel channels in the injected leg but brighter in the uninjected side.
Figure 20B:
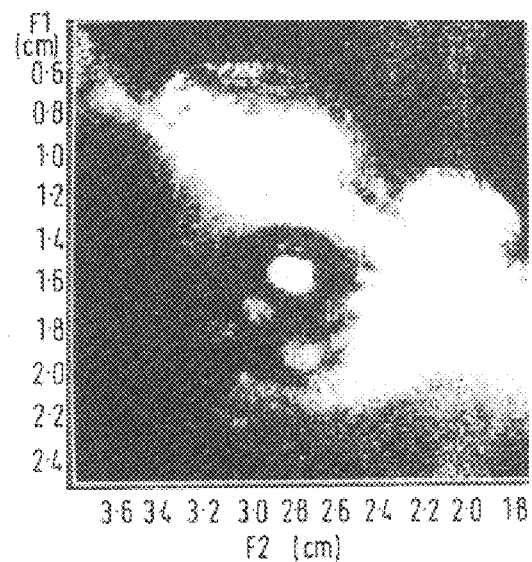
Figure 21:
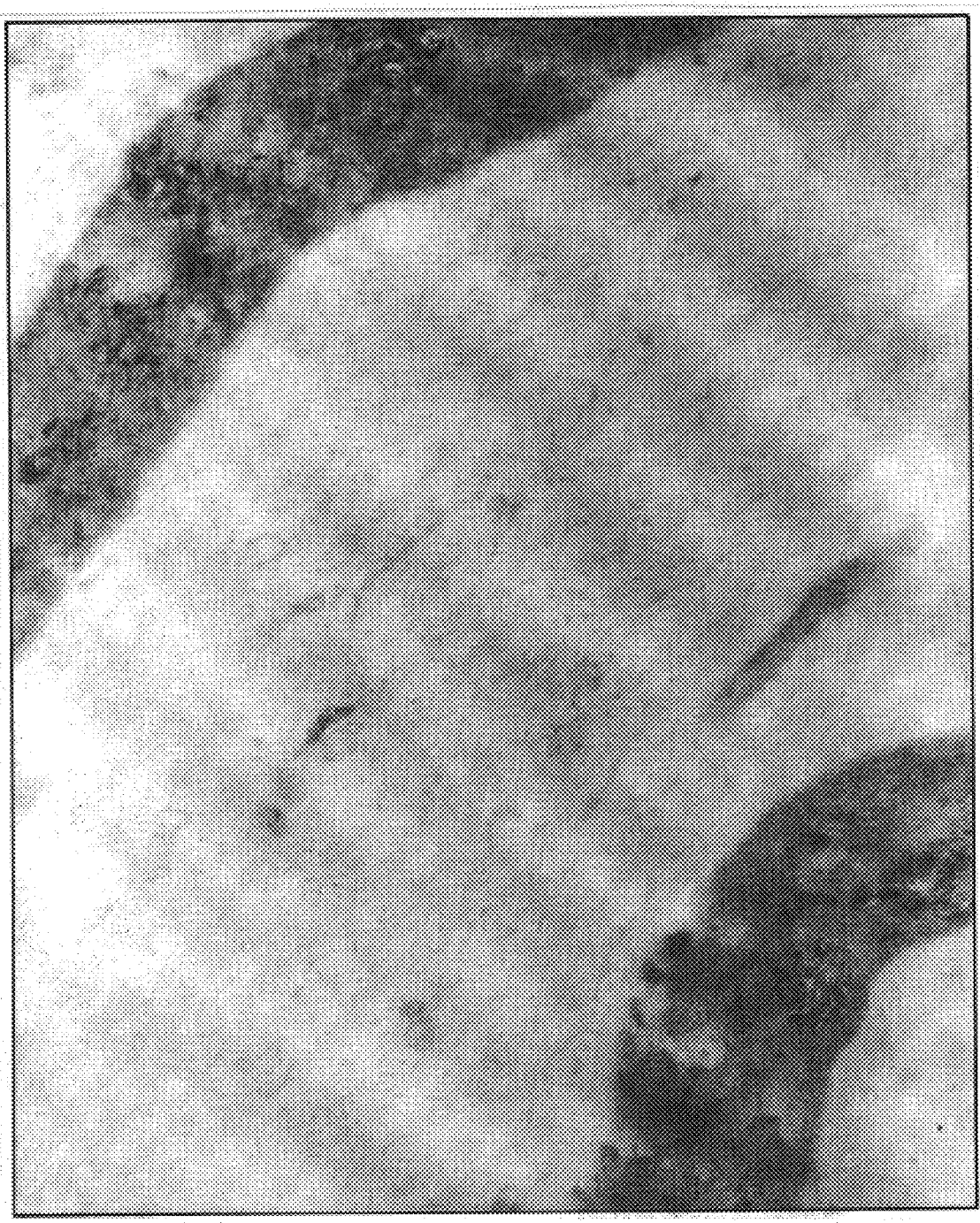
Figure 22:
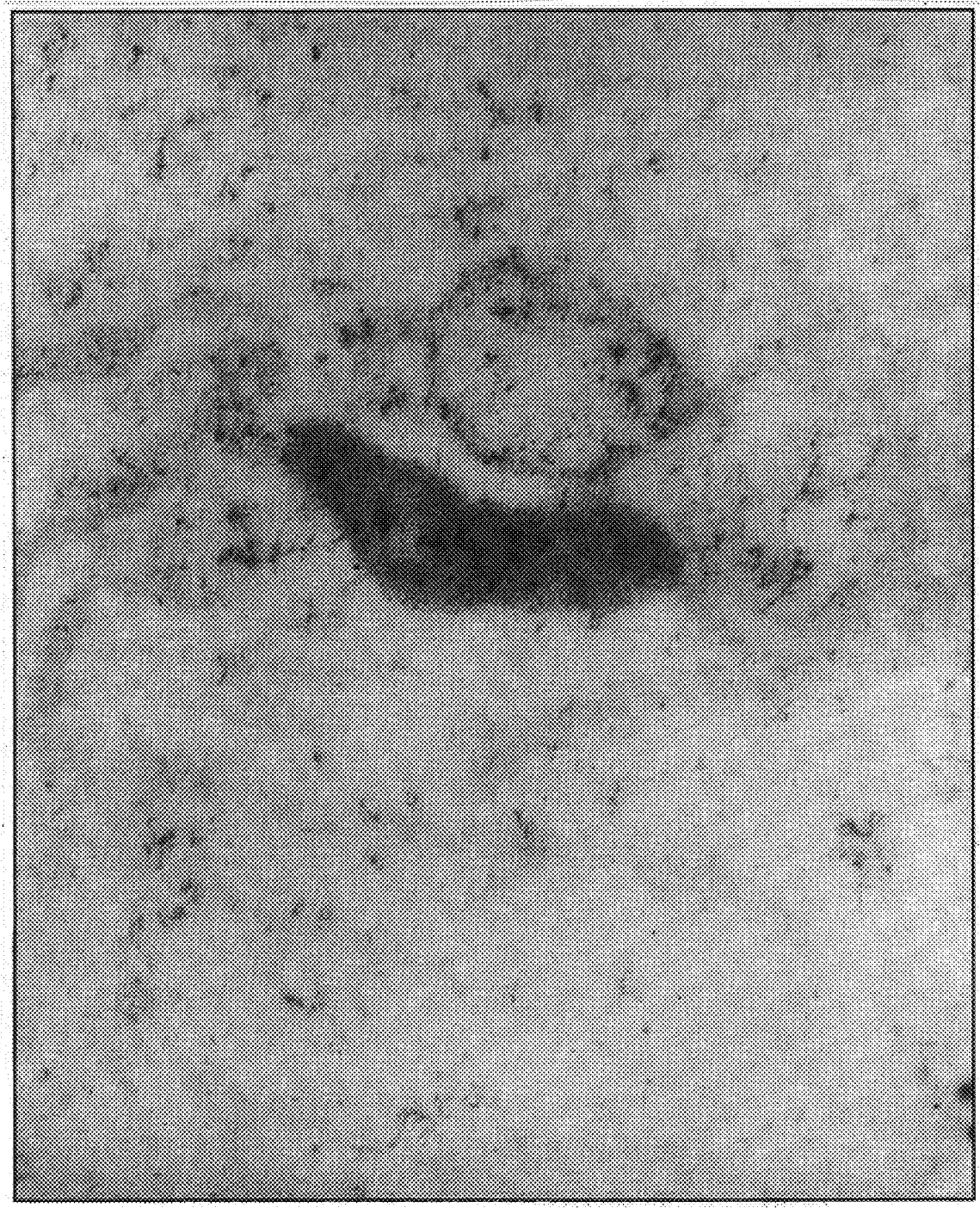
FIG. 22 is a blow up of a portion of FIG. 21 to 195,000×. This demonstrates small ferrite particles along the microtubules as well as somewhat larger particles within two vesicles being transported.
Figure 23A:
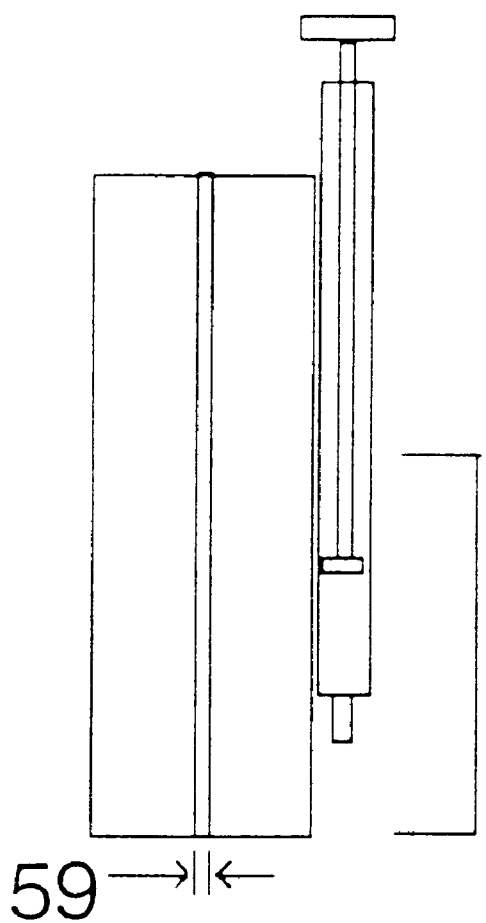
FIG. 23 demonstrates the results of a positron emission tomography trial with $^{52}$Mn dextran coated ferrite particles. There is a "nerve gel" one millimeter in diameter (59) cast within a larger "leg gel" where the ratio of concentrations of the positron emitting ferrites is 25:1 (nerve:leg), a relation reflecting the results of earlier distribution trials.
Figure 23B:
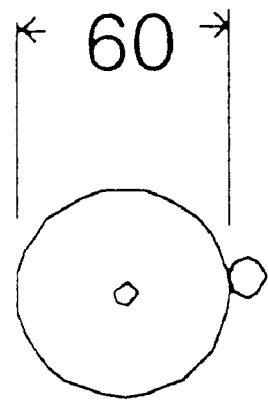
Figure 23C:
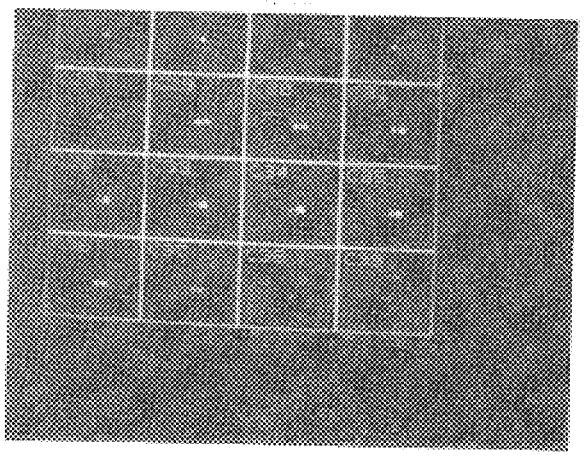
Figure 23D:
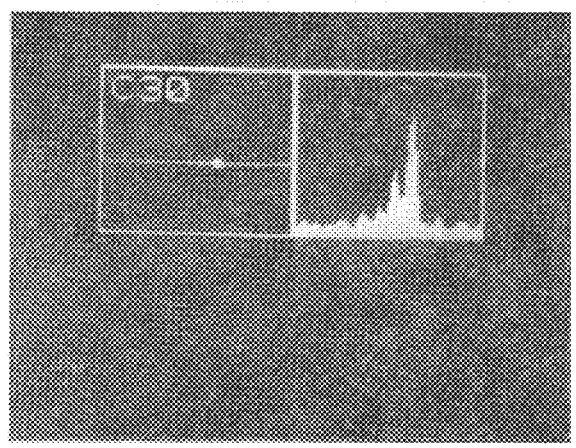
Figure 23E:
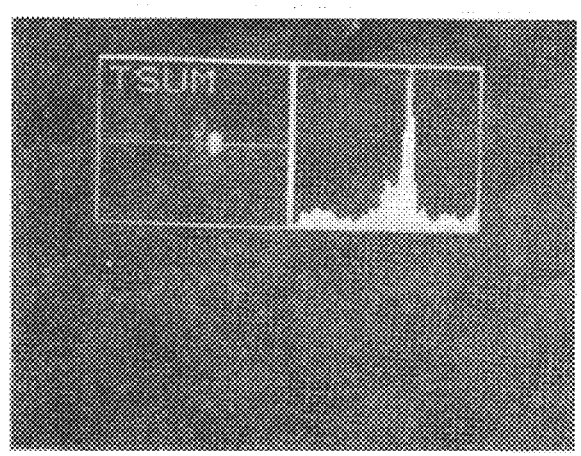

The diameter of the test tube is about 2.2 cm (60) and there is a 1 milliliters syringe taped to the outside which also contains concentrated $^{52}$Mn Ferrite. Cross sectional images (61) show ready distinction between the two high concentration sources and this is demonstrated in two dimensional format in 62. Seen from anteriorly, the two sources can still be distinguished.

I claim:

1. A method of treating a living human or non-human body to generate a therapeutic or prophylactic treatment or assist diagnostic investigation or surgical treatment thereof, said method comprising administering into a vascularized peripherally innervated tissue site or into other tissue sites innervated by a spinal root a particulate pharmaceutical agent comprising a nerve adhesion moiety serving to promote neuronal endocytosis of said agent and a physiologically active or diagnostic marker moiety for axonal transport from said tissue site.

2. A method of treating a living human or non-human body in need of therapeutic, prophylactic or diagnostic treatment, comprising administering into a vascularized peripherally innervated tissue site or into other tissue sites innervated by a spinal root, a therapeutic, prophylactic or diagnostic composition comprising a nerve adhesion moiety wherein said nerve adhesion moiety is a particulate pharmaceutical agent subject to neuronal endocytosis, said agent further comprising a physiologically active or diagnostic marker moiety for axonal transport following neuronal endocytosis of said agent.

3. A pharmaceutical agent comprising a nerve adhesion molecule coupled to an optionally-coated, particulate, physiologically active or diagnostically marked substance, said substance being one selected from the group consisting of metal oxide, metal sulfide and alloy when said substance is diagnostically marked, wherein said physiologically active or diagnostically marked substance is axonal transport following neuronal endocytosis of said agent, and wherein said particulate have a mean particle size of 10–50 nm.

4. A composition as claimed in claim 4 wherein said particles have a spinel structure.

5. A composition as claimed in claim 5 wherein said particles are superparamagnetic.

6. A composition as claimed in claim 6 wherein said particles incorporate radionuclides.

7. The method, according to claim 1, wherein said particulate pharmaceutical agent is administered in solution.

8. The method, according to claim 1, wherein said particulate pharmaceutical agent comprises a carrier particle coated with a hydrophilic molecule to which said nerve adhesion moiety and said physiologically active or diagnostically marked moiety are bound.

9. The method, according to claim 8, wherein said hydrophilic molecule is dextran.

10. The method, according to claim 8, wherein said carrier particle is a metal oxide.

11. The method, according to claim 2, wherein said particulate pharmaceutical agent is administered in solution.

12. The method, according to claim 2, wherein said particulate pharmaceutical agent comprises a carrier particle coated with a hydrophilic molecule to which said nerve adhesion moiety and said physiologically active or diagnostically marked moiety are bound.

13. The method, according to claim 12, wherein said hydrophilic molecule is dextran.

14. The method, according to claim 12, wherein said carrier particle is a metal oxide.

15. The pharmaceutical agent, according to claim 3, wherein said pharmaceutical agent is administered in solution.

16. The pharmaceutical agent, according to claim 4, wherein said pharmaceutical agent comprises a carrier particle coated with a hydrophilic molecule to which said nerve adhesion moiety and said physiologically active or diagnostically marked moiety are bound.

17. The pharmaceutical agent, according to claim 16, wherein said hydrophilic molecule is dextran.

18. The method, according to claim 16, wherein said carrier particle is a metal oxide.

19. A pharmaceutical agent comprising a nerve-adhesion molecule coupled to an optionally-coated, particulate, physiologically active or diagnostically marked substance, said substance being one selected from the group consisting or metal oxide, metal sulphide and alloy when said substance is diagnostically marked, wherein said physiologically active or diagnostically marked substance is for axonal transport following neuronal endocytosis of said agent.

* * * * *